United States Patent
Rushton

(10) Patent No.: US 11,649,463 B2
(45) Date of Patent: May 16, 2023

(54) TRICHOME SPECIFIC PROMOTERS FOR THE MANIPULATION OF CANNABINOIDS AND OTHER COMPOUNDS IN GLANDULAR TRICHOMES

(71) Applicant: 22nd Century Limited, LLC, Williamsville, NY (US)

(72) Inventor: Paul Rushton, Buffalo, NY (US)

(73) Assignee: 22nd Century Limited, LLC, Buffalo, NY (US)

( * ) Notice: Subject to any disclaimer, the term of this patent is extended or adjusted under 35 U.S.C. 154(b) by 121 days.

(21) Appl. No.: 16/987,078

(22) Filed: Aug. 6, 2020

(65) Prior Publication Data

US 2021/0040492 A1 Feb. 11, 2021

Related U.S. Application Data

(62) Division of application No. 16/334,284, filed as application No. PCT/US2017/051493 on Sep. 14, 2017, now Pat. No. 10,787,674.

(60) Provisional application No. 62/397,212, filed on Sep. 20, 2016.

(51) Int. Cl.
C12N 15/82 (2006.01)

(52) U.S. Cl.
CPC .............................. C12N 15/8223 (2013.01)

(58) Field of Classification Search
None
See application file for complete search history.

(56) References Cited

U.S. PATENT DOCUMENTS

| | | |
|---|---|---|
| 6,730,826 B2 | 5/2004 | Wagner et al. |
| 8,809,626 B2 | 8/2014 | Bleeker et al. |
| 2010/0218283 A1 | 8/2010 | Ro et al. |
| 2013/0067619 A1 | 3/2013 | Page et al. |
| 2014/0057251 A1 | 2/2014 | McKernan |
| 2014/0298511 A1 | 10/2014 | Lewis et al. |
| 2015/0315602 A1 | 11/2015 | Diergaarde et al. |
| 2016/0177404 A1 | 6/2016 | McKernan |

FOREIGN PATENT DOCUMENTS

| | | |
|---|---|---|
| WO | WO 2013/006953 A1 | 1/2013 |
| WO | WO 2014/084739 A1 | 6/2014 |
| WO | WO 2015/196275 A1 | 12/2015 |
| WO | WO 2016/030828 A1 | 3/2016 |

OTHER PUBLICATIONS

Pottier et al, 2020, Planta, 251:57-58.*
International Search Report and Written Opinion issued in International Patent Application No. PCT/US2017/051493, dated Mar. 7, 2018.
Search Report issued in European Patent Application No. 17853690. 0, dated Jun. 29, 2020.
Isvett Josefina Flores-Sanches, et al., "Secondary metabolism in cannabis," Phytochmistry Reviews, vol. 7, No. 3, pp. 615-639 (Apr. 2008).
Taura, et al., "Characterization of olivetol synthase, a polyketide synthase putatively involved in cannabinoid biosynthetic pathway,:" FEBS Letters, vol. 583, No. 12, pp. 2061-2066 (Jun. 2009).
Harm van Bakel, et al., "The draft genome and transcriptome of Cannabis sativa", Genome Biology, Biomed Central Ltd, vol. 12, No. 10, p. R102, (Oct. 2011).
Gutierrez-Alcala, et al., "A versatile promoter for the expression of proteins in glandular and non-glandular trichomes from a variety of plants," Journ. of Experimental Botany, vol. 56, No. 419, pp. 2487-2494 (Jul. 2005).
International Preliminary Report on Patentability issued in International Patent Application No. PCT/US2017/051493, dated Mar. 26, 2019.
Japanese Notice of Reasons for Refusal issued in co-pending Japanese Patent Application No. 2019-515321, dated Aug. 31, 2021.
Office Action and Search Report issued in Chinese Patent Application No. 201780070846.4, dated Nov. 14, 2022.
Kim et al., "Analysis of Natural and Induced Variation in tomato Glandular Trichome Flavonoids Identifies a gene Not Present in the Reference Genome," Plant Cell, vol. 26, No. 8, pp. 3272-3285 (Aug. 2014.).

* cited by examiner

Primary Examiner — Jason Deveau Rosen

(74) Attorney, Agent, or Firm — Foley & Lardner LLP

(57) ABSTRACT

The present technology provides trichome specific promoters of cannabinoid biosynthesis enzyme genes from Cannabis, nucleotide sequences of the trichome specific promoters, and uses of the promoters for modulating the production of cannabinoids and other compounds in organisms. The present technology also provides chimeric genes, vectors, and transgenic cells and organisms, including plant cells and plants, comprising the trichome specific promoters. Also provided are methods for expressing nucleic acid sequences in cells and organisms using the trichome specific promoters.

13 Claims, 4 Drawing Sheets
Specification includes a Sequence Listing.

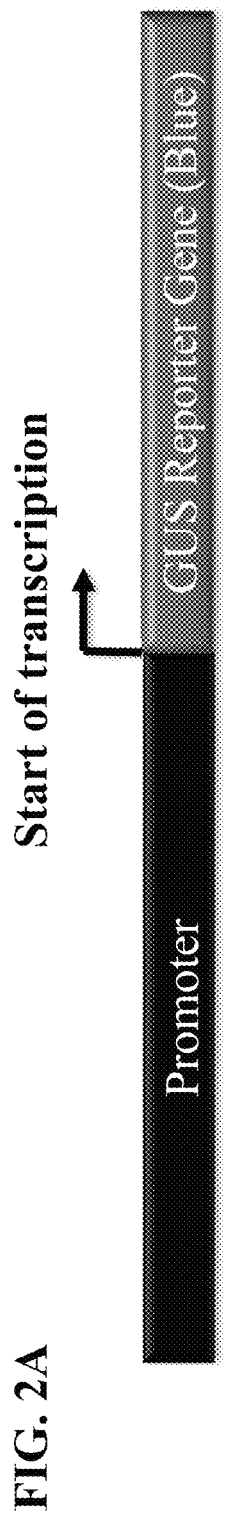
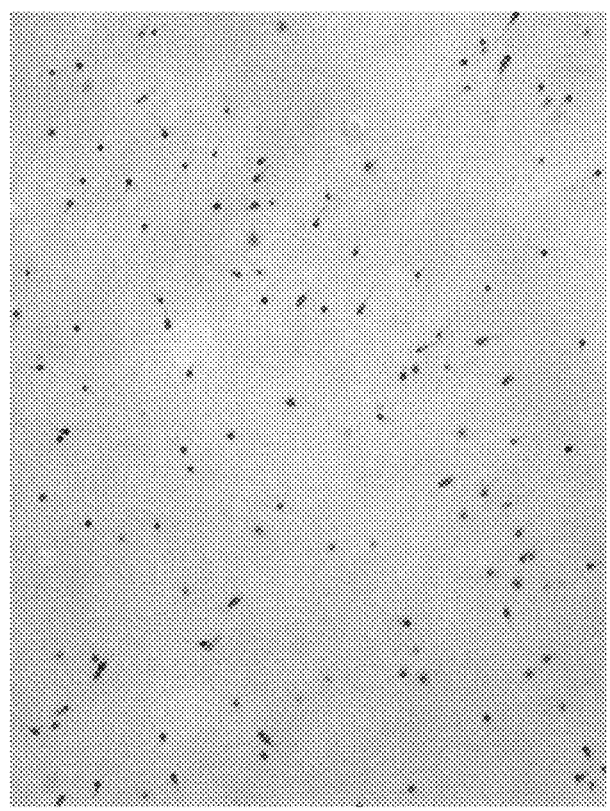
FIG. 2A
FIG. 2B

TRICHOME SPECIFIC PROMOTERS FOR THE MANIPULATION OF CANNABINOIDS AND OTHER COMPOUNDS IN GLANDULAR TRICHOMES

CROSS-REFERENCE TO RELATED APPLICATIONS

The present application is a Divisional of U.S. patent application Ser. No. 16/334,284, filed Mar. 18, 2019, which is the U.S. National Stage of International Patent Application No. PCT/US2017/051493, filed Sep. 14, 2017, which claims priority from U.S. Provisional Patent Application No. 62/397,212, filed Sep. 20, 2016, the contents of these applications are hereby incorporated by reference in their entirety.

TECHNICAL FIELD

The present technology relates generally to trichome specific promoters of cannabinoid biosynthesis enzyme genes from *Cannabis*, nucleotide sequences of the trichome specific promoters, and uses of the promoters for modulating cannabinoid production or for modulating other trichome specific production of biochemicals in organisms. The present technology also relates to transgenic cells and organisms, including plant cells and plants, comprising the trichome specific promoters.

BACKGROUND

The following description is provided to assist the understanding of the reader. None of the information provided or references cited is admitted to be prior art.

Plant trichomes are epidermal protuberances, including branched and unbranched hairs, vesicles, hooks, spines, and stinging hairs covering the leaves, bracts, and stems. There are two major classes of trichomes, which may be distinguished on the basis of their capacity to produce and secrete or store secondary metabolites, namely glandular trichomes and non-glandular trichomes. Non-glandular trichomes exhibit low metabolic activity and provide protection to the plant mainly through physical means. By contrast, glandular trichomes, which are present on the foliage of many plant species including some solanaceous species (e.g., tobacco, tomato) and also *cannabis*, are highly metabolically active and accumulate metabolites, which can represent up to 10-15% of the leaf dry weight (Wagner et al., *Ann. Bot.* 93:3-11 (2004)). Glandular trichomes are capable of secreting (or storing) secondary metabolites as a defense mechanism.

*Cannabis sativa* L. (*cannabis*, hemp, marijuana), an annual herb that has been cultivated for thousands of years, contains a unique set of secondary metabolites called cannabinoids, which constitute a group of terpenophenolics. Cannabinoids are primarily synthesized and accumulate in glandular trichomes that are present at high densities on female flowers and at lower densities on male flowers of *C. sativa* plants. The accumulation of cannabinoids in the storage cavity of trichomes is beneficial to the plant as cannabinoids are known to be cytotoxic to other plant cells and have been shown to induce apoptosis in both hemp and tobacco cell suspension cultures (Sirikantaramas et al., *Plant Cell Physiol.* 46:1578-1582 (2005)). Cannabinoids are formed by a three-step biosynthetic process: polyketide formation, aromatic prenylation, and cyclization (FIG. 1). The cannabinoid pathway is supplied by hexanoyl-CoA, the formation of which is catalyzed by hexanoyl-CoA synthetase. The first enzymatic step in cannabinoid biosynthesis is the formation of 3,5,7-trioxododecanoyl-CoA by a tetraketide synthase enzyme (TKS), termed olivetolic acid synthase (OLS1). The second enzymatic step in cannabinoid biosynthesis is the formation of olivetolic acid by olivetolic acid cyclase (OAC). The next step is the prenylation of olivetolic acid to form cannabigerolic acid (CBGA) by the aromatic prenyltransferase. CBGA is a central branch-point intermediate for the biosynthesis of the different major classes of cannabinoids. Alternative cyclization of the prenyl side-chain of CBGA yields $\Delta^9$tetrahydrocannabinolic acid (THCA) or its isomers cannabidiolic acid (CBDA) or cannabichromenic acid (CBCA). THCA and CBDA are later decarboxylated by a non-enzymatic reaction during storage or smoking to yield $\Delta^9$-tetrahydrocannabinol (THC) or cannabidiol (CBD), respectively (FIG. 1).

Cannabinoids are valuable plant-derived natural products. *Cannabis* preparations, such as marijuana and hashish, have been used for centuries for their well-known psychoactive effects. Cannabinoids have attracted a renewed interest for medical applications due to their ability to act through mammalian cannabinoid receptors. Major cannabinoids include $\Delta^9$-tetrahydrocannabinol (THC), the compound responsible for the psychoactive and therapeutic effects of marijuana consumption, and cannabidiol (CBD), which has neuroprotective properties. (Gaoni & Mechoulam, *J. Am. Chem. Sc.* 86:1646-1647 (1964): Mechoulam et al., *J. Clin. Pharmacol.* 42:11S-19S (2002)). THCA is the major cannabinoid in drug strains of *cannabis* while CBDA is the predominant cannabinoid in hemp forms grown for fiber or seed. Cannabinoids are currently being explored for therapeutic purposes, including the treatment of chronic pain, nausea, the control of spasticity and tremor in patients suffering from multiple sclerosis or epilepsy, as well as a therapy for arthritis. The possibility to direct cannabinoid production in trichomes avoids interference in the plants' metabolic pathways and performance. Accordingly, there is a need to identify trichome specific promoters to modulate the synthesis of cannabinoids in organisms including transgenic plants, transgenic cells, and derivatives thereof, which allow for targeting of gene expression specifically in trichomes.

SUMMARY

Disclosed herein are trichome specific promoters and uses of these promoters for directing the expression of coding nucleic acid sequences in plant trichomes.

In one aspect, the present disclosure provides a synthetic DNA molecule comprising a nucleotide sequence selected from the group consisting of: (a) a nucleotide sequence set forth in any one of SEQ ID NOs: 1-3, 5, 6, 8, 9, 11-14, 16-19, 21-26, 28, 29, or 31-33; and (b) a nucleotide sequence that is at least about 80% identical to the nucleotide sequence of any one of SEQ ID NOs: 1-3, 5, 6, 8, 9, 11-14, 16-19, 21-26, 28, 29, or 31-33, and which encodes a promoter having plant trichome gland specific transcriptional activity, wherein the nucleotide sequence is operably linked to a heterologous nucleic acid.

In some embodiments, the present disclosure provides an expression vector comprising the synthetic DNA molecule operably linked to one or more nucleic acid sequences encoding a polypeptide.

In some embodiments, the present disclosure provides a genetically engineered host cell comprising the expression vector. In some embodiments, the genetically engineered host cell is a *Cannabis sativa* cell. In some embodiments, the genetically engineered host cell is a *Nicotiana tabacum* cell.

In some embodiments, the present disclosure provides a genetically engineered plant comprising a cell comprising a chimeric nucleic acid construct comprising the synthetic DNA molecule. In some embodiments, the genetically engineered plant belongs to the family Solanacea. In some embodiments, the engineered Solanacea plant is an *N. tabacum* plant. In some embodiments, the genetically engineered plant belongs to the family Cannabaceae. In some embodiments, the engineered Cannabaceae plant is a *C. sativa* plant. In some embodiments, the present disclosure provides seeds from the genetically engineered plant, wherein the seeds comprise the chimeric nucleic acid construct.

In some embodiments, the present disclosure provides a synthetic DNA molecule with the nucleotide sequence as set forth in SEQ ID NO: 1. In some embodiments, the present disclosure provides a synthetic DNA molecule having a nucleotide sequence that is at least about 80% identical to the nucleotide sequence of SEQ ID NO: 1, and which encodes a promoter that has plant trichome gland specific transcriptional activity.

In some embodiments, the present disclosure provides a synthetic DNA molecule with the nucleotide sequence as set forth in SEQ ID NO: 2. In some embodiments, the present disclosure provides a synthetic DNA molecule having a nucleotide sequence that is at least about 80% identical to the nucleotide sequence of SEQ ID NO: 2, and which encodes a promoter that has plant trichome gland specific transcriptional activity.

In some embodiments, the present disclosure provides a synthetic DNA molecule with the nucleotide sequence as set forth in SEQ ID NO: 3. In some embodiments, the present disclosure provides a synthetic DNA molecule having a nucleotide sequence that is at least about 80% identical to the nucleotide sequence of SEQ ID NO: 3, and which encodes a promoter that has plant trichome gland specific transcriptional activity.

In some embodiments, the present disclosure provides a synthetic DNA molecule with the nucleotide sequence as set forth in SEQ ID NO: 5. In some embodiments, the present disclosure provides a synthetic DNA molecule having a nucleotide sequence that is at least about 80% identical to the nucleotide sequence of SEQ ID NO: 5, and which encodes a promoter that has plant trichome gland specific transcriptional activity.

In some embodiments, the present disclosure provides a synthetic DNA molecule with the nucleotide sequence as set forth in SEQ ID NO: 6. In some embodiments, the present disclosure provides a synthetic DNA molecule having a nucleotide sequence that is at least about 80% identical to the nucleotide sequence of SEQ ID NO: 6, and which encodes a promoter that has plant trichome gland specific transcriptional activity.

In some embodiments, the present disclosure provides a synthetic DNA molecule with the nucleotide sequence as set forth in SEQ ID NO: 8. In some embodiments, the present disclosure provides a synthetic DNA molecule having a nucleotide sequence that is at least about 80% identical to the nucleotide sequence of SEQ ID NO: 8, and which encodes a promoter that has plant trichome gland specific transcriptional activity.

In some embodiments, the present disclosure provides a synthetic DNA molecule with the nucleotide sequence as set forth in SEQ ID NO: 9. In some embodiments, the present disclosure provides a synthetic DNA molecule having a nucleotide sequence that is at least about 80% identical to the nucleotide sequence of SEQ ID NO: 9, and which encodes a promoter that has plant trichome gland specific transcriptional activity.

In some embodiments, the present disclosure provides a synthetic DNA molecule with the nucleotide sequence as set forth in SEQ ID NO: 11. In some embodiments, the present disclosure provides a synthetic DNA molecule having a nucleotide sequence that is at least about 80% identical to the nucleotide sequence of SEQ ID NO: 11, and which encodes a promoter that has plant trichome gland specific transcriptional activity.

In some embodiments, the present disclosure provides a synthetic DNA molecule with the nucleotide sequence as set forth in SEQ ID NO: 12. In some embodiments, the present disclosure provides a synthetic DNA molecule having a nucleotide sequence that is at least about 80% identical to the nucleotide sequence of SEQ ID NO: 12, and which encodes a promoter that has plant trichome gland specific transcriptional activity.

In some embodiments, the present disclosure provides a synthetic DNA molecule with the nucleotide sequence as set forth in SEQ ID NO: 13. In some embodiments, the present disclosure provides a synthetic DNA molecule having a nucleotide sequence that is at least about 80% identical to the nucleotide sequence of SEQ ID NO: 13, and which encodes a promoter that has plant trichome gland specific transcriptional activity.

In some embodiments, the present disclosure provides a synthetic DNA molecule with the nucleotide sequence as set forth in SEQ ID NO: 14. In some embodiments, the present disclosure provides a synthetic DNA molecule having a nucleotide sequence that is at least about 80% identical to the nucleotide sequence of SEQ ID NO: 14, and which encodes a promoter that has plant trichome gland specific transcriptional activity.

In some embodiments, the present disclosure provides a synthetic DNA molecule with the nucleotide sequence as set forth in SEQ ID NO: 16. In some embodiments, the present disclosure provides a synthetic DNA molecule having a nucleotide sequence that is at least about 80% identical to the nucleotide sequence of SEQ ID NO: 16, and which encodes a promoter that has plant trichome gland specific transcriptional activity.

In some embodiments, the present disclosure provides a synthetic DNA molecule with the nucleotide sequence as set forth in SEQ ID NO: 17. In some embodiments, the present disclosure provides a synthetic DNA molecule having a nucleotide sequence that is at least about 80% identical to the nucleotide sequence of SEQ ID NO: 17, and which encodes a promoter that has plant trichome gland specific transcriptional activity.

In some embodiments, the present disclosure provides a synthetic DNA molecule with the nucleotide sequence as set forth in SEQ ID NO: 18. In some embodiments, the present disclosure provides a synthetic DNA molecule having a nucleotide sequence that is at least about 80% identical to the nucleotide sequence of SEQ ID NO: 18, and which encodes a promoter that has plant trichome gland specific transcriptional activity.

In some embodiments, the present disclosure provides a synthetic DNA molecule with the nucleotide sequence as set forth in SEQ ID NO: 19. In some embodiments, the present disclosure provides a synthetic DNA molecule having a nucleotide sequence that is at least about 80% identical to the nucleotide sequence of SEQ ID NO: 19, and which encodes a promoter that has plant trichome gland specific transcriptional activity.

In some embodiments, the present disclosure provides a synthetic DNA molecule with the nucleotide sequence as set forth in SEQ ID NO: 21. In some embodiments, the present disclosure provides a synthetic DNA molecule having a nucleotide sequence that is at least about 80% identical to the nucleotide sequence of SEQ ID NO: 21, and which encodes a promoter that has plant trichome gland specific transcriptional activity.

In some embodiments, the present disclosure provides a synthetic DNA molecule with the nucleotide sequence as set forth in SEQ ID NO: 22. In some embodiments, the present disclosure provides a synthetic DNA molecule having a nucleotide sequence that is at least about 80% identical to the nucleotide sequence of SEQ ID NO: 22, and which encodes a promoter that has plant trichome gland specific transcriptional activity.

In some embodiments, the present disclosure provides a synthetic DNA molecule with the nucleotide sequence as set forth in SEQ ID NO: 23. In some embodiments, the present disclosure provides a synthetic DNA molecule having a nucleotide sequence that is at least about 80% identical to the nucleotide sequence of SEQ ID NO: 23, and which encodes a promoter that has plant trichome gland specific transcriptional activity.

In some embodiments, the present disclosure provides a synthetic DNA molecule with the nucleotide sequence as set forth in SEQ ID NO: 24. In some embodiments, the present disclosure provides a synthetic DNA molecule having a nucleotide sequence that is at least about 80% identical to the nucleotide sequence of SEQ ID NO: 24, and which encodes a promoter that has plant trichome gland specific transcriptional activity.

In some embodiments, the present disclosure provides a synthetic DNA molecule with the nucleotide sequence as set forth in SEQ ID NO: 25. In some embodiments, the present disclosure provides a synthetic DNA molecule having a nucleotide sequence that is at least about 80% identical to the nucleotide sequence of SEQ ID NO: 25, and which encodes a promoter that has plant trichome gland specific transcriptional activity.

In some embodiments, the present disclosure provides a synthetic DNA molecule with the nucleotide sequence as set forth in SEQ ID NO: 26. In some embodiments, the present disclosure provides a synthetic DNA molecule having a nucleotide sequence that is at least about 80% identical to the nucleotide sequence of SEQ ID NO: 26, and which encodes a promoter that has plant trichome gland specific transcriptional activity.

In some embodiments, the present disclosure provides a synthetic DNA molecule with the nucleotide sequence as set forth in SEQ ID NO: 28. In some embodiments, the present disclosure provides a synthetic DNA molecule having a nucleotide sequence that is at least about 80% identical to the nucleotide sequence of SEQ ID NO: 28, and which encodes a promoter that has plant trichome gland specific transcriptional activity.

In some embodiments, the present disclosure provides a synthetic DNA molecule with the nucleotide sequence as set forth in SEQ ID NO: 29. In some embodiments, the present disclosure provides a synthetic DNA molecule having a nucleotide sequence that is at least about 80% identical to the nucleotide sequence of SEQ ID NO: 29, and which encodes a promoter that has plant trichome gland specific transcriptional activity.

In some embodiments, the present disclosure provides a synthetic DNA molecule with the nucleotide sequence as set forth in SEQ ID NO: 31. In some embodiments, the present disclosure provides a synthetic DNA molecule having a nucleotide sequence that is at least about 80% identical to the nucleotide sequence of SEQ ID NO: 31, and which encodes a promoter that has plant trichome gland specific transcriptional activity.

In some embodiments, the present disclosure provides a synthetic DNA molecule with the nucleotide sequence as set forth in SEQ ID NO: 32. In some embodiments, the present disclosure provides a synthetic DNA molecule having a nucleotide sequence that is at least about 80% identical to the nucleotide sequence of SEQ ID NO: 32, and which encodes a promoter that has plant trichome gland specific transcriptional activity.

In some embodiments, the present disclosure provides a synthetic DNA molecule with the nucleotide sequence as set forth in SEQ ID NO: 33. In some embodiments, the present disclosure provides a synthetic DNA molecule having a nucleotide sequence that is at least about 80% identical to the nucleotide sequence of SEQ ID NO: 33, and which encodes a promoter that has plant trichome gland specific transcriptional activity.

In one aspect, the present disclosure provides a genetically engineered plant or plant cell comprising a chimeric gene integrated into its genome, the chimeric gene comprising a trichome specific promoter operably linked to a homologous or heterologous nucleic acid sequence, wherein the promoter is selected from the group consisting of: (a) a nucleotide sequence of any one of SEQ ID NOs: 1-3, 5, 6, 8, 9, 11-14, 16-19, 21-26, 28, 29, or 31-33; and (b) a nucleotide sequence that is at least about 80% identical to the nucleotide sequence of any one of SEQ ID NOs: 1-3, 5, 6, 8, 9, 11-14, 16-19, 21-26, 28, 29, or 31-33, and which encodes a promoter that has plant trichome gland specific transcriptional activity.

In some embodiments, the genetically engineered plant or plant cell belongs to the family Solanacea. In some embodiments, the Solanacea plant is *N. tabacum*. In some embodiments, the genetically engineered plant belongs to the family Cannabaceae. In some embodiments, the engineered Cannabaceae plant is *C. sativa*.

In one aspect, the present disclosure provides a method for expressing a polypeptide in plant trichomes, comprising: (a) introducing into a host cell an expression vector comprising a nucleotide sequence selected from the group consisting of: (i) a nucleotide sequence set forth in any one of SEQ ID NOs: 1-3, 5, 6, 8, 9, 11-14, 16-19, 21-26, 28, 29, or 31-33; and (ii) a nucleotide sequence that is at least about 80% identical to the nucleotide sequence of any one of SEQ ID NOs: 1-3, 5, 6, 8, 9, 11-14, 16-19, 21-26, 28, 29, or 31-33, and which encodes a promoter that has plant trichome gland specific transcriptional activity; wherein the nucleic acid sequence of (i) or (ii) is operably linked to one or more nucleic acid sequences encoding a polypeptide; and (b) growing the plant under conditions which allow for the expression of the polypeptide.

In another aspect, the present disclosure provides a method for increasing a cannabinoid in a host plant trichome, comprising: (a) introducing into a host cell an expression vector comprising a nucleotide sequence selected from the group consisting of: (i) a nucleotide sequence set forth in any one of SEQ ID NOs: 1-3, 5, 6, 8, 9, 11-14, 16-19, 21-26, 28, 29, or 31-33: and (ii) a nucleotide sequence that is at least about 80% identical to the nucleotide sequence of any one of SEQ ID NOs: 1-3, 5, 6, 8, 9, 11-14, 16-19, 21-26, 28, 29, or 31-33, and which encodes a promoter that has plant trichome gland specific transcriptional activity; wherein the nucleic acid sequence of (i) or (ii) is operably linked to one or more nucleic acid sequences encoding an enzyme of the cannabinoid biosynthetic pathway: and (b) growing the plant under conditions which allow for the expression of the cannabinoid biosynthetic pathway enzyme; wherein expression of the cannabinoid biosynthetic pathway enzyme results in the plant having an increased cannabinoid content relative to a control plant grown under similar conditions.

In some embodiments of the method, the cannabinoid biosynthetic pathway enzyme is cannabidiolic acid (CBDA) synthase, cannabichromenic acid (CBCA) synthase or $\Delta^9$tetrahydrocannabinolic acid (THCA) synthase.

In some embodiments, the method further comprises providing the plant with cannabigerolic acid (CBGA).

In some embodiments, the present disclosure provides a method for producing a genetically-engineered plant having increased $\Delta^9$tetrahydrocannabinol (THC), cannabichromene (CBC), and/or cannabidiol (CBD) content relative to a control plant.

The technologies described and claimed herein have many attributes and embodiments including, but not limited to, those set forth or described or referenced in this brief summary. It is not intended to be all-inclusive and the inventions described and claimed herein are not limited to or by the features or embodiments identified in this brief summary, which is included for purposes of illustration only and not restriction. Additional embodiments may be disclosed in the detailed description below.

In one aspect, the present disclosure provides a synthetic DNA molecule comprising a nucleotide sequence selected from the group consisting of: (a) a nucleotide sequence set forth in any one of SEQ ID NOs: 31, 32, or 33; and (b) a nucleotide sequence that is at least about 80% identical to the nucleotide sequence of any one of SEQ ID NOs: 31, 32, or 33, and which encodes a promoter having plant trichome gland specific transcriptional activity, wherein the nucleotide sequence is operably linked to a heterologous nucleic acid.

In some embodiments, the present disclosure provides an expression vector comprising the synthetic DNA molecule operably linked to one or more nucleic acid sequences encoding a polypeptide.

In some embodiments, the present disclosure provides a genetically engineered host cell comprising the expression vector. In some embodiments, the genetically engineered host cell is a *Cannabis sativa* cell. In some embodiments, the genetically engineered host cell is a *Nicotiana tabacum* cell.

In some embodiments, the present disclosure provides a genetically engineered plant comprising a cell comprising a chimeric nucleic acid construct comprising the synthetic DNA molecule. In some embodiments, the engineered plant is an *N. tabacum* plant. In some embodiments, the engineered plant is a *C. sativa* plant.

In some embodiments, the present disclosure provides seeds from the engineered plant of any one of 5, wherein the seeds comprise the chimeric nucleic acid construct.

In one aspect, the present disclosure provides a synthetic DNA molecule comprising a nucleotide sequence set forth in SEQ ID NO: 33.

In some embodiments, the present disclosure provides an expression vector comprising the synthetic DNA molecule operably linked to one or more nucleic acid sequences encoding a polypeptide.

In some embodiments, the present disclosure provides a genetically engineered host cell comprising the expression vector. In some embodiments, the genetically engineered host cell is a *Cannabis sativa* cell. In some embodiments, the genetically engineered host cell is a *Nicotiana tabacum* cell.

In some embodiments, the present disclosure provides a genetically engineered plant comprising a cell comprising a chimeric nucleic acid construct comprising the synthetic DNA molecule. In some embodiments, the engineered plant is an *N. tabacum* plant. In some embodiments, the engineered plant is a *C. sativa* plant.

In some embodiments, the present disclosure provides seeds from the engineered plant, wherein the seeds comprise the chimeric nucleic acid construct.

BRIEF DESCRIPTION OF THE DRAWINGS

FIGS. 2A-2B show the promoter:reporter gene design utilized in the experiments described herein. Each promoter is fused to the GUS reporter gene and promoter activity is indicated by a blue color upon staining (FIG. 2A). FIG. 2B is a whole leaf view of trichome specific expression of cannabinoid biosynthetic enzyme gene promoters in tobacco trichomes. Results from a representative promoter (CBDA synthase 20800 gene promoter) are shown. Results from the other promoters in the cannabinoid biosynthetic pathway are qualitatively identical (not shown). FIG. 2B shows that expression of the reporter gene is restricted to the trichomes.

DETAILED DESCRIPTION

I. Introduction

Figure 1:
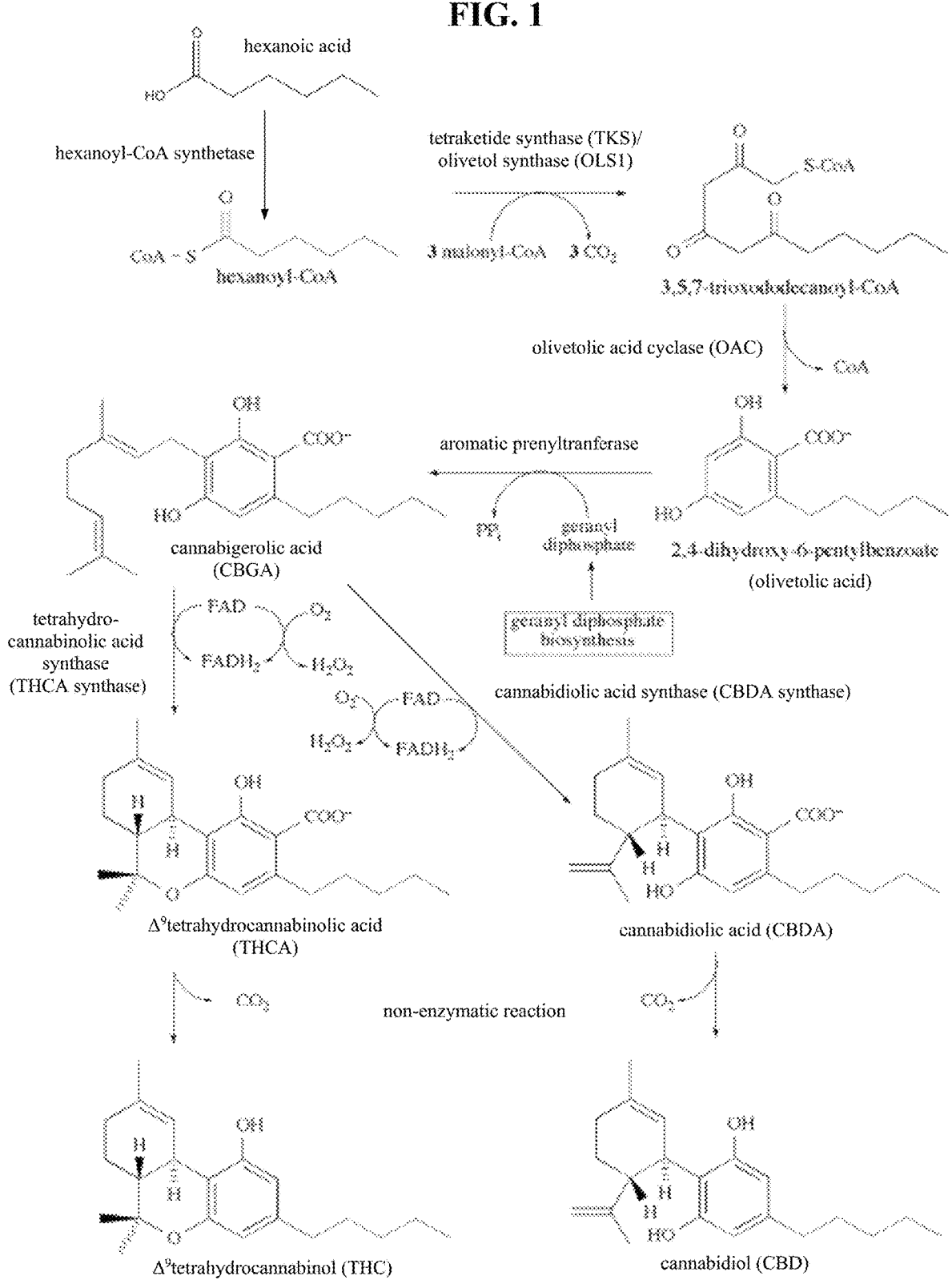
FIG. 1 depicts the cannabinoid biosynthetic pathway that leads to the formation of the major cannabinoids in *Cannabis sativa*, $\Delta^9$-tetrahydrocannabinolic acid (THCA) and cannabidiolic acid (CBDA).

The present technology relates to the discovery of nucleic acid sequences for twenty-three trichome specific promoters of enzymes involved in the cannabinoid biosynthetic pathway: (1) olivetol synthase (OLS; also referred to as tetraketide synthase) promoter; (2) OLS1 promoter; (3) OLS2 promoter; (4) olivetolic acid cyclase (OAC) promoter; (5) OAC1 promoter; (6) aromatic prenyltransferase (PT) promoter; (7) PT1 promoter; (8) hexanoyl-CoA synthetase (AAE1-1) promoter; (9) hexanoyl-CoA synthetase (AAE1-1') promoter; (10) hexanoyl-CoA synthetase (AAE3) promoter; (11) hexanoyl-CoA synthetase (AAE12) promoter; (12) CBDA synthase (CBDAS) promoter; (13) CBDA synthase 1 (CBDAS1) promoter; (14) CBDA synthase (CBDAS) 20800 promoter; (15) CBDA synthase (CBDAS) 20800' promoter; (16) THCA synthase (THCAS) 19603 promoter; (17) THCA synthase (THCAS) 19603' promoter; (18) THCA synthase (THCAS) 50320 promoter: (19) THCA synthase (THCAS) 50320' promoter: (20) THCA synthase (THCAS) 1330 promoter; (21) THCA synthase (THCAS) 1330' promoter; (22) CBDA synthase (CBDAS) 3498 promoter: and (23) CBDA synthase (CBDAS) 3498' promoter.

The nucleic acid sequences for each promoter have been determined. The nucleic acid sequences of the (i) olivetol synthase (OLS) promoter, (ii) OLS1 promoter, and (iii) OLS2 promoter are set forth in SEQ ID NOs: 1, 2, and 3, respectively, and the open reading frame (ORF) of OLS is set forth in SEQ ID NO: 4. The nucleic acid sequence of the olivetolic acid cyclase (OAC) promoter is set forth in SEQ ID NO: 5, the nucleic acid sequence of the OAC1 promoter is set forth in SEQ ID NO: 6, and the ORF of OAC is set forth in SEQ ID NO: 7. The nucleic acid sequence of aromatic prenyltransferase (PT) promoter is set forth in SEQ ID NO: 8, the nucleic acid sequence of the PT1 promoter is set forth in SEQ ID NO: 9, and the ORF of PT is set forth in SEQ ID NO: 10. The nucleic acid sequences of the (i) hexanoyl-CoA synthetase (AAE1-1) promoter, (ii) hexanoyl-CoA synthetase (AAE1-1') promoter: (iii) hexanoyl-CoA synthetase (AAE3) promoter, and (iv) hexanoyl-CoA synthetase (AAE12) promoter are set forth in SEQ ID NOs: 11, 12, 13, and 14, respectively, and the ORF of hexanoyl-CoA (AAE-1) is set forth in SEQ ID NO: 15. The nucleic acid sequences of the (i) CBDA synthase (CBDAS) promoter, (ii) CBDAS synthase 1 (CBDAS1) promoter, (iii) CBDA synthase (CBDAS) 20800 promoter, and (iv) CBDA synthase (CBDAS) 20800' promoter are set forth in SEQ ID NOs: 16, 17, 18, and 19, respectively, and the nucleic acid sequence of the ORF of CBDA synthase (CBDAS) is set forth in SEQ ID NO: 20. The nucleic acid sequences of (i) THCA synthase (THCAS) 19603 promoter, (ii) THCA synthase (THCAS) 19603' promoter, (iii) THCA synthase (THCAS) 50320 promoter, (iv) THCA synthase (THCAS) 50320' promoter, (v) THCA synthase (THCAS) 1330 promoter, and (vi) THCA synthase (THCAS) 1330' promoter are set forth in SEQ ID NOs: 21, 22, 23, 24, 25, and 26, respectively, and the ORF of THCAS is set forth in SEQ ID NO: 27. The nucleic acid sequence of the CBCA synthase (CBCAS) 3498 promoter is set forth in SEQ ID NO: 28, the nucleic acid sequence of the CBCA synthase (CBCAS) 3498' promoter is set forth in SEQ ID NO: 29, and the ORF of CBCA synthase (CBCAS) is set forth in SEQ ID NO: 30.

The present technology also relates to the discovery of nucleic acid sequences for a "cannabinoid on" or "CANON" promoter fragment that is sufficient to direct trichome specific expression. The nucleic acid sequence for the CANON fragment that is sufficient to direct trichome specific expression in glandular trichomes is set forth in SEQ ID NO: 31. The nucleic acid sequence for the 4×CANON fragment synthetic promoter that comprises four copies of the consensus CANON fragment is set forth in SEQ ID NO: 33.

Given the known cytotoxic effects of cannabinoids such as THC on plant cells, the expression of genes driving their production under a strong ubiquitous promoter, like the Cauliflower Mosaic Virus (CaMV) 35S, may lead to the perturbation of metabolic pathways in the whole plant and may have deleterious consequences on plant development and physiology. Thus, trichomes, as distinct entities with restricted communication to the rest of plant, represent a potential target for metabolic engineering.

Accordingly, in some embodiments, the present technology provides previously undiscovered trichome specific promoters from cannabinoid biosynthesis genes or biologically active fragments thereof that may be used to genetically manipulate the synthesis of cannabinoids (e.g., THC, CBD, CBC. CBG) in host plants, such as C. sativa, plants of the family Solanaceae, and other plant families and species that do not naturally produce cannabinoids.

II. Definitions

All technical terms employed in this specification are commonly used in biochemistry, molecular biology and agriculture; hence, they are understood by those skilled in the field to which the present technology belongs. Those technical terms can be found, for example in: *Molecular Cloning: A Laboratory Manual* 3rd ed., vol. 1-3, ed. Sambrook and Russel (Cold Spring Harbor Laboratory Press, Cold Spring Harbor, N.Y., 2001); *Current Protocols In Molecular Biology*, ed. Ausubel et al. (Greene Publishing Associates and Wiley-Interscience, New York, 1988) (including periodic updates): *Short Protocols In Molecular Biology: A Compendium Of Methods From Current Protocols In Molecular Biology* 5th ed., vol. 1-2, ed. Ausubel et al. (John Wiley & Sons, Inc., 2002); Genome Analysis: A Laboratory Manual, vol. 1-2, ed. Green et al. (Cold Spring Harbor Laboratory Press, Cold Spring Harbor, N.Y., 1997). Methodology involving plant biology techniques are described here and also are described in detail in treatises such as *Methods In Plant Molecular Biology: A Laboratory Course Manual*, ed. Maliga et al. (Cold Spring Harbor Laboratory Press, Cold Spring Harbor, N.Y., 1995).

A "chimeric nucleic acid" comprises a coding sequence or fragment thereof linked to a nucleotide sequence that is different from the nucleotide sequence with which it is associated in cells in which the coding sequence occurs naturally.

The terms "encoding" and "coding" refer to the process by which a gene, through the mechanisms of transcription and translation, provides information to a cell from which a series of amino acids can be assembled into a specific amino acid sequence to produce an active enzyme. Because of the degeneracy of the genetic code, certain base changes in DNA sequence do not change the amino acid sequence of a protein.

"Endogenous nucleic acid" or "endogenous sequence" is "native" to, i.e., indigenous to, the plant or organism that is to be genetically engineered. It refers to a nucleic acid, gene, polynucleotide, DNA, RNA, mRNA, or cDNA molecule that is present in the genome of a plant or organism that is to be genetically engineered.

"Exogenous nucleic acid" refers to a nucleic acid, DNA or RNA, which has been introduced into a cell (or the cell's ancestor) through the efforts of humans. Such exogenous nucleic acid may be a copy of a sequence which is naturally found in the cell into which it was introduced, or fragments thereof.

As used herein, "expression" denotes the production of an RNA product through transcription of a gene or the production of the polypeptide product encoded by a nucleotide sequence. "Overexpression" or "up-regulation" is used to indicate that expression of a particular gene sequence or variant thereof, in a cell or plant, including all progeny plants derived thereof, has been increased by genetic engineering, relative to a control cell or plant.

"Genetic engineering" encompasses any methodology for introducing a nucleic acid or specific mutation into a host organism. For example, a plant is genetically engineered when it is transformed with a polynucleotide sequence that suppresses expression of a gene, such that expression of a target gene is reduced compared to a control plant. In the present context, "genetically engineered" includes transgenic plants and plant cells. A genetically engineered plant or plant cell may be the product of any native approach (i.e., involving no foreign nucleotide sequences), implemented by introducing only nucleic acid sequences derived from the host plant species or from a sexually compatible plant species. See. e.g., U.S. Patent Application No. 2004/0107455.

"Heterologous nucleic acid" or "homologous nucleic acid" refer to the relationship between a nucleic acid or amino acid sequence and its host cell or organism, especially in the context of transgenic organisms. A homologous sequence is naturally found in the host species (e.g., a *cannabis* plant transformed with a *cannabis* gene), while a heterologous sequence is not naturally found in the host cell (e.g., a tobacco plant transformed with a sequence from *cannabis* plants). Such heterologous nucleic acids may comprise segments that are a copy of a sequence that is naturally found in the cell into which it has been introduced, or fragments thereof. Depending on the context, the term "homolog" or "homologous" may alternatively refer to sequences which are descendent from a common ancestral sequence (e.g., they may be orthologs).

"Increasing," "decreasing," "modulating," "altering," or the like refer to comparison to a similar variety, strain, or cell grown under similar conditions but without the modification resulting in the increase, decrease, modulation, or alteration. In some cases, this may be a non-transformed control, a mock transformed control, or a vector-transformed control.

By "isolated nucleic acid molecule" is intended a nucleic acid molecule, DNA, or RNA, which has been removed from its native environment. For example, recombinant DNA molecules contained in a DNA construct are considered isolated for the purposes of the present technology. Further examples of isolated DNA molecules include recombinant DNA molecules maintained in heterologous host cells or DNA molecules that are purified, partially or substantially, in solution. Isolated RNA molecules include in vitro RNA transcripts of the DNA molecules of the present technology. Isolated nucleic acid molecules, according to the present technology, further include such molecules produced synthetically.

"Plant" is a term that encompasses whole plants, plant organs (e.g., leaves, stems, roots, etc.), seeds, differentiated or undifferentiated plant cells, and progeny of the same. Plant material includes without limitation seeds, suspension cultures, embryos, meristematic regions, callus tissues, leaves, roots, shoots, stems, fruit, gametophytes, sporophytes, pollen, and microspores.

"Plant cell culture" means cultures of plant units such as, for example, protoplasts, cell culture cells, cells in plant tissues, pollen, pollen tubes, ovules, embryo sacs, zygotes, and embryos at various stages of development. In some embodiments of the present technology, a transgenic tissue culture or transgenic plant cell culture is provided, wherein the transgenic tissue or cell culture comprises a nucleic acid molecule of the present technology.

"Promoter" connotes a region of DNA upstream from the start of transcription that is involved in recognition and binding of RNA polymerase and other proteins to initiate transcription. A "constitutive promoter" is one that is active throughout the life of the plant and under most environmental conditions. Tissue-specific, tissue-preferred, cell type-specific, and inducible promoters constitute the class of "non-constitutive promoters." A "trichome specific promoter" is a promoter that preferentially directs expression of an operably linked gene in trichome tissue, as compared to expression in the root, leaf, stem, or other tissues of the plant. "Operably linked" refers to a functional linkage between a promoter and a second sequence, where the promoter sequence initiates and mediates transcription of the DNA sequence corresponding to the second sequence. In general, "operably linked" means that the nucleic acid sequences being linked are contiguous.

"Sequence identity" or "identity" in the context of two polynucleotide (nucleic acid) or polypeptide sequences includes reference to the residues in the two sequences that are the same when aligned for maximum correspondence over a specified region. When percentage of sequence identity is used in reference to proteins it is recognized that residue positions which are not identical often differ by conservative amino acid substitutions, where amino acid residues are substituted for other amino acid residues with similar chemical properties, such as charge and hydrophobicity, and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity." Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, for example, according to the algorithm of Meyers & Miller, *Computer Applic. Biol. Sci.* 4: 11-17 (1988), as implemented in the program PC/GENE (Intelligenetics, Mountain View, Calif. USA).

Use in this description of a percentage of sequence identity denotes a value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The terms "suppression" or "down-regulation" are used synonymously to indicate that expression of a particular gene sequence variant thereof, in a cell or plant, including all progeny plants derived thereof, has been reduced by genetic engineering, relative to a control cell or plant.

"Trichome" encompasses herein different types of trichomes, both glandular trichomes and/or non-glandular trichomes.

"Trichome cells" refers to the cells making up the trichome structure, such as the gland, or secretory cells, base cells and stalk, or stripe cells, extra-cellular cavity and cuticle cells. Trichomes can also consist of one single cell.

"*Cannabis*" or "*cannabis* plant" refers to any species in the *Cannabis* genus that produces cannabinoids, such as *Cannabis sativa* and interspecific hybrids thereof.

A "variant" is a nucleotide or amino acid sequence that deviates from the standard, or given, nucleotide or amino acid sequence of a particular gene or polypeptide. The terms "isoform," "isotype," and "analog" also refer to "variant" forms of a nucleotide or an amino acid sequence. An amino acid sequence that is altered by the addition, removal, or substitution of one or more amino acids, or a change in nucleotide sequence, may be considered a variant sequence. A polypeptide variant may have "conservative" changes, wherein a substituted amino acid has similar structural or chemical properties, e.g., replacement of leucine with isoleucine. A polypeptide variant may have "nonconservative" changes, e.g., replacement of a glycine with a tryptophan. Analogous minor variations may also include amino acid deletions or insertions, or both. Guidance in determining which amino acid residues may be substituted, inserted, or deleted may be found using computer programs well known in the art such as Vector NTI Suite (InforMax, MD) software. Variant may also refer to a "shuffled gene" such as those described in Maxygen-assigned patents (see, e.g., U.S. Pat. No. 6,602,986).

As used herein, the term "about" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

The term "biologically active fragments" or "functional fragments" or "fragments having promoter activity" refer to nucleic acid fragments which are capable of conferring transcription in one or more trichome types and/or one or more trichome cells found on one or more different types of plant tissues and organs. Biologically active fragments confer trichome specific and/or at least trichome preferred expression, and they preferably have at least a similar strength (or higher strength) as the promoter of SEQ ID NOs: 1, 3, 5, 7, 9, or 11-15. This can be tested by transforming a plant with such a fragment, preferably operably linked to a reporter gene, and assaying the promoter activity qualitatively (spatio-temporal transcription) and/or quantitatively in trichomes. In some embodiments, the strength of the promoter and/or promoter fragments of the present technology is quantitatively identical to, or higher than, that of the CaMV 35S promoter when measured in the glandular trichome. In some embodiments, a biologically active fragment of a trichome promoter described herein can be about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% of the full length sequence nucleic acid sequence for the promoter. In other embodiments, a biologically active nucleic acid fragment of a trichome promoter described herein can be, for example, at least about 10 contiguous nucleic acids. In yet other embodiments, the biologically active nucleic acid fragment of a trichome promoter described herein can be (1) about 10 contiguous nucleic acids up to about 554 contiguous nucleic acids for the OLS promoter (e.g., SEQ ID NO: 1); (2) about 10 contiguous nucleic acids up to about 550 contiguous nucleic acids for the OLS1 promoter (SEQ ID NO: 2); (3) about 10 contiguous nucleic acids up to about 558 contiguous nucleic acids for the OLS2 promoter (SEQ ID NO: 3); (4) about 10 contiguous nucleic acids up to about 996 contiguous nucleic acids for the OAC promoter (e.g., SEQ ID NO: 5); (5) about 10 contiguous nucleic acids up to about 992 contiguous nucleic acids for the OAC1 promoter (e.g., SEQ ID NO: 6); (6) about 10 contiguous nucleic acids up to about 1361 contiguous nucleic acids for the PT promoter (e.g., SEQ ID NO: 8); (7) about 10 contiguous nucleic acids up to about 1357 contiguous nucleic acids for the PT1 promoter (e.g., SEQ ID NO: 9); (8) about 10 contiguous nucleic acids up to about 805 contiguous nucleic acids for the AAE1-1 promoter (e.g., SEQ ID NO: 11); (9) about 10 contiguous nucleic acids up to about 800 contiguous nucleic acids for the AAE1-1' promoter (e.g., SEQ ID NO: 12); (10) about 10 contiguous nucleic acids up to about 1000 contiguous nucleic acids for the AAE3 promoter (e.g., SEQ ID NO: 13); (11) about 10 contiguous nucleic acids up to about 869 contiguous nucleic acids for the AAE12 promoter (e.g., SEQ ID NO: 14): (12) about 10 contiguous nucleic acids up to about 420 contiguous nucleic acids for the CBDA synthase promoter (e.g., SEQ ID NO: 16): (13) about 10 contiguous nucleic acids up to about 416 contiguous nucleic acids for the CBDAS1 promoter (e.g., SEQ ID NO: 17); (14) about 10 contiguous nucleic acids up to about 535 contiguous nucleic acids for the CBDAS 20800 promoter (e.g., SEQ ID NO: 18): (15) about 10 contiguous nucleic acids up to about 531 contiguous nucleic acids for the CBDAS 20800'-promoter (e.g., SEQ ID NO: 19); (16) about 10 contiguous nucleic acids up to about 800 contiguous nucleic acids for the THCAS 19603 promoter (e.g., SEQ ID NO: 21); (17) about 10 contiguous nucleic acids up to about 796 contiguous nucleic acids for the THCAS 19603' promoter (e.g., SEQ ID NO: 22); (18) about 10 contiguous nucleic acids up to about 796 contiguous nucleic acids for the THCAS 50320 promoter (e.g., SEQ ID NO: 23); (19) about 10 contiguous nucleic acids up to about 792 contiguous nucleic acids for the THCAS 50320' promoter (e.g., SEQ ID NO: 24); (20) about 10 contiguous nucleic acids up to about 720 contiguous nucleic acids for the THCAS 1330 promoter (e.g., SEQ ID NO: 25); (21) about 10 contiguous nucleic acids up to about 716 contiguous nucleic acids for the THCAS 1330' promoter (e.g., SEQ ID NO: 26): (22) about 10 contiguous nucleic acids up to about 804 contiguous nucleic acids for the CBCAS 3498 promoter (e.g., SEQ ID NO: 28): or (23) about 10 contiguous nucleic acids up to about 800 contiguous nucleic acids for the CBCAS 3498' promoter (e.g., SEQ ID NO: 29). In yet other embodiments, the biologically active fragment of the trichome promoter can be any value of contiguous nucleic acids in between these two amounts, such as but not limited to about 20, about 30, about 40, about 50, about 60, about 70, about 80, about 90, about 100, about 110, about 120, about 130, about 140, about 150, about 160, about 170, about 180, about 190, about 200, about 250, about 300, about 350, about 400, about 450, about 500, about 550, about 60, about 650, about 700, about 750, about 800, about 850, about 900, about 950, about 1000, about 1050, about 1100, about 1150, about 1200, about 1250, or about 1300 contiguous nucleic acids.

III. Genetic Engineering of Host Cells and Organisms Using Trichome Specific Promoters A. Trichome Specific Promoters The disclosure of the present technology relates to the identification of twenty-three promoters, which are capable of regulating transcription of coding nucleic acid sequences operably linked thereto in trichome cells.

Accordingly, the present technology provides an isolated polynucleotide having a nucleic acid sequence that is at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99%, or 100% identical to a nucleic acid sequence described in any of SEQ ID NOs: 1-3, 5, 6, 8, 9, 11-14, 16-19, 21-26, 28, 29, and 31-33, wherein the nucleic acid sequence is capable of regulating transcription of coding nucleic acid sequences operably linked thereto in trichome cells. Differences between two nucleic acid sequences may occur at the 5' or 3' terminal positions of the reference nucleotide sequence or anywhere between those terminal positions, interspersed either individually among nucleotides in the reference sequence or in one or more contiguous groups within the reference sequence.

The present technology also includes biologically active "variants" of SEQ ID NOs: 1-3, 5, 6, 8, 9, 11-14, 16-19, 21-26, 28, 29, and 31-33, with one or more bases deleted, substituted, inserted, or added, wherein the nucleic acid sequence is capable of regulating transcription of coding nucleic acid sequences operably linked thereto in trichome cells. Variants of SEQ ID NOs: 1-3, 5, 6, 8, 9, 11-14, 16-19, 21-26, 28, 29, and 31-33, include nucleic acid sequences comprising at least about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more nucleic acid sequence identity to SEQ ID NOs: 1-3, 5, 6, 8, 9, 11-14, 16-19, 21-26, 28, 29, and 31-33, and which are trichome specific in their activity.

In some embodiments of the present technology, the polynucleotides (promoters) are modified to create variations in the molecule sequences such as to enhance their promoting activities, using methods known in the art, such as PCR-based DNA modification, or standard mutagenesis techniques, or by chemically synthesizing the modified polynucleotides.

Accordingly, the sequences set forth in SEQ ID NOs: 1-3, 5, 6, 8, 9, 11-14, 16-19, 21-26, 28, 29, and 31-33 may be truncated or deleted and still retain the capacity of directing the transcription of an operably linked nucleic acid sequence in trichomes. The minimal length of a promoter region can be determined by systematically removing sequences from the 5' and 3'-ends of the isolated polynucleotide by standard techniques known in the art, including but not limited to removal of restriction enzyme fragments or digestion with nucleases.

Trichome specific promoters of the present technology may also be used for expressing a nucleic acid that will decrease or inhibit expression of a native gene in the plant. Such nucleic acids may encode antisense nucleic acids, ribozymes, sense suppression agents, or other products that inhibit expression of a native gene.

The trichome specific promoters of the present technology may also be used to express proteins or peptides in "molecular farming" applications. Such proteins or peptides include but are not limited to industrial enzymes, antibodies, therapeutic agents, and nutritional products.

In some embodiments, novel hybrid promoters can be designed or engineered by a number of methods. Many promoters contain upstream sequences which activate, enhance, or define the strength and/or specificity of the promoter. See, e.g., Atchison, *Ann. Rev. Cell Biol.* 4:127 (1988). T-DNA genes, for example contain "TATA" boxes defining the site of transcription initiation and other upstream elements located upstream of the transcription initiation site modulate transcription levels.

B. Cannabinoid on (CANON) Fragment for Trichome Specific Expression

In some embodiments, the disclosure of the present technology also relates to the identification of a nucleic acid molecule termed the "Cannabinoid On" or "CANON" fragment that is sufficient for directing trichome specific expression of coding nucleic acid sequences operably linked thereto.

The 171-base pair CANON fragment (SEQ ID NO: 31) is shown below in Table 1. The consensus CANON fragment (highlighted) is shown together with the putative TATA box (bold underline), 5' UTR, and start codon ("atg" in bold underline) as SEQ ID NO: 32 in Table 1. The consensus is derived from the trichome specific promoters from THCA synthases 19603, 1330, and 50320, CBCA synthase 3498, and CBDA synthase 20800. The 171-base pair CANON fragment (SEQ ID NO: 31) is sufficient to direct trichome specific expression in glandular trichomes of tobacco (and cannabis).

A nucleic acid sequence comprising four copies of the CANON fragment in front of one copy of the minimal promoter (i.e., TATA Box, start of transcription, and first ATG) termed "4×CANON fragment synthetic promoter" is also shown as SEQ ID NO: 33 in

TABLE 1

The first CANON fragment of SEQ ID NO: 33 is shown in bold, followed by a second fragment shown in underline, followed by a third fragment in bold, and a fourth fragment in underline.
Table 1. CANON fragment sequences.

```
Cannabinoid On ("CANON") fragment (171 bp)
atgatgccaaactattcaatgtacaatgtacatttattttaataagggc
btcctcccactaacaaaggtgcctaattttttgtgaactttttttaccac
atgtgactatttaatgactatcaaattataaaatatttaagtcaatttct
ttgcccccactccaatatataatgt (SEQ ID NO: 31)

CANON fragment with putative TATA Box,
5' UTR, and start codon (232 bp)
atgatgccaaactattcaatgtacaatgtacatttattttaataagggc
ttcacctaacaaaggtgcctaattttttgtgaactttttttaccacatgt
gactatttaatgactatcaaattataaaatatttaagtcaatttctttgc
ccccactccaatatataatgttataaataggataattctcaattcatagt
attcaaaaatcattaggactaaagaaaaatg (SEQ ID NO: 32)

4 × CANON fragment synthetic promoter 709 bp)
atgatgccaaactattcaatgtacaatgtacatttattttaataagggc
ttcacctaacaaaggtgcctaattttttgtgaactttttttaccacatgt
gactatttaatgactatcaaattataaaatatttaagtcaatttctttgc
ccccactccatgatgccaaactattcaatgtacaatgtacatttattttt
aataagggcttcacctaacaaaggtgcctaattttttgtgaactttttttt
accacatgtgactatttaatgactatcaaattataaaatatttaagtcaa
tttctttgcccccactccatgatgccaaactattcaatgtacaatgtaca
tttattttaataagggcttcacctaacaaaggtgcctaattttttgtgaa
cttttttttaccacatgtgactatttaatgactatcaaattataaaatat
ttaagtcaatttctttgcccccactccatgatgccaaactattcaatgt
acaatgtacatttattttaataagggattcacctaacaaaggtgcctaa
ttttgtgaactttttttttaccacatgtgactatttaatgactatcaaat
tataaaatatttaagtcaatttctttgcccccactccaatatataatgtt
ataaatagctataattctcaattcatagtaattcaaaaatcattaggact
aaacgaaaaatg (SEQ ID NO: 33)
```

The CANON fragment is sufficient to direct trichome specific expression in a gain-of-function promoter. Without wishing to be bound by theory, it is believed that the CANON fragment is responsible for the trichome specific expression of a number of cannabinoid biosynthetic enzyme genes including THCA, CBDA, and CBCA synthases.

C. Nucleic Acid Constructs

In some embodiments, the trichome specific promoter sequences and CANON fragments of the present technology, or biologically active fragments thereof, can be incorporated into nucleic acid constructs, such as expression constructs (i.e., expression vectors), which can be introduced and replicate in a host cell, such as plant trichome cell. Such nucleic acid constructs may include a heterologous nucleic acid operably linked to any of the promoter sequences or CANON fragments of the present technology. Thus, in some embodiments, the present technology provides the use of any of the promoters or CANON fragments set forth in SEQ ID NOs: 1-3, 5, 6, 8, 9, 11-14, 16-19, 21-26, 28, 29, and 31-33, or biologically active fragments thereof, for the expression of homologous or heterologous nucleic acid sequences in a recombinant cell or organism, such as a plant cell or plant. In some embodiments, this use comprises operably linking any of the promoters or CANON fragments set forth in SEQ ID NOs: 1-3, 5, 6, 8, 9, 11-14, 16-19, 21-26, 28, 29, and 31-33, or biologically active fragments thereof, to a homologous or heterologous nucleic acid sequence to form a nucleic acid construct and transforming a host, such as a plant or plant cell. In some embodiments, various genes that encode enzymes involved in biosynthetic pathways for the production of cannabinoids (e.g., at least one of the nucleic acid sequences set forth in SEQ ID NOs: 4, 7, 10, 15, 20, 27, or 30) can be suitable as transgenes that can be operably linked to a trichome specific promoter or CANON fragment of the present technology. In some embodiments, the nucleic acid constructs of the present technology modulate the expression of one or more proteins that regulate cannabinoid biosynthesis. In some embodiments, the nucleic acid constructs of the present technology can be used to modulate the expression of cannabinoids or other compounds (e.g., terpenes) in trichome cells.

In some embodiments, an expression vector comprises a promoter or CANON fragment comprising a nucleic acid sequence selected from the group consisting of SEQ ID NOs: 1-3, 5, 6, 8, 9, 11-14, 16-19, 21-26, 28, 29, and 31-33, or a biologically active fragment thereof, operably linked to the cDNA encoding a polypeptide, such as one or more of olivetol synthase (OLS), olivetolic acid cyclase (OAC), aromatic pyrenyltransferase (PT), hexanoyl-CoA synthetase (AEE1-1), CBDA synthase, CBCA synthase, and THCA synthase. In another embodiment, a plant cell line comprises an expression vector comprising a promoter or CANON fragment comprising a nucleic acid sequence selected from the group consisting of SEQ ID NOs: 1-3, 5, 6, 8, 9, 11-14, 16-19, 21-26, 28, 29, and 31-33, or a biologically active fragment thereof, operably linked to the cDNA encoding a polypeptide, such as one or more of olivetol synthase (OLS), olivetolic acid cyclase (OAC), aromatic pyrenyltransferase (PT), hexanoyl-CoA synthetase (AEE1-1), CBDA synthase, CBCA synthase, and THCA synthase. In another embodiment, a transgenic plant comprises an expression vector comprising a promoter or CANON fragment comprising a nucleic acid sequence selected from the group consisting of SEQ ID NOs: 1-3, 5, 6, 8, 9, 11-14, 16-19, 21-26, 28, 29, and 31-33, or a biologically active fragment thereof, operably linked to the cDNA encoding a polypeptide, such as one or more of olivetol synthase (OLS), olivetolic acid cyclase (OAC), aromatic pyrenyltransferase (PT), hexanoyl-CoA synthetase (AEE1-1), CBDA synthase, CBCA synthase, and THCA synthase. In another embodiment, methods for genetically modulating the production of cannabinoids are provided, comprising: introducing an expression vector comprising a promoter or CANON fragment comprising a nucleic acid sequence selected from the group consisting of SEQ ID NOs: 1-3, 5, 6, 8, 9, 11-14, 16-19, 21-26, 28, 29, and 31-33, or a biologically active fragment thereof, operably linked to the cDNA encoding a polypeptide, such as one or more of olivetol synthase (OLS), olivetolic acid cyclase (OAC), aromatic pyrenyltransferase (PT), hexanoyl-CoA synthetase (AEE1-1), CBDA synthase, CBCA synthase, and THCA synthase.

In another embodiment, an expression vector comprises one or more promoters or CANON fragments comprising a nucleic acid sequence selected from the group consisting of SEQ ID NOs: 1-3, 5, 6, 8, 9, 11-14, 16-19, 21-26, 28, 29, and 31-33, or a biologically active fragment thereof, operably linked to cDNA encoding a polypeptide, such as one or more of olivetol synthase (OLS), olivetolic acid cyclase (OAC), aromatic pyrenyltransferase (PT), hexanoyl-CoA synthetase (AEE1-1), CBDA synthase, CBCA synthase, and THCA synthase. In another embodiment, a plant cell line comprises one or more promoters comprising a nucleic acid sequence selected from the group consisting of SEQ ID NOs: 1-3, 5, 6, 8, 9, 11-14, 16-19, 21-26, 28, 29, and 31-33, or a biologically active fragment thereof, operably linked to cDNA encoding a polypeptide, such as one or more of olivetol synthase (OLS), olivetolic acid cyclase (OAC), aromatic pyrenyltransferase (PT), hexanoyl-CoA synthetase (AEE1-1), CBDA synthase, CBCA synthase, and THCA synthase. In another embodiment, a transgenic plant comprises one or more promoters or CANON fragments comprising a nucleic acid sequence selected from the group consisting of SEQ ID NOs: 1-3, 5, 6, 8, 9, 11-14, 16-19, 21-26, 28, 29, and 31-33, or a biologically active fragment thereof, operably linked to cDNA encoding a polypeptide, such as one or more of olivetol synthase (OLS), olivetolic acid cyclase (OAC), aromatic pyrenyltransferase (PT), hexanoyl-CoA synthetase (AEE1-1), CBDA synthase, CBCA synthase, and THCA synthase. In another embodiment, methods for genetically modulating the production level of cannabinoids are provided, comprising introducing into a host cell an expression vector comprising one or more promoters or CANON fragments, comprising a nucleic acid sequence selected from the group consisting of SEQ ID NOs: 1-3, 5, 6, 8, 9, 11-14, 16-19, 21-26, 28, 29, and 31-33, or a biologically active fragment thereof, operably linked to cDNA encoding a polypeptide, such as one or more of olivetol synthase (OLS), olivetolic acid cyclase (OAC), aromatic pyrenyltransferase (PT), hexanoyl-CoA synthetase (AEE1-1), CBDA synthase, CBCA synthase, and THCA synthase.

Constructs may be comprised within a vector, such as an expression vector adapted for expression in an appropriate host (plant) cell. It will be appreciated that any vector which is capable of producing a plant comprising the introduced DNA sequence will be sufficient.

Suitable vectors are well known to those skilled in the art and are described in general technical references such as Pouwels et al., *Cloning Vectors. A Laboratory Manual*, Elsevier, Amsterdam (1986). Vectors for plant transformation have been described (see, e.g., Schardl et al., *Gene* 61:1-14 (1987)). In some embodiments, the nucleic acid construct is a plasmid vector, or a binary vector. Examples of suitable vectors include the Ti plasmid vectors.

Recombinant nucleic acid constructs (e.g., expression vectors) capable of introducing nucleotide sequences or chimeric genes under the control of a trichome specific regulatory sequence (e.g., promoter, CANON fragment) may be made using standard techniques generally known in the art. To generate a chimeric gene, an expression vector generally comprises, operably linked in the 5' to 3' direction, a trichome specific promoter sequence or CANON sequence that directs the transcription of a downstream homologous or heterologous nucleic acid sequence, and optionally followed by a 3' untranslated nucleic acid region (3'-UTR) that encodes a polyadenylation signal which functions in plant cells to cause the termination of transcription and the addition of polyadenylate nucleotides to the 3' end of the mRNA encoding the protein. The homologous or heterologous nucleic acid sequence may be a sequence encoding a protein or peptide or it may be a sequence that is transcribed into an active RNA molecule, such as a sense and/or antisense RNA suitable for silencing a gene or gene family in the host cell or organism. Expression vectors also generally contain a selectable marker. Typical 5' to 3' regulatory sequences include a transcription initiation site, a ribosome binding site, an RNA processing signal, a transcription termination site, and/or polyadenylation signal.

In some embodiments, the expression vectors of the present technology may contain termination sequences, which are positioned downstream of the nucleic acid molecules of the present technology, such that transcription of mRNA is terminated, and polyA sequences added. Exemplary terminators include *Agrobacterium tumefaciens* nopaline synthase terminator (Tnos), *Agrobacterium tumefaciens* mannopine synthase terminator (Tmas), and the CaMV 35S terminator (T35S). Termination regions include the pea ribulose bisphosphate carboxylase small subunit termination region (TrbcS) or the Tnos termination region. The expression vector also may contain enhancers, start codons, splicing signal sequences, and targeting sequences.

In some embodiments, the expression vectors of the present technology may contain a selection marker by which transformed cells can be identified in culture. The marker may be associated with the heterologous nucleic acid molecule, i.e., the gene operably linked to a promoter. As used herein, the term "marker" refers to a gene encoding a trait or a phenotype that permits the selection of, or the screening for, a plant or cell containing the marker. In plants, for example, the marker gene will encode antibiotic or herbicide resistance. This allows for selection of transformed cells from among cells that are not transformed or transfected.

Examples of suitable selectable markers include but are not limited to adenosine deaminase, dihydrofolate reductase, hygromycin-B-phosphotransferase, thymidine kinase, xanthine-guanine phospho-ribosyltransferase, glyphosate and glufosinate resistance, and amino-glycoside 3'-O-phosphotransferase (kanamycin, neomycin and G418 resistance). These markers may include resistance to G418, hygromycin, bleomycin, kanamycin, and gentamicin. The construct may also contain the selectable marker gene bar that confers resistance to herbicidal phosphinothricin analogs like ammonium gluphosinate. See, e.g., Thompson et al., *EMBO J.* 9:2519-23 (1987)). Other suitable selection markers known in the art may also be used.

Visible markers such as green florescent protein (GFP) may be used. Methods for identifying or selecting transformed plants based on the control of cell division have also been described. See, e.g., WO 2000/052168 and WO 2001/059086.

Replication sequences, of bacterial or viral origin, may also be included to allow the vector to be cloned in a bacterial or phage host. Preferably, a broad host range prokaryotic origin of replication is used. A selectable marker for bacteria may be included to allow selection of bacterial cells bearing the desired construct. Suitable prokaryotic selectable markers also include resistance to antibiotics such as kanamycin or tetracycline.

Other nucleic acid sequences encoding additional functions may also be present in the vector, as is known in the art. For example, when *Agrobacterium* is the host, T-DNA sequences may be included to facilitate the subsequent transfer to and incorporation into plant chromosomes.

Whether a nucleic acid sequence of present technology or biologically active fragment thereof is capable of conferring transcription specifically in trichomes and whether the activity is "strong," can be determined using various methods. Qualitative methods (e.g., histological GUS (β-glucuronidase) staining) are used to determine the spatio-temporal activity of the promoter or CANON fragment (i.e., whether the promoter or CANON fragment is active in a certain tissue or organ (e.g., trichomes, or under certain environmental/developmental conditions). Quantitative methods (e.g., fluorometric GUS assays) also quantify the level of activity compared to controls. Suitable controls include, but are not limited to, plants transformed with empty vectors (negative controls) or transformed with constructs comprising other promoters, such as the *Arabidopsis* CER6 promoter, which is active in the epidermis and trichomes of *Nicotiana tabacum*.

To test or quantify the activity of a promoter or CANON fragment of the present technology, a nucleic acid sequence as set forth in SEQ ID NOs: 1-3, 5, 6, 8, 9, 11-14, 16-19, 21-26, 28, 29, or 31-33, or biologically active fragments thereof, may be operably linked to a known nucleic acid sequence (e.g., a reporter gene such as gusA, or any gene encoding a specific protein) and may be used to transform a plant cell using known methods. The activity of the promoter or CANON fragment can, for example, be assayed (and optionally quantified) by detecting the level of RNA transcripts of the downstream nucleic acid sequence in trichome cells by quantitative RT-PCR or other PCR-based methods. Alternatively, the reporter protein or activity of the reporter protein may be assayed and quantified, by, for example a fluorometric GUS assay if the reporter gene is the gus gene.

In some embodiments, the promoters of the present technology can be used to drive expression of a heterologous nucleic acid of interest in trichome cells. The heterologous nucleic acid can encode any man-made recombinant or naturally occurring or protein, such as the cannabinoid biosynthetic pathway enzymes olivetol synthase (OLS), olivetolic acid cyclase (OAC), aromatic prenyltransferase (PT), hexanoyl-CoA synthetase (AAE1-1), CBDA synthase, THCA synthase, or CBCA synthase as set forth in SEQ ID NOs: 4, 7, 10, 15, 20, 27, and 30, respectively.

D. Host Plants and Cells and Plant Regeneration

The nucleic acid construct of the present technology can be utilized to transform a host cell, such as a plant cell. In some embodiments, the nucleic acid construct of the present technology is used to transform at least a portion of the cells of a plant. These expression vectors can be transiently introduced into host plant cells or stably integrated into the genomes of host plant cells to generate transgenic plants by various methods known to persons skilled in the art.

Methods for introducing nucleic acid constructs into a cell or plant are well known in the art. Suitable methods for introducing nucleic acid constructs (e.g., expression vectors) into plant trichomes to generate transgenic plants include, but are not limited to, *Agrobacterium*-mediated transformation, particle gun delivery, microinjection, electroporation, polyethylene glycol-assisted protoplast transformation, and liposome-mediated transformation. Methods for transforming dicots primarily use *Agrobacterium tumefaciens*.

*Agrobacterium rhizogenes* may be used to produce transgenic hairy roots cultures of plants, including *cannabis* and tobacco, as described, for example, by Guillon et al., *Curr. Opin. Plant Biol.* 9:341-6 (2006). "Tobacco hairy roots" refers to tobacco roots that have T-DNA from an Ri plasmid of *Agrobacterium rhizogenes* integrated in the genome and grow in culture without supplementation of auxin and other phytohormones.

Additionally, plants maybe be transformed by *Rhizobium, Sinorhizobium*, or *Mesorhizobium* transformation. (Broothaerts et al., *Nature* 433: 629-633 (2005)).

After transformation of the plant cells or plant, those plant cells or plants into which the desired DNA has been incorporated may be selected by such methods as antibiotic resistance, herbicide resistance, tolerance to amino-acid analogues or using phenotypic markers.

The transgenic plants can be used in a conventional plant breeding scheme, such as crossing, selfing, or backcrossing, to produce additional transgenic plants containing the transgene.

Suitable host cells include plant cells. Any plant may be a suitable host, including monocotyledonous plants or dicotyledonous plants, such as, for example, maize/corn (*Zea* species, e.g., *Z. mays. Z. diploperennis* (chapule), *Zea luxurians* (Guatemalan teosinte), *Zea mays* subsp. *huehuetenangensis* (San Antonio Huista teosinte), *Z. mays* subsp. *mexicana* (Mexican teosinte), *Z. mays* subsp. *parviglumis* (Balsas teosinte), *Z. perennis* (perennial teosinte) and *Z. ramosa*, wheat (*Triticum* species), barley (e.g., *Hordeum vulgare*), oat (e.g., *Avena sativa*), sorghum (*Sorghum bicolor*), rye (*Secale cereale*), soybean (*Glycine* spp. e.g., *G. max*), cotton (*Gossypium* species, e.g., *G. hirsutum. G. barbadense*), *Brassica* spp. (e.g., *B. napus. B. juncea, B. oleracea, B. rapa*, etc.) sunflower (*Helianthus annus*), tobacco (*Nicotiana* species), alfalfa (*Medicago sativa*), rice (*Oryza* species, e.g., *O. sativa* indica cultivar-group or japonica cultivar-group), forage grasses, pearl millet (*Pennisetum* species. e.g., *P. glaucum*), tree species, vegetable species, such as *Lycopersicon* ssp (recently reclassified as belonging to the genus *Solanum*), e.g., tomato (*L. esculentum*, syn. *Solanum lycopersicum*) such as e.g., cherry tomato, var. *cerasiforme* or current tomato, var. *pimpinellifolium*) or tree tomato (*S. betaceum*, syn. *Cyphomandra betaceae*), potato (*Solanum tuberosum*) and other *Solanum* species, such as eggplant (*Solanum melongena*), pepino (*S. muricatum*), cocona (*S. sessiliflorum*) and naranjilla (*S. quitoense*); peppers (*Capsicum annuum, Capsicum frutescens*), pea (e.g., *Pisum sativum*), bean (e.g., *Phaseolus* species), carrot (*Daucus carona*), *Lactuca* species (such as *Lactuca sativa, Lactuca indica, Lactuca perennis*), cucumber (*Cucumis sativus*), melon (*Cucumis melo*), zucchini (*Cucurbita pepo*), squash (*Cucurbita maxima, Cucurbita pepo, Cucurbita mixta*), pumpkin (*Cucurbita pepo*), watermelon (*Citrullus lanatus* syn. *Citrullus vulgaris*), fleshy fruit species (grapes, peaches, plums, strawberry, mango, melon), ornamental species (e.g., Rose, *Petunia, Chrysanthemum*, Lily, Tulip, *Gerbera* species), woody trees (e.g., species of *Populus, Salix, Quercus, Eucayptus*), fibre species e.g., flax (*Linum usitatissimum*), and hemp (*Cannabis sativa*). In some embodiments, the plant is *Cannabis sativa*. In some embodiments, the plant is *Nicotiana tabacum*.

Thus, in some embodiments, the present technology contemplates the use of the trichome specific promoters and/or CANON fragments comprising the nucleic acid sequences set forth SEQ ID NOs: 1-3, 5, 6, 8, 9, 11-14, 16-19, 21-26, 28, 29, and 31-33, or biologically active fragments thereof, to genetically manipulate the synthesis of cannabinoids (e.g., THC, CBD, CBC) or other molecules in host plants, such as *C. sativa*, plants of the family *Solanaceae*, such as *N. tabacum*, and other plant families and species that do not naturally produce cannabinoids.

The present technology also contemplates cell culture systems (e.g., plant cell cultures, bacterial or fungal cell cultures, human or mammalian cell cultures, insect cell cultures) comprising genetically engineered cells transformed with the nucleic acid molecules described herein. In some embodiments, a cell culture comprising cells comprising a promoter or CANON fragment of the present technology is provided.

Various assays may be used to determine whether a plant cell shows a change in gene expression, for example, Northern blotting or quantitative reverse transcriptase PCR (RT-PCR). Whole transgenic plants may be regenerated from the transformed cell by conventional methods. Such transgenic plants may be propagated and self-pollinated to produce homozygous lines. Such plants produce seeds containing the genes for the introduced trait and can be grown to produce plants that will produce the selected phenotype.

To enhance the expression and/or accumulation of a molecule of interest in trichome cells and/or to facilitate purification of the molecule from trichome cells, methods to down-regulate at least one molecule endogenous to the plant trichomes can be employed. Trichomes are known to contain a number of compounds and metabolites that interfere with the production of other molecules in the trichome cells. These compounds and metabolites include, for example, proteases, polyphenol oxidase (PPO), polyphenols, ketones, terpenoids, and alkaloids. The down-regulation of such trichome components has been described. See, e.g., U.S. Pat. No. 7,498,428.

EXAMPLES

The following examples are provided by way of illustration only and not by way of limitation. Those of skill in the art will readily recognize a variety of non-critical parameters that could be changed or modified to yield essentially the same or similar results. The examples should in no way be construed as limiting the scope of the present technology, as defined by the appended claims.

Example 1: Identifying Trichome Specific Promoters

The nucleic acid sequences of the (i) olivetol synthase (OLS) promoter, (ii) OLS1 promoter, and (iii) OLS2 promoter are set forth in SEQ ID NOs: 1, 2, and 3, respectively, and the open reading frame (ORF) of OLS is set forth in SEQ ID NO: 4. The nucleic acid sequence of the olivetolic acid cyclase (OAC) promoter is set forth in SEQ ID NO: 5, the nucleic acid sequence of the OAC1 promoter is set forth in SEQ ID NO: 6, and the ORF of OAC is set forth in SEQ ID NO: 7. The nucleic acid sequence of aromatic prenyltransferase (PT) promoter is set forth in SEQ ID NO: 8, the nucleic acid sequence of the PT1 promoter is set forth in SEQ ID NO: 9, and the ORF of PT is set forth in SEQ ID NO: 10. The nucleic acid sequences of the (i) hexanoyl-CoA synthetase (AAE1-1) promoter, (ii) hexanoyl-CoA synthetase (AAE1-1') promoter; (iii) hexanoyl-CoA synthetase (AAE3) promoter, and (iv) hexanoyl-CoA synthetase (AAE12) promoter are set forth in SEQ ID NOs: 11, 12, 13, and 14, respectively, and the ORF of hexanoyl-CoA (AAE-1) is set forth in SEQ ID NO: 15. The nucleic acid sequences of the (i) CBDA synthase (CBDAS) promoter, (ii) CBDAS synthase 1 (CBDAS1) promoter, (iii) CBDA synthase (CBDAS) 20800 promoter, and (iv) CBDA synthase (CBDAS) 20800' promoter are set forth in SEQ ID NOs: 16, 17, 18, and 19, respectively, and the nucleic acid sequence of the ORF of CBDA synthase (CBDAS) is set forth in SEQ ID NO: 20. The nucleic acid sequences of (i) THCA synthase (THCAS) 19603 promoter, (ii) THCA synthase (THCAS) 19603' promoter, (iii) THCA synthase (THCAS) 50320 promoter, (iv) THCA synthase (THCAS) 50320' promoter, (v) THCA synthase (THCAS) 1330 promoter, and (vi) THCA synthase (THCAS) 1330' promoter are set forth in SEQ ID NOs: 21, 22, 23, 24, 25, and 26, respectively, and the ORF of THCAS is set forth in SEQ ID NO: 27. The nucleic acid sequence of the CBCA synthase (CBCAS) 3498 promoter is set forth in SEQ ID NO: 28, the nucleic acid sequence of the CBCA synthase (CBCAS) 3498' promoter is set forth in SEQ ID NO: 29, and the ORF of CBCA synthase (CBCAS) is set forth in SEQ ID NO: 30.

Trichome specific promoters were identified by searching the draft genome sequence of *Cannabis sativa* using the BLAT search facility with the coding regions of the biosynthetic enzyme genes in the cannabinoid biosynthetic pathway. For each genomic sequence hit, a gene prediction program was run (using the FGENESH program) to establish the first ATG. The start of transcription was then established by comparing the genomic sequence to the longest available cDNA sequences in the NCBI NR database. Both multiple sequence alignments (for the CBDA and THCA synthase genes) and querying the PLACE database established TATA Box regions. With the start codon, start of transcription, and TATA Box established, the location and sequence of the promoters was verified.

Example 2: Trichome Specific Promoters for Directing Cannabinoid Production in *Nicotiana tabacum*

Cannabinoids are synthesized and accumulated in *cannabis* trichomes. Olivetol synthase (OLS), olivetolic acid cyclase (OAC), aromatic prenyltransferase (PT), hexanoyl-CoA synthetase (AAE1-1), CBDA synthase, CBCA synthase, and THCA synthase are enzymes of the cannabinoid biosynthetic pathway. Accordingly, it is expected that the promoters for each of these enzymes will direct the expression of coding nucleic acids in trichome cells. This example demonstrates the use of the trichome specific promoters of the present technology, or biologically active fragments thereof, to express cannabinoid biosynthetic enzymes in plants and plant cells that do not naturally produce cannabinoids.

Methods

Vector constructs. Promoter sequences (SEQ ID NOs: 1-3, 5, 6, 8, 9, 11-14, 16-19, 21-26, 28, 29, or 31-33) are placed in front of a GUS-A marker in a vector adapted for expression in a *Nicotiana tabacum* cell, such as a Ti plasmid vector. The constructs are incorporated into *Agrobacterium tumafaciens* and used to transform *N. tabacum* according to methods known in the art. Constructs are transformed and regenerated under kanamycin selection and primary regenerants ($T_0$) are grown to seed.

As a control, a construct containing the tobacco NtCPS2 promoter is transformed into tobacco. The NtCPS2 promoter has been shown to be highly effective in directing trichome-specific expression in *N. tabacum* (Sallaud et al., *The Plant Journal* 72:1-17 (2012)).

Expression analysis. Quantitative and qualitative β-glucuronidase (GUS) activity analyses are performed on $T_1$ plants. Qualitative analysis of promoter activity is carrier out using histological GUS assays and by visualization of the Green Fluorescent Protein (GFP) using a fluorescence microscope. For GUS assays, various plant parts are incubated overnight at 37° C. in the presence of atmospheric oxygen with Xglue (5-Bromo-4-chloro-3-indolyl-β-D-glucuronide cyclohexylamine salt) substrate in phosphate buffer (1 mg/mL, $K_2HPO_4$, 10 μM, pH 7.2, 0.2% Triton X-100). The samples are de-stained by repeated washing with ethanol. Non-transgenic plants are used as negative controls. It is anticipated that trichomes of transgenic plants with OLS: GUS, OAC:GUS, PT:GUS, AAEE1-1:GUS, CBDAS:GUS, CBCAS:GUS, and THCAS:GUS will show bright blue trichomes whereas the non-trichome tissues of these transgenic plants and the trichomes of non-transgenic control plants will not be colored.

Quantitative analysis of promoter activity is carried out using a fluorometric GUS assay. Total protein samples are prepared from young leaf material: samples are prepared from pooled leaf pieces. Fresh leaf material is ground in PBS using metal beads followed by centrifugation and collection of the supernatant.

Results

Figure 3:
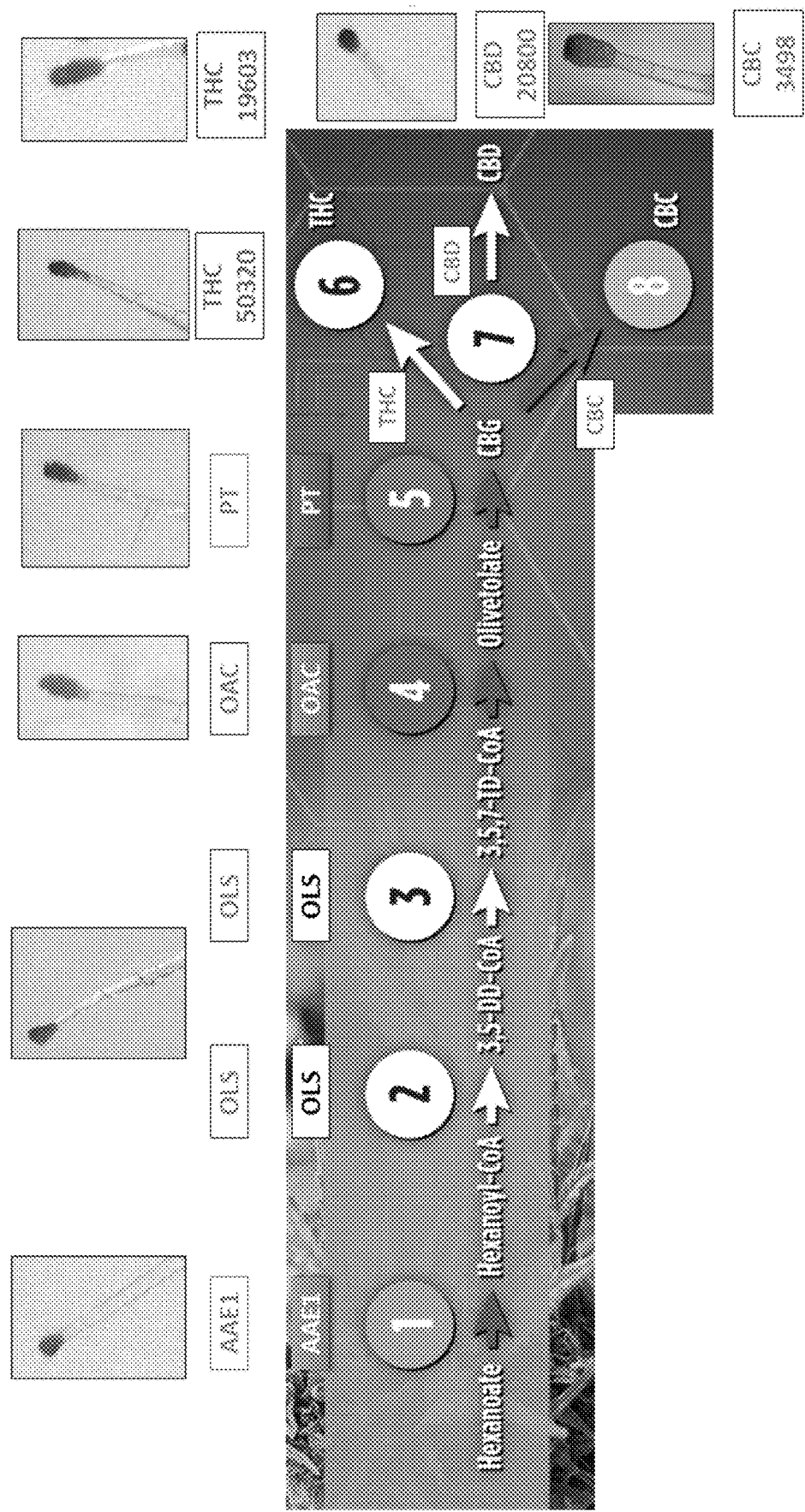
FIG. 3 shows trichome specific expression of promoters from the complete cannabinoid biosynthetic pathway in tobacco trichomes. Promoter activity is indicated by a blue color caused by activity of the GUS reporter gene. A representative promoter from every gene in the pathway shows trichome specific expression and therefore all promoters from genes in the pathway will direct expression in the trichomes.

Plants and plant cells genetically engineered with expression vectors comprising the promoters of the present technology, or biologically active fragments thereof, exhibit trichome specific transcriptional activity. As shown in FIG. 2B, trichomes of a transgenic plant transformed with CBDAS 20800:GUS show bright blue trichomes whereas the non-trichome tissues of the plant are not colored. Trichome specific expression for the other promoters in the cannabinoid biosynthetic pathway are qualitatively similar (FIG. 3). Results shown in FIG. 3 demonstrate the trichome specific expression of promoters from the complete cannabinoid biosynthetic pathway in tobacco trichomes. Accordingly, these results demonstrate that the promoters from the complete cannabinoid biosynthetic pathway as described herein are useful for preferentially directing expression of an operably linked gene in trichome tissue, as compared to expression in the root, leaf, stem, or other tissues of a plant. This trichome-specific expression will be a crucial tool for the manipulation of the biosynthesis of trichome-specific biochemical compounds such as the cytotoxic cannabinoids. In addition. these promoters will be crucial to strategies aimed at using tobacco or *cannabis* trichomes as biofactories for the controlled production of specific biochemical compounds.

Example 3: Identifying "Cannabinoid On" ("CANON") Fragments for Directing Trichome Specific Expression in *Nicotiana Tabacum*

The nucleic acid sequence of the "Cannabinoid On" ("CANON") fragment is set forth in SEQ ID NO: 31. The nucleic acid sequence of the CANON fragment together with the putative TATA Box, 5' UTR, and start codon is set forth in SEQ ID NO: 32. The nucleic acid sequence of the 4×CANON fragment synthetic promoter is set forth in SEQ ID NO: 33. The consensus CANON fragment is derived from the trichome specific promoters from THCA synthases 19603, 1330, 50320, CBCA synthase 3498, and CBDA synthase 20800.

Methods

CANON fragments were identified by searching the purple Kush genome sequence using the BLAT search facility. A BLAT search of the purple Kush genome sequence using a THCA synthase gene yielded the following results:

BLAT Search Results

| ACTIONS | QUERY | SCORE | START | END | QSIZE | IDENTITY | CHRO | STRAND | START | END | SPAN |
|---|---|---|---|---|---|---|---|---|---|---|---|
| browser details | THCA | 979 | 1 | 979 | 979 | 100.0% | scaffold19603 | + | 6901 | 7879 | 979 |
| browser details | THCA | 499 | 257 | 979 | 979 | 89.4% | scaffold50320 | − | 8585 | 9462 | 878 |
| browser details | THCA | 466 | 257 | 979 | 979 | 89.1% | scaffold1330 | − | 2572 | 3369 | 798 |
| browser details | THCA | 332 | 593 | 979 | 979 | 94.2% | scaffold3498 | + | 9881 | 10270 | 390 |
| browser details | THCA | 275 | 590 | 979 | 979 | 85.6% | scaffold6274 | + | 24419 | 24803 | 385 |
| browser details | THCA | 271 | 590 | 979 | 979 | 96.5% | scaffold39155 | − | 4079 | 4464 | 386 |
| browser details | THCA | 251 | 1 | 258 | 979 | 97.7% | scaffold17297 | + | 9858 | 10113 | 256 |
| browser details | THCA | 222 | 590 | 979 | 979 | 96.0% | scaffold46100 | − | 1795 | 2180 | 386 |
| browser details | THCA | 206 | 3 | 271 | 979 | 89.0% | scaffold33063 | − | 10241 | 10479 | 239 |
| browser details | THCA | 196 | 578 | 979 | 979 | 91.2% | scaffold20800 | − | 4646 | 5042 | 397 |
| browser details | THCA | 167 | 69 | 267 | 979 | 94.7% | scaffold12036 | + | 133813 | 134227 | 415 |
| browser details | THCA | 156 | 89 | 258 | 979 | 96.5% | scaffold17775 | − | 18105 | 18274 | 170 |
| browser details | THCA | 142 | 260 | 514 | 979 | 87.5% | scaffold59317 | + | 863 | 1300 | 438 |
| browser details | THCA | 136 | 120 | 268 | 979 | 96.6% | scaffold12751 | − | 46584 | 46732 | 149 |
| browser details | THCA | 128 | 120 | 257 | 979 | 97.1% | scaffold87266 | − | 12096 | 12233 | 138 |
| browser details | THCA | 128 | 120 | 257 | 979 | 97.1% | scaffold23985 | + | 18853 | 18990 | 138 |
| browser details | THCA | 127 | 120 | 258 | 979 | 96.4% | scaffold14882 | + | 59722 | 59860 | 139 |
| browser details | THCA | 123 | 98 | 269 | 979 | 85.9% | scaffold4283 | − | 23256 | 23416 | 161 |

The bolded promoters were selected for further analysis and the sequences of the five promoters were compared. The five promoters showed high sequence similarity from the start of translation to about 160 base pairs upstream of the putative TATA Box, but little sequence similarity upstream of the TATA Box.

A consensus sequence was derived from the five promoters and the sequence was used to test for trichome specific promoter activity in tobacco trichomes using a synthetic promoter termed the "4×CANON fragment synthetic promoter." The 4×CANON fragment synthetic promoter comprises four copies of the consensus CANON fragment, which is not found in nature, in front of one copy of the minimal promoter (TATA Box, start of transcription and first ATG). N. tabacum was transformed with the 4×CANON fragment synthetic promoter placed in front of a GUS-A marker as described in Example 2 and GUS expression analyses were performed.

Results

Figure 4A:
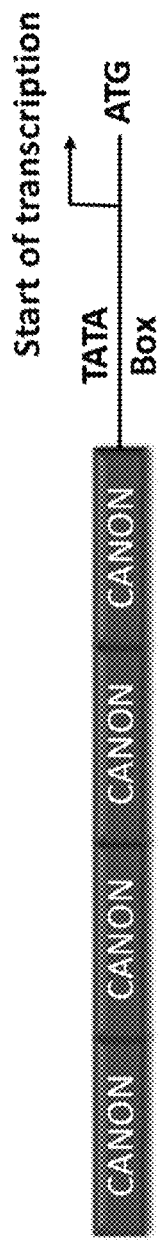
FIG. 4A shows the design of the 4×Cannabinoid On (CANON) fragment synthetic promoter of the present technology.
Figure 4B:
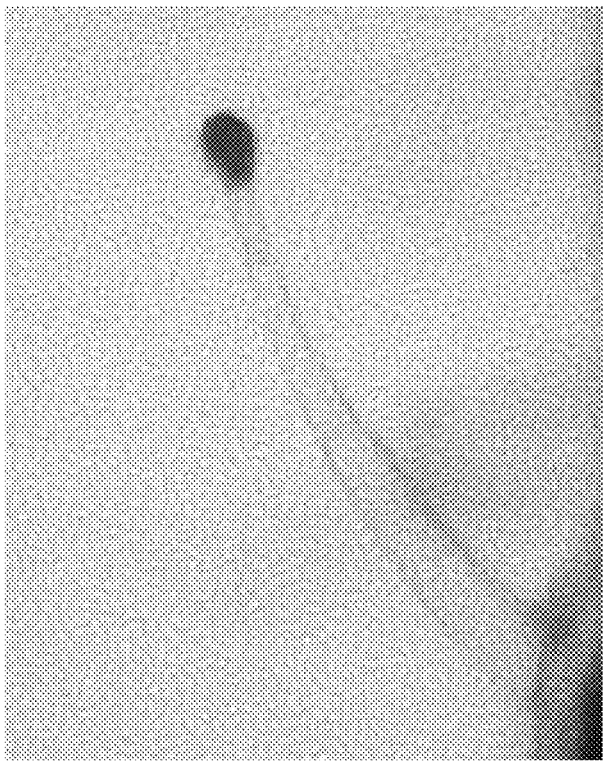
FIG. 4B shows trichome specific expression of the 4×CANON fragment synthetic promoter of the present technology. The activity of the synthetic promoter is indicated by the blue color caused by activity of the GUS reporter gene.

As shown in FIG. 4B, the 4×CANON fragment synthetic promoter directs expression in the trichome. Accordingly, these results demonstrate that the CANON fragment is sufficient to direct trichome specific expression in a gain-of-function promoter and is therefore responsible for the trichome specific expression of a number of cannabinoid biosynthetic enzyme genes including THCA, CBDA, and CBCA synthases.

EQUIVALENTS

The present technology is not to be limited in terms of the particular embodiments described in this application, which are intended as single illustrations of individual aspects of the present technology. Many modifications and variations of this present technology can be made without departing from its spirit and scope, as will be apparent to those skilled in the art. Functionally equivalent methods and apparatuses within the scope of the present technology, in addition to those enumerated herein, will be apparent to those skilled in the art from the foregoing descriptions. Such modifications and variations are intended to fall within the scope of the appended claims. The present technology is to be limited only by the terms of the appended claims, along with the full scope of equivalents to which such claims are entitled. It is to be understood that this present technology is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like, include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

All publicly available documents referenced or cited to herein, such as patents, patent applications, provisional applications, and publications, including GenBank Accession Numbers, are incorporated by reference in their entirety, including all figures and tables, to the extent they are not inconsistent with the explicit teachings of this specification.

Other embodiments are set forth within the following claims.

SEQUENCE LISTING (554 bp)
Tetraketide synthase/olivetol synthase (OLS) promoter

SEQ ID NO: 1

AAAAATAAAATTAATAAATTTTTAATTATTAATATCATTTTATTTTTAA

TAAATAAATATCATTTTTATATTATTATAATATGTATAAAGTTTTAATTG

TATACAAGAAGTCTTATAGTAAGAGTATACACCTTACATCATAATAACTA

CTCGATCTGAAATCAATGGTCAAGAAAAGTTCCCTACCGGTAGGAAACTT

TTGCTAGATCCTACCATAGTCTTCCCTTATATTTATTATGTAGAATCTAT

TATTATATCTAATAATTAACAAATATTAACAAATCATTTTGAAAAATTAT

ATTAAAAAAAAACTTGAAAAGTCAAAGATTAACCATCAATTTGCCAAAT

CAAATTAGTGAGAAAGTAGGTATTATATACCTAACACTCATTTTACATAT

GTCTAGACGTTTATATGTATAGCGTTGTTGTGTAATAAGTTCACTTGT

AGTATCTTGTACATACATAATATATATATATAGGTGTGTTTGTGAACAAT

TATATTATCACACATACACAACTCATTATTATCATAATAATAATAATACC

ATGG (550 bp)
Tetraketide synthase/olivetol synthase 1 (OLS1) promoter

SEQ ID NO: 2

AAAAATAAAATTAATAAATTTTTAATTATTAATATCATTTTATTTTTAA

TAAATAAATATCATTTTTATATTATTATAATATGTATAAAGTTTTAATTG

TATACAAGAAGTCTTATAGTAAGAGTATACACCTTACATCATAATAACTA

CTCGATCTGAAATCAATGGTCAAGAAAAGTTCCCTACCGGTAGGAAACTT

TTGCTAGATCCTACCATAGTCTTCCCTTATATTTATTATGTAGGATCTAT

TATTATATCTAATAATTAACAAATATTAACAAATCATTTTGAAAAATTAT

ATTAAAAAAAAACTTGAAAAGTCAAAGATTAACCATCAATTTGCCAAAT

CAAATTAGTGAGAAAGTAGGTATTATATACCTAACACTCATTTTACATAT

GTCTAGACGTTTATATGTATAGCGTTGTTGTGTAATAAGTTCACTTGT

AGTATCTTGTACATACATAATATATATATATAGGTGTGTTTGTGAACAAT

TATATTATCACACATACACAACTCATTATTATCATAATAATAATAAT (558 bp)
Tetraketide synthase/olivetol synthase 2 (OLS2) promoter

SEQ ID NO: 3

AAAAATAAAATTAATAAATTTTTAATTATTAATATCATTTTATTTTTAA

TAAATAAATATCATTTTTATATTATTATAATATGTATAAAGTTTTAATTG

TATACAAGAAGTCTTATAGTAAGAGTATACACCTTACATCATAATAACTA

CTCGATCTGAAATCAATGGTCAAGAAAAGTTCCCTACCGGTAGGAAACTT

TTGCTAGATCCTACCATAGTCTTCCCTTATATTTATTATGTAGAATCTAT

TATTATATCTAATAATTAACAAATATTAACAAATCATTTTGAAAAATTAT

ATTAAAAAAAAACTTGAAAAGTCAAAGATTAACCATCAATTTGCCAAAT

CAAATTAGTGAGAAAGTAGGTATTATATACCTAACACTCATTTTACATAT

GTCTAGACGTTTATATGTATAGCGTTGTTGTGTAATAAGTTCACTTGT

AGTATCTTGTACATACATAATATATATATATAGGTGTGTTTGTGAACA

ATTATAATATCACACATACACAACTCATTATTATTAGCATAATAATAATA

ATAATAAT (1158 bp)
Olivetol synthase (OLS) ORF

SEQ ID NO: 4

```
   1 atgaatcatc ttcgtgctga gggtccggcc tccgttctcg ccattggcac cgccaatccg
  61 gagaacattt tattacaaga tgagtttcct gactactatt ttcgcgtcac caaaagtgaa
 121 cacatgactc aactcaaaga aaagtttcga aaatatgtg acaaaagtat gataaggaaa
 181 cgtaactgtt tcttaaatga agaacaccta aagcaaaacc caagattggt ggagcacgag
 241 atgcaaactc tggatgcacg tcaagacatg ttggtagttg aggttccaaa acttgggaag
 301 gatgcttgtg caaacmccat caaagaatgg ggtcaaccca agtctaaaat cactcattta
 361 atcttcacta gcgcatcaac cactgacatg cccggtgcag actaccattg cgctaagctt
 421 ctcggactga gtccctcagt gaagcgtgtg atgatgtatc aactaggctg ttatggtggt
 481 ggaaccgttc tacgcattgc caaggacata gcagagaata caaaggcgc acgagttctc
 541 gccgtgtgtt gtgacataat ggcttgcttg tttcgtgggc ttcagagtc tgacctcgaa
 601 ttactagtgg acaagctat ctttggtgat ggggctgctg cggtgattgt tggagctgaa
 661 cccgatgagt cagttgggga aaggccgata tttgagttgg tgtcaactgg gcaaacaatc
 721 ttaccaaact cggaaggaac tattgggga catataaggg aagcaggact gatatttgat
 781 ttacataagg atgtgcctat gttgatctct aataatattg agaaatgttt gattgaggca
 841 tttactccta ttgggattag tgattggaac tccatatttt ggattacaca cccaggtggg
 901 aaagctattt tggacaaagt ggaggagaag ttgcatctaa agagtgataa gttgtggat
 961 tcacgtcatg tgctgagtga gcatgggaat atgtctagct caactgtctt gtttgttatg
1021 gatgagttga ggaagaggtc gttggaggaa gggaagtcta ccactggaga tggatttgag
1081 tggggtgttc ttttgggtt tggaccaggt ttgactgtcg aaagagtggt cgtgcgtagt
1141 gttcccatca aatattaa
```

(996 bp)
Olivetotic acid cyclase (OAC) promoter

SEQ ID NO: 5

AATTTTTGACAATTTTTTTTAATATAACTAACTTGAAGATAATTCCTAAT

ACGAATAAATACAGAAAATATAAACAGTTTTGTTATAACACTTTTAGATC

AGATTATAATTAAATTTTATATTTTTGATAAAAAAATCAATTGAGGGTCC

TATTTGTACCATTTTAGAAAATATAGTGTCCATTTTTATTATTTAGTAAA

ACAGAGAGTCTAATGCGTAACTTTTACAAAAATACATGGTCCAAAATAGT

ATTTACCCTTTAATTTTATTAGCAACTGTCCCAAAAAAAATATGTTTTGA

TGACTGACGTACGGGAATGTAAAGTTTTGTAATAGTGTATTGATTCAAAG

ACAACATAAAGACATCAATCTGAAATCGATTTCAATGTCCCAAAAACACA

TTAATGAGCCTTAATTGCATCCGATAATCATTTTCCATTGGTTTTATTAC

TTCTCATATATATAGACATCACATATATGATAGGATTTCTTGAGAATAAT

GTTAACATTGAGATTTTTATTACAACTGATATATTGATTATGCTTAGATG

GCTTGAATTTGAGCGACATATATAGAAAGAGTATAGAATGATATATATGC

ACATCCAAAATATGTACCAAAATATTAGGTGACAATTTAGATAAATGGAA

```
GAGAAAATTATAGAAAAATGAGGGTTTATATTTTTGTGGTTATTTAATTT
TAGACATAGTGTGATCCAATAATTTTAGGATGTATAATTGTTAGGCACAT
GGATTACTTGTTTTTTTATTAAGTATAACCTTACAAAGTAGATGGTAGTA
ATTAATGTAGAAGGTTCCAATAATGTATTTATATAAATTGTTAGGCATGC
AAAGCCTAATTAATTAATAAATGAGGGTGGCCAATGGCCACTATATATAT
CAAGGCATCGACTGTATGTAGCATAATGTGATTTATATAATTATCAAAAA
AAAAAAATAAAAATAAGAAGAAGAAGAAAGTTGAGAAAGACCATGG
```

(992 bp)
Olivetolic acid cyclase 1 (OAC1) promoter

SEQ ID NO: 6

```
AATTTTTGACAATTTTTTTTAATATAACTAACTTGAAGATAATTCCTAAT
ACGAATAAATACAGAAAATATAAACAGTTTTGTTATAACACTTTTAGATC
AGATTATAATTAAATTTTATATTTTTGATAAAAAAATCAATTGAGGGTCC
TATTTGTACCATTTTAGAAAATATAGTGTCCATTTTTATTATTTAGTAAA
ACAGAGAGTCTAATGCGTAACTTTTACAAAAATACATGGTCCAAAATAGT
ATTTACCCTTTAATTTTATTAGCAACTGTCCCAAAAAAAATATGTTTTGA
TGACTGACGTACGGGAATGTAAAGTTTTGTAATAGTGTATTGATTCAAAG
ACAACATAAAGACATCAATCTGAAATCGATTTCAATGTCCCAAAAACACA
TTAATGAGCCTTAATTGCATCCGATAATCATTTTCCATTGGTTTTATTAC
TTCTCATATATATAGACATCACATATATGATAGGATTTCTTGAGAATAAT
GTTAACATTGAGATTTTTATTACAACTGATATATTGATTATGCTTAGATG
GCTTGAATTTGAGCGACATATATAGAAAGAGTATAGAATGATATATATGC
ACATCCAAAATATGTACCAAAATATTAGGTGACAATTTAGATAAATGGAA
GAGAAAATTATAGAAAAATGAAAATTTATATTTTTGTGGTTATTTAATTT
TAGACATAGTGTGATCCAATAATTTTAGGATGTATAATTGTTAGGCACAT
GGATTACTTGTTTTTTTATTAAGTATAACCTTACAAAGTAGATGGTAGTA
ATTAATGTAGAAGGTTCCAATAATGTATTTATATAAATTGTTAGGCATGC
AAAGCCTAATTAATTAATAAATGAGGGTGGCCAATGGCCACTATATATAT
CAAGGCATCGACTGTATGTAGCATAATGTGATTTATATAATTATCAAAAA
AAAAAAATAAAAATAAGAAGAAGAAGAAAGTTGAGAAAGAGA
```

(485 bp)
OlivetoLic acid cyclase (OAC) ORF

SEQ ID NO: 7

```
  1 aaaaaagaag aagaagaaga aagttgagaa agagaatggc agtgaagcat ttgattgtat
 61 tgaagttcaa agatgaaatc acagaagccc aaaaggaaga attttttcaag acgtatgtga
121 atcttgtgaa tatcatccca gccatgaaag atgtatactg ggtaaagat gtgactcaaa
181 agaataagga agaagggtac actcacatag ttgaggtaac atttgagagt gtggagacta
241 ttcaggacta cattattcat cctgcccatg ttggatttgg agatgtctat cgttctttct
301 gggaaaaact tctcattttt gactacacac cacgaaagta gactatatat agtagccgac
361 caagctgcct tcatcttcat cttctcaaat aatatatcta atatctaatt atataataat
421 aactacttaa taaaagactg tgtttataac attaaataat aataataata aagtcttttg
481 tagct
```

SEQUENCE LISTING (1361 bp)
Aromatic prenyltransferase (PT) promoter

SEQ ID NO: 8

TCAAACCAGATTTTTTATAATAATTT

ACACACCAATTAACTAAGAAATTCTAACTAGAGTTAGTGTTGAATTAGAA

GGAGTATCAAGGTAACCTATCTCCTTTGTCTCTTTAAATTTTTAAAAGAA

AAGCTaTTGTTGTAATTAGTTTGGATTTTATGGGTTAGGTTTTGTAGAGT

TTGTTTGAGCTTAAAATTGTTGTTGGTTTGATTTAAGGTTGAATTCTGTG

TTGGTTTGTAAGATTTTAGCTGATGTAGTTCGTGTTGGAGGAGTTCGAGT

TTTTGAACTCAAAGTCCACTCAACAATATGGTGAAATTAGTTTTAGGTGG

TTTTAGATGCTTTTGAAGTGTATGTTTTGTTTAGATTACCCTCTTTTTGG

TAAGTTTGATAGCCTTTGGTCAAGGAATGACTTAATTTTGAAGGTCTGAA

AGTTGAGTAGTTTTGAACTCTTTTCTGCCCAAAATGGTTTCGAATGAGTT

GTACTTGTCATATGTGATTTGAGTGGTAAGGTTXGGAAGGGTAGTCCTAG

ACAGTGTTTTCAATGATTAGGTTTGGGGTTGGTGAATCTAGAGTTAAGAG

CCTAGAGTTTTGGTTGCTTGGATTGGTGTGACCTGGTTGTTAGTATCCTT

ATCAAGGGATCCCGAATAGGTGATGAGTGAGGTTTGGATGGTATATTCTG

GATCAAAATTTTTAGATGGGGTXXAAACTGATAGTTTCAAAAATGTGTGT

GTGTGTCTGGTTAAGGATTTATTTTGGGAAGGCTCTAGTTGGGAGGTCCT

GGATTGGAAGTTCTAGATGTGAGGCTCCGGGTAGGAGGGTCCTGTAGGAA

GATTCTAGATGGTATTTGGTGGTCGAGATGAGGGATTTCCGAACATGTTT

TAATAGTTACAATAATTCATAAATTTTCAACACTAAATCAAAATATTAAT

TTTGATATGATTGTATAAATTTAATCTCATCGTAGTGTAGAGCTCTACAT

GCATGCATGGTTTGTATAGCCATAATTAATTAATTAGGCAAGAAAGATAG

ATGTGCCTACCATGCATGACTTCTAAAACATGGATGACTTTAAATTTTGA

AACCAAGCAAAAATTGTTTTACTATAAATCTTGTTAATTTTTCATTATTG

ATATCACTATGTTATTCTAACCCTTTCGTAGCCATAATTAGTTAATTAGG

CAAGAAAGATAGATGTGCCTACCATGCATGACTTCTAAAACATGGATGAC

TTTAAATTTTGAAACCAAGCAAAAATTATTTTACTATAAATCTTGTTATT

TTTTCATTATTGATATCACTATGTTATTCTAACCCTTTCTTTCCCTCATT

TTTTCTTAATATTCAATCAATAATAATCTCCATGG (1357 bp)
Aromatic prenyltransferase 1 (PT) promoter

SEQ ID NO: 9

TCAAACCAGATTTTTTATAATAATTT

ACACACCAATTAACTAAGAAATTCTAACTAGAGTTAGTGTTGAATTAGAA

GGAGTATCAAGGTAACCTATCTCCTTTGTCTCTTTAAATTTTTAAAAGAA

AAGCTaTTGTTGTAATTAGTTTGGATTTTATGGGTTAGGTTTTGTAGAGT

TTGTTTGAGCTTAAAATTGTTGTTGGTTTGATTTAAGGTTGAATTCTGTG

TTGGTTTGTAAGATTTTAGCTGATGTAGTTCGTGTTGGAGGAGTTCGAGT

TTTTGAACTCAAAGTCCACTCAACAATATGGTGAAATTAGTTTTAGGTGG

```
TTTTAGATGCTTTTGAAGTGTATGTTTTGTTTAGATTACCCTCTTTTTGG

TAAGTTTGATAGCCTTTGGTCAAGGAATGACTTAATTTTGAAGGTCTGAA

AGTTGAGTAGTTTTGAACTCTTTTCTGCCCAAAATGGTTTCGAATGAGTT

GTACTTGTCATATGTGATTTGAGTGGTAAGGTTCGGAAGGGTAGTCCTAG

ACAGTGTTTTCAATGATTAGGTTTGGGGTTGGTGAATCTAGAGTTAAGAG

CCTAGAGTTTTGGTTGCTTGGATTGGTGTGACCTGGTTGTTAGTATCCTT

ATCAAGGGATCCCGAATAGGTGATGAGTGAGGTTTGGATGGTATATTCTG

GATCAAAATTTTTAGATGGGGTCCAAACTGATAGTTTCAAAAATGTGTGT

GTGTGTCTGGTTAAGGATTTATTTTGGGAAGGCTCTAGTTGGGAGGTCCT

GGATTGGAAGTTCTAGATGTGAGGCTCCGGGTAGGAGGGTCCTGTAGGAA

GATTCTAGATGGTATTTGGTGGTCGAGATGAGGGATTTCCGAACATGTTT

TAATAGTTACAATAATTCATAAATTTTCAACACTAAATCAAAATATTAAT

TTTGATATGATTGTATAAATTTAATCTCATCGTAGTGTAGAGCTCTACAT

GCATGCATGGTTTGTATAGCCATAATTAATTAATTAGGCAAGAAAGATAG

ATGTGCCTACCATGCATGACTTCTAAAACATGGATGACTTTAAATTTTGA

AACCAAGCAAAAATTGTTTTACTATAAATCTTGTTAATTTTTCATTATTG

ATATCACTATGTTATTCTAACCCTTTCGTAGCCATAATTAGTTAATTAGG

CAAGAAAGATAGATGTGCCTACCATGCATGACTTCTAAAACATGGATGAC

TTTAAATTTTGAACCAAGCAAAAATTATTTTACTATAAATCTTGTTATT

TTTTCATTATTGATATCACTATGTTATTCTAACCCTTTCTTTCCCTCATT

TTTTCTTAATATTCAATCAATAATAATCTCC
```

(1188 bp)
Aromatic prenyltransferase (PT) ORF

SEQ ID NO: 10

```
  1 atgggactct catcagtttg taccttttca tttcaaacta attaccatac tttattaaat
 61 cctcacaata ataatcccaa aacctcatta ttatgttatc gacacccaa aacaccaatt
121 aaatactctt acaataattt tccctctaaa cattgctcca ccaagagttt tcatctacaa
181 aacaaatgct cagaatcatt atcaatcgca aaaaattcca ttagggcagc tactacaaat
241 caaactgagc ctccagaatc tgataatcat tcagtagcaa ctaaaatttt aaactttggg
301 aaggcatgtt ggaaacttca agaccatat acaatcatag catttacttc atgcgcttgt
361 ggattgtttg ggaaagagtt gttgcataac acaaatttaa taagttggtc tctgatgttc
421 aaggcattct ttttttggt ggctatatta tgcattgctt cttttacaac taccatcaat
481 cagatttacg atcttcacat tgacagaata aacaagcctg atctaccact agcttcaggg
541 gaaatatcag taaacacagc ttggattatg agcataattg tggcactgtt tggattgata
601 ataactataa aaatgaaggg tggaccactc tatatatttg gctactgttt tggtattttt
661 ggtgggattg tctattctgt tccaccattt agatggaagc aaaatccttc cactgcattt
721 cttctcaatt tcctggccca tattattaca aatttcacat tttattatgc cagcagagca
781 gctcttggcc taccatttga gttgaggcct tcttttactt tcctgctagc atttatgaaa
841 tcaatgggtt cagctttggc tttaatcaaa gatgcttcag acgttgaagg cgacactaaa
901 tttggcatat caaccttggc aagtaaaatat ggttccagaa acttgacatt attttgttct
```

SEQUENCE LISTING

```
  961 ggaattgttc tcctatecta tgtggctgct atacttgctg ggattatctg gccccaggct 1021 ttcaacagta acgtaatgtt actttctcat gcaatcttag cattttggtt aatcctccag 1081 actcgagatt ttgcgttaac aaattacgac ccggaagcag gcagaagatt ttacgagttc 1141 atgtggaagc tttattatgc tgaatattta gtatatgttt tcatataa
```

(805 bp)
Hexanoyl-CoA synthetase (AAE1-1) promoter

SEQ ID NO: 11

ATAATGTTATTTATTATTTAATACAATATGACATTTATACAGCGTACCAA

ACGAGCCCATAATGTATTGCAATTGTATTGTTGTACGAATTAAAATAATA

AAATACTAATTAAGTTAATATTGTAAGATAGATAATATGGCAAACAAATA

AATAATTTTCAGTTGAGAATATGTACAAAATTAAAGTTGATTTTACAAGA

AACAAGTAGTACTAATTAAAATGGTAGATTTACATATAGTGTTCGTTAAA

TTTGAAAAAGAAAACGACTAATTCATTGGAAAATTGATTGTGGAAGAAA

TCAAAATTTGGTGGCTGAACCGCCCTAGTTACTTAACACAATTCATAAAA

CAACCCTACACTACTTACCCTACACTATATACGTATATTTTTTTTTATA

TTCCATTTGTTAATAAAATAAATATGCATTGTTATTATGTGTACCAAGAT

GCTAATACGGTGACGTTTTATATAAGTTTATAATTTTTTATTAAAGTAAA

ACAATTGTCCCTCAATATTAAATTAAAGAAAATAAGTAGGTTTTAGCATT

TCTCATGATAAATAAGTAGGAGTAGTAAGTATATTAATTTATATGCATAT

GTTAAAAGGCAACACAGTGATAGGTTGTGTAGTACGTACCCAAACCAAAT

TCCAGCCTAATCCATTATTAATGAGCAAGTCCTTGATAAAATAAGGTGCA

TGTTGTTAGATCAAATAACCCGTCCCGAAATCCAATATATATATATATAT

AATATTCAAACTCTCTCTTTCTATCTTCGTACAATTTAATAGAAGTAACC

ATGGG (800 bp)
Hexanoyl-CoA synthetase (AAE1-1') promoter

SEQ ID NO: 12

ATAATGTTATTTATTATTTAATACAATATGACATTTATACAGCGTACCAA

ACGAGCCCATAATGTATTGCAATTGTATTGTTGTACGAATTAAAATAATA

AAATACTAATTAAGTTAATATTGTAAGATAGATAATATGGCAAACAAATA

AATAATTTTCAGTTGAGAATATGTACAAAATTAAAGTTGATTTTACAAGA

AACAAGTAGTACTAATTAAAATGGTAGATTTACATATAGTGTTCGTTAAA

TTTGAAAAAGAAAACGACTAATTCATTGGAAAATTGATTGTGGAAGAAA

TCAAAATTTGGTGGCTGAACCGCCCTAGTTACTTAACACAATTCATAAAA

CAACCCTACACTACTTACCCTACACTATATACGTATATTTTTTTTTATA

TTCCATTTGTTAATAAAATAAATATGCATTGTTATTATGTGTACCAAGAT

GCTAATACGGTGACGTTTTATATAAGTTTATAATTTTTTATTAAAGTAAA

ACAATTGTCCCTCAATATTAAATTAAAGAAAATAAGTAGGTTTTAGCATT

TCTCATGATAAATAAGTAGGAGTAGTAAGTATATTAATTTATATGCATAT

GTTAAAAGGCAACACAGTGATAGGTTGTGTAGTACGTACCCAAACCAAAT

TCCAGCCTAATCCATTATTAATGAGCAAGTCCTTGATAAAATAAGGTGCA

```
TGTTGTTAGATCAAATAACCCGTCCCGAAATCCAATATATATATATAT

AATATTCAAACTCTCTCTTTCTATCTTCGTACAATTTAATAGAAGTAATA
```

(1000 bp)
Hexanoyl-CoA synthetase (AAE3) promoter                              SEQ ID NO: 13

```
TAAAAATTAGATTATATTTTTATCAGAATTTTTTATTTATATTTTTCATC

GAGTTACGTTGATTTAACGTATGTTGACGGTGCTTATAATTGTCTATTAT

TTTTAAGTTATATACACGCACTACTTACGTAAATTTAGTTGGCAGATTTT

CTGTCTCTATGGGCTATATTGTTGGACATCAGCTATCTCATTAATTAATA

ATACCATACTTTTTCTTAAAAGTTAAATAAAACAAAATTATACACGCACT

GATTCGAATGGTGTAGCCCACGCACTTGCTAAGTCTGTTACTAGTTCTGT

AGGAGTTAATGTGTGGACTGATGCTTGTCCTAGATTTTATCAGCTATCTC

ATTAATTAATAATACCATACTTTTTCTTAAAAGTTAAATAAAACAAAATT

ATACACGCACTACGATAAGGATTATATAAATGATTAACTAAAAAATATCT

ATTTAACATGCCATACCGCGAAAGGTTTTGCGCCATTCGATGGTGTCCGG

GATCTCGACGCTCTCCCTTATGCGACTCCTGCATTAGGAAGCAGCCCAGT

AGTAGGTTGAGGCCGTTGAGCACCGCCGCCGCAAGGAATGGTGCATGCAA

GGAGATGGCGCCCAACAGTCCCCCGGCCACGGGGCCTGCCACCATACCCA

CGCCGAAACAAGCGCTCATGAGCCCGAAGTGGCGAGCCCGATCTTCCCCA

TCGGTGATGTCGGCGATATAGGCGCCAGCAACCGCACCTGTGGCGCCGGT

GATGCCGGCCACGATGCGTCCGGCGTAGAGGATCGAGATCTCGATCCCGC

GAAATTAATACGACTCACTATAGGGGAATTGTGAGCGGATAACAATTCCC

CTCTAGAAATAATTTTGTTTAACTTTAAGAAGGAGATATACCATGAAACA

CCACCACCACCACCACCACGGTGGTCTGGTTCCGCGTGGTTCCCATG

ATCAAACAAGTTTGTACAAAAAAGCAGGCTCCGAATTCGCCCTTATGGAG
```

(869 bp)
Hexanoyl-CoA synthetase (AAE12) promoter                             SEQ ID NO: 14

```
GTGACAAACTGAAGAATTCTGTTTATTTTATTTTATACATT

AGTGATGTTTTTTACTTTTTTAGAGTTATTTTTATGCCTATGTAATTTGC

ATATTGTAGTGGAGTTTATGCAGTTATTTTTTTGTTGTTATTTAGTTGTT

TAACTAAGAGAAATAAATATATATATTTTTTATTTGTGCGTTGTTTTTAT

TTTATTTTTTAAGTTGACGTAAGTGTTGATGCTCAATTAATTTTTATATT

AACATAAAATTGTTATTGTGTTGCTTATTCGTTGCTATTGAGTTATTTCA

ATATTGTACTTTTTGAAGTTTTTGTCTTATAAATTTATTTTTATTTGCAT

AACATATGATAAACTTTAATGGATTTATATGTTACGGTTAAGTTGTTTTC

TAGTTGCTTTTGTGTTGTTGTTTAGTTGTTTTGCGCTGAGAAAAGAAGCC

CTATACGTTAAAATTCACTTTGTCCGAATTCGCCACGTGGCAACTACTGC

TACGTTCTGACGCTACAGATTGTGAGCGTCAGGCAAGTCTGAATGCTTTG

TCCCGCACTCACGTGTGAGTCTCACTCGCCCACATAGCCATATGTGTGCC

ACACATCTCCTTGCGCATCTAGGGGAGTTTTTCTACTGTATTTTTGTAAA
```

TAAGAAACTTTGAAAATAGTATATTTGAAATTAATAAATAATATAAATGT

TTATTTTTACTTATAGTAGTATAAATATTTATTTAAGATAATTTTAACTT

AAAATAGAAAAAATCTCAAAAAAAAATAAAATAAAATAAACTATACCTTT

AATTTTTATATTTATGAAAATTTCCCGTATAAAAGGGAAGATTTTTTTTT

TTAAAATTAGTAGGTAAGTAATAGGATG (2351 bp)
Hexanoyl-CoA synthetase (AAE1-1) ORF

SEQ ID NO: 15

```
   1 tcttggagtg tatatataga tatatatata catttctcca tttttggcca cccaaattac
  61 ctaaattgaa ttcgtcgtgt tcgtctttct ccgccataaa taacaattga tttccttcgt
 121 tctttcaagt ttbbgtcaac tgagtactga gatccagtct gagtcgacac ttgtagaggt
 181 tcgaaaatgg cgcagaagaa gtttattttt gaggttgaaa aggctaagga agctaaggat
 241 ggaaggcctt ccatgggacc tgtttatcga agtatgtacg ccaaggatgg cttccctcct
 301 ccgattgatg gattggattg ttgttgggat gtgtttaggc tttctgtgga gagaaatcct
 361 ggaaacaaaa tgctcggtcg ccgggaggtt gtggatggga aggctggaaa gtatgtttgg
 421 caaacttata aggaggttta tgattgtgtg ataaaacttg gaaatgccat gcgcagttgt
 481 ggtttcggag aaggagacaa atgtggtatc tatggtgcca attgctctga atggattatg
 541 agcatgcagg cttgcaatgc tcatggactc tattgtgttc cgttgtatga caccttaggt
 601 gctaatgcaa ttgagtttgt cataaaacat gccgaggtta caattgcttt tgcagaagag
 661 aaaaagcttc ctgagctgtt gaaaacactt cctaacacca cagactattt aaaaacactt
 721 gtgagctttg gaaggtcac accggaacaa agggaatctg ttgaaaagtt tggattgaag
 781 atctattcct gggaagagtt cttgcaattg ggtgattgta agatttcga tcttccagtg
 841 aaaaagaaaa ctgatatatg cactataatg tatactagtg gaactactgg tgacccaaag
 901 ggagtactga tatccaatga gagcatcatt tctcttttgg ctggggtgag gcgattgctt
 961 gagagtgtaa atgaaaagtt gaccgagaaa gatgtatttc tttcatatct tccccttgca
1021 catatcttcg atcgggtgat tgaggagtta tttattttgc atggtgcctc aatcgggttc
1081 tggcgtggcg atgtcaaatt attacttgaa gacattgggg agctaaaacc aactattttc
1141 tgtgccgttc cccgtgtgct ggatagagtc tatgctggtt tgacgcagaa gatttctgct
1201 gggggattct aaagaagac tctcttcaat ttcgcatact cacgcaagta taataacatg
1261 cgaaaggggc ttaaacacgg ggacgcagct ccattatgtg acaaaattgt atttagtaag
1321 gtgaagcaag gtttgggagg taatgtgcgg cttattctgt ctggagctgc gcctctagct
1381 cctcatgttg aagcttactt acgagttgtg acatgtgctc atgtttgcca aggatatggg
1441 ctaactgaaa cttgtgcggg gacatttgtc tcgataccaa atgaactacc aatgctcggt
1501 acagttggtc ctccagtacc caatgttgat gtatgtctgg aatcagttcc ggaaatggga
1561 tatgatgccc ttgcagaagt accgcgtgga gaagtatgtg tgaagggaag caccttattc
1621 tctgggtact acaaacgtga agacttaacc aaggaggtca tgattgatgg gtggttccat
1681 acaggtgatg ttggtgagtg gcaagcagat ggaagcttga aaatcattga ccgtaagaaa
1741 aatatttca acttctca aggagaatat gtggcagttg agaacttaga gaacatttat
1801 ggtctgtttt ctgacattga ctcaatatgg gttacggga acagcttga gtccttcctc
1861 gttgctgtga ttaacccgaa ccagcaagca cttgaacgtt gggccggaga gaataatata
```

SEQUENCE LISTING

```
1921 tctggtgact tcaagtccat ttgtgaaaat ccaagagcaa aggaatacat tttgggagag 1981 ctcaataaga ttggcaaaga gaaaaagttg aaaggttttg agttcataag agctgttcac 2041 cttgacccag aggcatttga catagaacgt gaccttatta ctccaacata taagaaaaag 2101 agaccccagt tgctcaaata ctaccagagt gttattgata acatgtacaa ggaaggaaac 2161 aagcccagga cctgaaagat ataatagaca tttagagctt cactttctaa tatttcttca 2221 cacacttccc attttcatct ctctcttact tattacacta taaataatta acaaggttta 2281 ctgtgttgta aatgacattt taatattttc atagtctcaa tgtttcaatt cttagaggac 2341 gttttgattg g
```

(420 bp)
CBDA Synthase (CBDAS) promoter

SEQ ID NO: 16

GTTAATAAACATACTTGTGAGTAGATCTAAGATCCTGGTAAAATAATTCCCAACATATT

TCAATCGTAAATTCATGAGTGATTCTTATCACTTCTTAAAAAAAGATAT

AAAGATCCATAGATAAATAT TTGCTAGTCC TTTCTTTCCA TAGTCAACTT

CAATATGGCA TCTTAACTTC TTTCCATCAA CAAATGATGC TCAACTACTT

AATGTACAAT TTATATTTAT TTTTAGTAAG GGATACACCT AACAATGATG

CCTAATTTTG GTGAATTTTT TTTTACCACA TGTGACTTAA TGATATCAAA

TTTGGAAATA TTTAGTTAAT TTATTTGCCC CTGCTCCATT ATATAAAGCT

ATAAATAGGA TAGTTCTTAA TTCATAGTAA TTCAAAAATT ATTAGAACTA

AAGAACCATG G (416 bp)
CBDA Synthase 1 (CBDAS1) promoter

SEQ ID NO: 17

GTTAATAAACATACTTGTGAGTAGATCTAAGATCCTGGTAAAATAATTCCCAACATATT

TCAATCGTAAATTCATGAGTGATTCTTATCACTTCTTAAAAAAAGATAT

AAAGATCCATAGATAAATAT TTGCTAGTCC TTTCTTTCCA TAGTCAACTT

CAATATGGCA TCTTAACTTC TTTCCATCAA CAAATGATGC TCAACTACTT

AATGTACAAT TTATATTTAT TTTTAGTAAG GGATACACCT AACAATGATG

CCTAATTTTG GTGAATTTTT TTTTACCACA TGTGACTTAA TGATATCAAA

TTTGGAAATA TTTAGTTAAT TTATTTGCCC CTGCTCCATT ATATAAAGCT

ATAAATAGGA TAGTTCTTAA TTCATAGTAA TTCAAAAATT ATTAGAACTA

AAGAAAA (535 bp)
CBDA Synthase (CBDAS) 20800 promoter

SEQ ID NO: 18

AGACGTT ATAGCTTTATTGTCTAAATT TCTTGGGGTA GTTTTGTCCC ATGTTGCTCG

CTTACTTTAGAAGTTCAAAG TTTGACAAAA CATGCTATTC GGTTATACAA

TGAGCTATCC

TAGTTCAAGG AGATTCCTGT GCTATTTGTG GATGTCTACA TTGTAAATTC

ATGAGTGATT CTTATAACTT TATTAAAAAA AAGACAAATA GATCCATAGA

TAAATATTTG CAAGTGCTTT CTTGTCATAG CAATTTTTTT TTACATAGGT

AATTTAAAAA ATTCATCTTA ACTTTTTTTC ATCAATAAAT GATGCTCAAT

TATTCAATGC ACCATGTACA TTTATTTTTA ATAAGGGCTG CACCTAACAA

| SEQUENCE LISTING |
|---|
| AGGTGCCTAA TTTTGGTAAA AAAGAAATTA CGGCATGTGA ATATTTAATG |
| AGCATCAAAT TACAAAATAT TTAGCTAATT TCTTTACCCC CACTCCAATC |
| TATAAAGCTA TAAATAGGAT AATTTTCCAT TCATAGTAAT TTCCAACATT |
| ACGACTAAAG AACCATGG |

(531 bp)
CBDA Synthase (CBDAS) 20800' promoter

SEQ ID NO: 19

| AGACGTT ATAGCTTTATTGTCTAAATT TCTTGGGGTA GTTTTGTCCC ATGTTGCTCG |
|---|
| CTTACTTTAGAAGTTCAAAG TTTGACAAAA CATGCTATTC GGTTATACAA |
| TGAGCTATCC |
| TAGTTCAAGG AGATTCCTGT GCTATTTGTG GATGTCTACA TTGTAAATTC |
| ATGAGTGATT CTTATAACTT TATTAAAAAA AAGACAAATA GATCCATAGA |
| TAAATATTTG CAAGTGCTTT CTTGTCATAG CAATTTTTTT TTACATAGGT |
| AATTTAAAAA ATTCATCTTA ACTTTTTTTC ATCAATAAAT GATGCTCAAT |
| TATTCAATGC ACCATGTACA TTTATTTTTA ATAAGGGCTG CACCTAACAA |
| AGGTGCCTAA TTTTGGTAAA AAAGAAATTA CGGCATGTGA ATATTTAATG |
| AGCATCAAAT TACAAAATAT TTAGCTAATT TCTTTACCCC CACTCCAATC |
| TATAAAGCTA TAAATAGGAT AATTTTCCAT TCATAGTAAT TTCCAACATT |
| ACGACTAAAG AAAA |

(1635 bp)
CBDA Synthase (CBDAS) ORF

SEQ ID NO: 20

```
   1 atgaagtgct caacattctc cttttggttt gtttgcaaga taatattttt cttttctca
  61 ttcaatatcc aaacttccat tgctaatcct cgagaaaact tccttaaatg cttctcgcaa
 121 tatattccca ataatgcaac aaatctaaaa ctcgtataca ctcaaaacaa cccattgtat
 181 atgtctgtcc taaattcgac aatacacaat cttagattca cctctgacac aaccccaaaa
 241 ccacttgtta tcgtcactcc ttcacatgtc tctcatatcc aaggcactat tctatgctcc
 301 aagaaagttg gcttgcagat tcgaactcga agtggtggtc atgattctga gggcatgtcc
 361 tacatatctc aagtcccatt tgttatagta gacttgagaa acatgcgttc aatcaaaata
 421 gatgttcata gccaaactgc atgggttgaa gccggagcta cccttggaga gtttattat
 481 tgggttaatg agaaaaatga gaatcttagt ttggcggctg ggtattgccc tactgtttgc
 541 gcaggtggac actttggtgg aggaggctat ggaccattga tgagaaacta tggcctcgcg
 601 gctgataata tcattgatgc acacttagtc aacgttcatg aaaagtgct agatcgaaaa
 661 tctatggggg aagatctctt ttgggcttta cgtggtggtg agcagaaag cttcggaatc
 721 attgtagcat ggaaaattag actggttgct gtoccaaagt ctactatgtt tagtgttaaa
 781 aagatcatgg agatacatga gcttgtcaag ttagttaaca atggcaaaa tattgcttac
 841 aagtatgaca agatttatt actcatgact cacttcataa ctaggaacat tacagataat
 901 caagggaaga ataagacagc aatacacact tacttctctt cagtttttcct tggtggagtg
 961 gatagtctag tcgacttgat gaacaagagt tttcctgagt tgggtattaa aaaaacggat
1021 tgcagacaat tgagctggat tgatactatc atcttctata gtggtgttgt aaattacgac
1081 actgataatt ttaacaagga aattttgctt gatagatccg ctgggcagaa cggtgctttc
1141 aagattaagt tagactacgt taagaaacca attccagaat ctgtatttgt ccaaatttg
```

```
   1201 gaaaaattat atgaagaaga tataggagct gggatgtatg cgttgtaccc ttacggtggt 1261 ataatggatg agatttcaga atcagcaatt ccattccctc atcgagctgg aatcttgtat 1321 gagttatggt acatatgtag ttgggagaag caagaagata acgaaaagca tctaaactgg 1381 attagaaata tttataactt catgactect tatgtgtcca aaaatccaag attggcatat 1441 ctcaattata gagaccttga tataggaata aatgatccca agaatccaaa taattacaca 1501 caagcacgta tttggggtga aagtatttt ggtaaaaatt ttgacaggct agtaaaagtg 1561 aaaaccctgg ttgatcccaa taacttttt agaaacgaac aaagcatccc acctcttcca 1621 cggcatcgtc attaa
```

(800 bp)
THCA Synthase (THCAS) 19603 promoter

SEQ ID NO: 21

```
CTTATCACTC ATTCGGGAGC AACTTAAAAA AATTACAATT ATTATGAAAG

ACGGCACAAA AAGCGAATTA ATTACCTAAT CGTAAATAAA AGAAATTTTA

CATAAATATA TTATATAATT TTATATTATT CATAAAAAAT ATAAAATAGT

ATTAGACTGA ATTGAGATTT GATTCGTAAC TAAAAATTAA TTTCTTTAAT

GTAAAATTTT AAAACAAAT TATTAAAACC GCGTGAAGCG CGGATCTATT

CCCTAGTTCA ATAATAAAGT ACATACTAGA GGAGGTTAGA ATTTATAATT

TTTCATTTAA ATATTTGAAT TTACTTTACT GTTCTTTGTT ATTCTTCATT

TAATTTTGCT ATTTGTTATT TTACTTTTCA AAAATTATAA TTTTAATTAC

CAAATAAAAA GTAAAATAGA TATTGCTACT TGATATTCAC TCTTTATGGG

AACCATAATA AACTATAAAA GTCATTATGT GTACTTGCTA CCATAGGCAC

CTATATCCCA CAAACTAGCT ACCATAGCCA ATTTCTTGTT TTTTGTTTCC

AATATCCAAT TTTTATTGAT GCCAAACTAT TCAATGTACA ATCTACATTT

ATTTTCAATA AGGGCTTCAC CTAACAAAGG TGCCTAATTT TAGTTGATTT

ATTTTTTATC ACATGTGACT ATTTAATGAC TATCAAATTA TAAAATATTT

AAGTCAATTT ATTTGCCCCA ACTCCAATAT ATAATATTAT AAATAGGATA

GTTCTCAATT CCTAATAATT CAAAAAATCA TTAGGACTGA AGAACCATGG
```

(796 bp)
THCA Synthase (THCAS) 19603' promoter

SEQ ID NO: 22

```
CTTATCACTC ATTCGGGAGC AACTTAAAAA AATTACAATT ATTATGAAAG

ACGGCACAAA AAGCGAATTA ATTACCTAAT CGTAAATAAA AGAAATTTTA

CATAAATATA TTATATAATT TTATATTATT CATAAAAAAT ATAAAATAGT

ATTAGACTGA ATTGAGATTT GATTCGTAAC TAAAAATTAA TTTCTTTAAT

GTAAAATTTT AAAACAAAT TATTAAAACC GCGTGAAGCG CGGATCTATT

CCCTAGTTGA ATAATAAAGT AGATAGTAGA GGAGGTTAGA ATTTATAATT

TTTCATTTAA ATATTTGAAT TTACTTTACT GTTCTTTGTT ATTCTTCATT

TAATTTTGCT ATTTGTTATT TTACTTTTCA AAAATTATAA TTTTAATTAC

CAAATAAAAA GTAAAATAGA TATTGGTACT TGATATTCAC TCTTTATGGG

AACCATAATA AACTATAAAA GTCATTATGT GTACTTGCTA CCATAGGCAC

CTATATCCCA CAAACTAGCT ACCATAGCCA ATTTCTTGTT TTTTGTTTCC
```

| SEQUENCE LISTING |
|---|

AATATCCAAT TTTTATTGAT GCCAAACTAT TCAATGTACA ATGTACATTT

ATTTTCAATA AGGGCTTCAC CTAACAAAGG TGCCTAATTT TAGTTGATTT

ATTTTTTATC ACATGTGACT ATTTAATGAC TATCAAATTA TAAAATATTT

AAGTCAATTT ATTTGCCCCA ACTCCAATAT ATAATATTAT AAATAGGATA

GTTCTCAATT CCTAATAATT CAAAAAATCA TTAGGACTGA AGAAAA (796 bp)
THCA Synthase (THCAS) 50320 promoter    SEQ ID NO: 23

TTATTTAAAT TTCTCAGAGA GATATAGAGA ATTTACAATA GGTCAAGTTG

TATATTTTTT AATCCGAATA ATTAATGCTT TTGAATATCC ATCATCAATA

TTGAATAATA AAGTAGATAG CAGAGGAGAT TAGAACTCAT AATTTTTCAT

TTATATTTTT GAATTTAGTT TACTGTTCTT TATTATTCTT CATTTAATTT

TGCTATATGT TATTTTACTT TTCAAAAATT CTAATTTTGA TTACCAAATA

AAAAATAAAA TATATATTGG TACTTCATAT TTAGTTTTTA TGGGAATGAT

AATGAATGAT ATTGTAATAA ACTATAAAAG TAATTTTGTA TACTTGCATA

GTTCTTAATT TTTACCCAAA AAAATATATA TTAATGAAAA AAAAAGGTGG

AAAGTGCCAT AGGCACCTAT ATCCCACAAA CTAGCTATAA GATATTGAAA

GACAAATAGA TCCATAGATA AATATTTGCG TGTCCTTTCT TTTCATATCT

AATTTTTTGT TTTTTTATTT TTTTCCAATA GTCAATTTTG GCAGCTTAAC

TTCTTTCCAT AAATAATGAT GCCAAACTAT TCAATGTAAA ATTTAGATTT

ATTTTCATTA AGGGCTTCAC CTAACAAATG TGCCTAATTT TTGTGGATTT

TTTTACCATA TGTCGCTATT TAATGACTAC CAAATTATAG AATTATTTAA

GTCAATTTCT CAGTCCCCGC TCCAATATAT AAAGTTATAG AAAGGACAAT

TCTTAATTCA TAGTAATTCA AAAATCATTA AGACTAAAAA CCATGG (792 bp)
THCA Synthase (THCAS) 50320' promoter    SEQ ID NO: 24

TTATTTAAAT TTCTCAGAGA GATATAGAGA ATTTACAATA GGTCAAGTTG

TATATTTTTT AATCCGAATA ATTAATGCTT TTGAATATCC ATCATCAATA

TTGAATAATA AAGTAGATAG CAGAGGAGAT TAGAACTCAT AATTTTTCAT

TTATATTTTT GAATTTAGTT TACTGTTCTT TATTATTCTT CATTTAATTT

TGCTATATGT TATTTTACTT TTCAAAAATT CTAATTTTGA TTACCAAATA

AAAAATAAAA TATATATTGG TACTTCATAT TTAGTTTTTA TGGGAATGAT

AATGAATGAT ATTGTAATAA ACTATAAAAG TAATTTTGTA TACTTGCATA

GTTCTTAATT TTTACCCAAA AAAATATATA TTAATGAAAA AAAAAGGTGG

AAAGTGCCAT AGGCACCTAT ATCCCACAAA CTAGCTATAA GATATTGAAA

GACAAATAGA TCCATAGATA AATATTTGCG TGTCCTTTCT TTTCATATCT

AATTTTTTGT TTTTTTATTT TTTTCCAATA GTCAATTTTG GCAGCTTAAC

TTCTTTCCAT AAATAATGAT GCCAAACTAT TCAATGTAAA ATTTAGATTT

ATTTTCATTA AGGGCTTCAC CTAACAAATG TGCCTAATTT TTGTGGATTT

TTTTACCATA TGTCGCTATT TAATGACTAC CAAATTATAG AATTATTTAA

GTCAATTTCT CAGTCCCCGC TCCAATATAT AAAGTTATAG AAAGGACAAT

TCTTAATTCA TAGTAATTCA AAAATCATTA AGACTAAAAA AA (720 bp)
THCA Synthase (THCAS) 1330 promoter
SEQ ID NO: 25

TTTTCAATTG ATTTAATTTC TTATATTGAT ATAAAGAATT TGCAATACAT

TGAGTTTCTT AACCCGAATA TTAAACGGTT TTGAATATCT TCATCATTGA

TTGAATAATA AAGTGGATAG TAGAGGGAAT TAGAATCCAT AATTTTTTAT

TTATATATTT GAAGTTAGTT TATTATTCTT TGCTATCCTT CATTTAATTT

TGCTATTTGT TATTTTAGTT TCAAAAATTT ATTTTTCATT ACAAAATAAA

AAATAAGATA GGATATTGGT ACTTGATAAG TCTTCTTTGT GGAAACGATA

ATCGGTATTA TTAGGTATAT TTGCATATTT CAATATTATT GCAAAAAATA

AATATATTAA TAAATAAAGT GGAAGGTGCC ATAGGTACCT ATATCCACAA

ACTAGCATAT TGAAAGAALA TGGATCCAAG GATAAATATT TGCAAGTCTT

TTTTTTTTTG CATAGCCAAT TTCTTTTTTT ATTATTATTT TAATAGAATA

TTTCAAAAGG GCATCTAACA TTTATTTTTA ATAAGGACTG CACCTAACAA

AGGTGCCTAA TTTTTGTGAA CTTTTTTTTA CCACATGTGA CTATTTAATG

AGTACTAAAT TATGAAATAT TTAGTTAATT TCTTTGCCCC CGCTCCAATA

TATAATGCTA TAAATAGCAT AATTTTCTAT TCATAGTAAT TCAAAAATCA

TTAGGACTAA AGAACCATGG (716 bp)
THCA Synthase (THCAS) 1330' promoter
SEQ ID NO: 26

TTTTCAATTG ATTTAATTTC TTATATTGAT ATAAAGAATT TGCAATACAT

TGAGTTTCTT AACCCGAATA TTAAACGGTT TTGAATATCT TCATCATTGA

TTGAATAATA AAGTGGATAG TAGAGGGAAT TAGAATCCAT AATTTTTTAT

TTATATATTT GAAGTTAGTT TATTATTCTT TGCTATCCTT CATTTAATTT

TGCTATTTGT TATTTTAGTT TCAAAAATTT ATTTTTCATT ACAAAATAAA

AAATAAGATA GGATATTGGT ACTTGATAAG TCTTCTTTGT GGAAACGATA

ATCGGTATTA TTAGGTATAT TTGCATATTT CAATATTATT GCAAAAAATA

AATATATTAA TAAATAAAGT GGAAGGTGCC ATAGGTACCT ATATCCACAA

ACTAGCATAT TGAAAGAAAA TGGATCCAAG GATAAATATT TGCAAGTCTT

TTTTTTTTTG CATAGCCAAT TTCTTTTTTT ATTATTATTT TAATAGAATA

TTTCALLAGG GCATCTAACA TTTATTTTTA ATAAGGACTG CACCTAACAA

AGGTGCCTAA TTTTTGTGAA CTTTTTTTTA CCACATGTGA CTATTTAATG

AGTACTAAAT TATGAAATAT TTAGTTAATT TCTTTGCCCC CGCTCCAATA

TATAATGCTA TAAATAGCAT AATTTTCTAT TCATAGTAAT TCAAAAATCA

TTAGGACTAA AGAAAG (1635 bp)
THCA Synthase (THCAS) ORF
SEQ ID NO: 27

1 atgaattgct cagcattttc cttttggttt gtttgcaaaa taatattttt ctttctctca 61 ttcaatatcc aaatttcaat agctaatcct caagaaaact tccttaaatg cttctcggaa

```
 121  tatattccta  acaatccagc  aaatccaaaa  ttcatataca  ctcaacacga  ccaattgtat
 181  atgtctgtcc  tgaattcgac  aatacaaaat  cttagattca  cctatgatac  aaccccaaaa
 241  ccactcgtta  ttgtcactcc  ttcaaatgtc  tcccatatcc  aggccagtat  tctctgctcc
 301  aagaaagttg  gtttgcagat  tcgaactcga  agcggtggcc  atgatgctga  gggtatgtcc
 361  tacatatctc  aagtcccatt  tgttgtagta  gacttgagaa  acatgcattc  gatcaaaata
 421  gatgttcata  gccaaactgc  gtgggttgaa  gccggagcta  cccttggaga  agtttattat
 481  tggatcaatg  agaagaatga  gaatttagt   tttcctggtg  ggtattgccc  tactgttggc
 541  gtaggtggac  actttagtgg  aggaggctat  ggagcattga  tgcgaaatta  tggccttgcg
 601  gctgataata  tcattgatgc  acacttagtc  aatgttgatg  aaaagttct   agatcgaaaa
 661  tccatgggag  aagatctatt  tgggctata   cgtggtggag  gaggagaaaa  ctttggaatc
 721  attgcagcat  ggaaaatcaa  actggttgtt  gtcccatcaa  agtctactat  attcagtgtt
 781  aaaaagaaca  tggagataca  tgggcttgtc  aagttattta  acaaatggca  aaatattgct
 841  tacaagtatg  acaaagattt  agtactcatg  actcacttca  taacaaagaa  tattacagat
 901  aatcatggga  agaataagac  tacagtacat  ggttacttct  cttcaatttt  tcatggtgga
 961  gtggatagtc  tagtcgactt  gatgaacaag  agctttcctg  agttgggtat  taaaaaaact
1021  gattgcaaag  aatttagctg  gattgataca  accatcttct  acagtggtgt  tgtaaatttt
1081  aacactgcta  attttaaaaa  ggaaattttg  cttgatagat  cagctgggaa  gaagacggct
1141  ttctcaatta  agttagacta  tgttaagaaa  ccaattccag  aaactgcaat  ggtcaaaatt
1201  ttggaaaaat  tatatgaaga  agatgtagga  gctgggatgt  atgtgttgta  cccttacggt
1261  ggtataatgg  aggagatttc  agaatcagca  attccattcc  ctcatcgagc  tggaataatg
1321  tatgaacttt  ggtacactgc  ttcctgggag  aagcaagaag  ataatgaaaa  gcatataaac
1381  tgggttcgaa  gtgttttataa tttacgact   ccttatgtgt  cccaaaatcc  aagattggcg
1441  tatctcaatt  atagggacct  tgatttagga  aaaactaatc  ctgagagtcc  taataattac
1501  acacaagcac  gtatttgggg  tgaaaagtat  tttggtaaaa  attttaacag  gttagttaag
1561  gtgaaaacca  agctgatcc   caataatttt  tttdgaaacg  aacaaagtat  cccacctctt
1621  ccaccgcatc  atcat
```

(804 bp)
CBCA Synthase (CBCAS) 3498 promoter

SEQ ID NO: 28

```
GATAATTTTT CTTCCAAATT TAATAGTATC TTTTATATAA GTTCAGTCAT
GTTTTCTTA  TGTAAGTTAG GCTATTAATT ATTTTGATGT ATTTATTATA
TTGTATGTCG TTTACTGCAT TCTGCCAACA TTGGTTTTTG TCGATTTATG
ATATATAATA TGATATGCTG TTAAGTTAGA GGTAAGATTC AATTTATTTA
AGATTATTTA ATTTGCGCTT TTATTATATA CATCTTCTAG TTGTAATTAA
TGGGGTAGAA TTAAGACTGT GTTTTGAATT AATATCGGTA TTAGAATAGG
ATTTGCATGA CTATATTTCT ACCTTACCAA GTTTTTTATC TGATAACACC
CTTTCACTTA TTATTTTCTT ATTTTTAATT TATTTAT
ATTTTTACCATATTCTATTTATACTAATCTTAAGTGGTACATTACCTCCCTGTG
GATACGACATATA
ATCTGTTTACTATCGTGACCGAAGTATAACTAATTGGGCGACATCACACCTATA
```

```
TCCCACAAACTAGCTACTATAGTCAATTTCTTGTTTTTTTCCAATAGCCAATT
TTAAATGATGCCAAACTATTCAATGTATAATGTACATTTATTTTAAATAAGGGC
TTCACCTAACAAATGTGCCTAATTTTAGTTAATTTATTTTTTTATCGCATCTTA
CTATTTAAAGGAACTATCAAATTATAAAATATTTATGTCAATTCATTTGCCCCA
ACTCCAATATATAATATTATAAATAGGATAGTTCTCTATTCATAATAATTCAAA
ATATCATTAGGACTGAAGAACCATGG
```

(800 bp)
CBCA Synthase (CBCAS) 3498' promoter

SEQ ID NO: 29

```
GATAATTTTT CTTCCAAATT TAATAGTATC TTTTATATAA GTTCAGTCAT
GTTTTTCTTA TGTAAGTTAG CTATTAATT ATTTTGATGT ATTTATTATA
TTGTATGTCG TTTACTGCAT TCTGCCAACA TTGGTTTTTG TCGATTTATG
ATATATAATA TGATATGCTG TTAAGTTAGA GGTAAGATTC AATTTATTTA
AGATTATTTA ATTTGCGCTT TTATTATATA CATCTTCTAG TTGTAATTAA
TGGGGTAGAA TTAAAACTGT GTTTTGAATT AATATCGGTA TTAGAATAGG
ATTTGCATGA CTATATTTCT ACCTTACCAA GTTTTTTATC TGATAACACC
CTTTCACTTA TTATTTTCTT ATTTTTAATT TATTTAT
```

```
ATTTTTACCATATTCTATTTATACTAATCTTAAGTGGTACATTACCTCCCTGTG
GATACGACATATA
ATCTGTTTACTATCGTGACCGAAGTATAACTAATTGGGCGACATCACACCTATA
TCCCACAAACTAGCTACTATAGTCAATTTCTTGTTTTTTTCCAATAGCCAATT
TTAAATGATGCCAAACTATTCAATGTATAATGTACATTTATTTTAAATAAGGGC
TTCACCTAACAAATGTGCCTAATTTTAGTTAATTTATTTTTTTATCGCATCTTA
CTATTTAAAGGAACTATCAAATTATAAAATATTTATGTCAATTCATTTGCCCCA
ACTCCAATATATAATATTATAAATAGGATAGTTCTCTATTCATAATAATTCAAA
ATATCATTAGGACTGAAGAAAA
```

(1635 bp)
CBCA Synthase (CBCAS) ORF

SEQ ID NO: 30

```
  1   atgaattgct caacattctc cttttggttt gtttgcaaaa taatattttt ctttctctca
 61   ttcaatatcc aaatttcaat agctaatcct caagaaaact tccttaaatg cttctcggaa
121   tatattccta caatccagc aaatccaaaa ttcatataca ctcaacacga ccaattgtat
181   atgtctgtcc tgaattcgac aatacaaaat cttagattca cctctgatac aaccccaaaa
241   ccactcgtta ttgtcactcc ttcaaatgtc tcccatatcc aggccagtat tctctgctcc
301   aagaaagttg gtttgcagat cgaactcga agcggtggcc atgatgctga gggtttgtcc
361   tacatatctc aagtcccatt tgctatagta gacttgagaa acatgcatac ggtcaaagta
421   gatattcata gccaaactgc gtgggttgaa gccggagcta cccttggaga agtttattat
481   tggatcaatg agatgaatga gaattttagt tttcctggtg ggtattgccc tactgttggc
541   gtaggtggac actttagtgg aggaggctat ggagcattga tgcgaaatta tggccttgcg
601   gctgataata tcattgatgc acacttagtc aatgttgatg aaaagttct agatcgaaaa
661   tccatgggag aagatctatt tgggctata cgtggtggag gaggagaaaa ctttggaatc
```

| | |
|---|---|
| 721 | attgcagcat gtaaaatcaa acttgttgtt gtcccatcaa aggctactat attcagtgtt |
| 781 | aaaaagaaca tggagataca tgggcttgtc aagttattta acaaatggca aaatattgct |
| 841 | tacaagtatg acaaagattt aatgctcacg actcacttca gaactaggaa tattacagat |
| 901 | aatcatggga agaataagac tacagtacat ggttacttct cttccatttt tcttggtgga |
| 961 | gtggatagtc tagttgactt gatgaacaag agctttcctg agttgggtat taaaaaaact |
| 1021 | gattgcaaag aattgagctg gattgataca accatcttct acagtggtgt tgtaaattac |
| 1081 | aacactgcta attttaaaaa ggaaattttg cttgatagat cagctgggaa gaagacggct |
| 1141 | ttctcaatta agttagacta tgttaagaaa ctaatacctg aaactgcaat ggtcaaaatt |
| 1201 | ttggaaaaat tatatgaaga agaggtagga gttgggatgt atgtgttgta cccttacggt |
| 1261 | ggtataatgg atgagatttc agaatcagca attccattcc ctcatcgagc tggaataatg |
| 1321 | tatgaacttt ggtacactgc tacctgggag aagcaagaag ataacgaaaa gcatataaac |
| 1381 | tgggttcgaa gtgtttataa tttcacaact ccttatgtgt cccaaaatcc aagattggcg |
| 1441 | tatctcaatt atagggacct tgatttagga aaaactaatc ctgagagtcc taataattac |
| 1501 | acacaagcac gtatttgggg tgaaaagtat tttggtaaaa attttaacag gttagttaag |
| 1561 | gtgaaaacca agctgatcc caataatttt tttagaaacg aacaaagtat cccacctctt |
| 1621 | ccaccgcgtc atcat |

(171 bp)
CANON fragment

SEQ ID NO: 31 atgatgccaaactattcaatgtacaatgtacatttatttttaataagggcttcacctaacaa aggtgcctaattttttgtgaactttttttttaccacatgtgactatttaatgactatcaaatta taaaatatttaagtcaatttctttgcccccactccaatatataatgt (232 bp)
CANON fragment with putative TATA Box, 5'UTR, and start codon

SEQ ID NO: 32 atgatgccaaactattcaatgtacaatgtacatttatttttaataagggcttcacctaacaa agtgcctaattttttgtgaactttttttttaccacatgtgactatttaatgactatcaaatta taaaatatttaagtcaatttctttgcccccactccaatatataatgttataaataggataat tctcaattcatagtaattcaaaaatcattaggactaaagaaaaatg

(709 bp)
4 x CANON fragment synthetic promoter

SEQ ID NO: 33 atgatgccaaactattcaatgtacaatgtacatttatttttaataagggcttcacctaacaa aggtgcctaattttttgtgaactttttttttaccacatgtgactatttaatgactatcaaatta taaaatatttaagtcaatttctttgcccccactccatgatgccaaactattcaatgtacaat gtacatttatttttaataagggcttcacctaacaaaggtgcctaattttttgtgaactttttt ttaccacatgtgactatttaatgactatcaaattataaaatatttaagtcaatttctttgcc cccactccatgatgccaaactattcaatgtacaatgtacatttatttttaataagggcttca cctaacaaaggtgcctaattttttgtgaactttttttttaccacatgtgactatttaatgacta tcaaattataaaatatttaagtcaatttctttgcccccactccatgatgccaaactattcaa tgtacaatgtacatttatttttaataagggcttcacctaacaaaggtgcctaattttttgtga acttttttttaccacatgtgactatttaatgactatcaaattataaaatatttaagtcaatt -continued

SEQUENCE LISTING

<u>tctttgccccactcc</u>aatatataatgttataaataggataattctcaattcatagtaattc aaaaatcattaggactaaagaaaaatg

What is claimed is:

1. A synthetic DNA molecule comprising a nucleotide sequence selected from the group consisting of
   (a) a nucleotide sequence set forth in any one of SEQ ID NOs: 1-3; and
   (b) a nucleotide sequence that is at least about 95% identical to the nucleotide sequence of any one of SEQ ID NOs: 1-3, or 31-33, and which encodes a promoter having plant trichome gland specific transcriptional activity,
   wherein the nucleotide sequence of (a) or (b) is operably linked to a heterologous nucleic acid.

2. An expression vector comprising the synthetic DNA molecule of claim 1.

3. A genetically engineered plant cell comprising the expression vector of claim 2.

4. The genetically engineered host cell of claim 3, wherein the cell is a *Cannabis sativa* cell.

5. The genetically engineered host cell of claim 3, wherein the cell is a *Nicotiana tabacum* cell.

6. A genetically engineered plant comprising a cell comprising a chimeric nucleic acid construct comprising the synthetic DNA molecule of claim 1.

7. The engineered plant of claim 6, wherein the plant is an *N. tabacum* plant.

8. The engineered plant of claim 6, wherein the plant is a *C. sativa* plant.

9. Seeds from the engineered plant of claim 6, wherein the seeds comprise the chimeric nucleic acid construct.

10. A genetically engineered plant or plant cell comprising a chimeric gene integrated into its genome, the chimeric gene comprising a trichome specific promoter operably linked to a homologous or heterologous nucleic acid sequence, wherein the promoter is selected from the group consisting of:
    (a) a nucleotide sequence of any one of SEQ ID NOs: 1-3; and
    (b) a nucleotide sequence that is at least about 95% identical to the nucleotide sequence of any one of SEQ ID NOs: 1-3, or 31-33, and which encodes the promoter that has plant trichome gland specific transcriptional activity.

11. The genetically engineered plant or plant cell of claim 10, wherein the plant is an *N. tabacum* plant.

12. The genetically engineered plant or plant cell of claim 10, wherein the plant is a *C. sativa* plant.

13. A method for expressing a polypeptide in plant trichomes, comprising:
    (a) introducing into a host cell an expression vector comprising a nucleotide sequence selected from the group consisting of:
        (i) a nucleotide sequence set forth in any one of SEQ ID NOs: 1-3; and (ii) a nucleotide sequence that is at least about 95% identical to the nucleotide sequence of any one of SEQ ID NOs: 1-3, and which encodes a promoter that has plant trichome gland specific transcriptional activity;
wherein the nucleic acid sequence of (i) or (ii) is operably linked to one or more nucleic acid sequences encoding a polypeptide; and
(b) growing the plant under conditions which allow for the expression of the polypeptide.

* * * * *

SEQUENCE LISTING

<160> NUMBER OF SEQ ID NOS: 33

<210> SEQ ID NO 1
<211> LENGTH: 554
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
aaaaataaaa ttaataaatt tttaattatt aatatcattt tattttttaa taaataaata      60
tcatttttat attattataa tatgtataaa gttttaattg tatacaagaa gtcttatagt     120
aagagtatac accttacatc ataataacta ctcgatctga atcaatggt caagaaaagt      180
tccctaccgg taggaaactt tgctagatc ctaccatagt cttcccttat atttattatg     240
tagaatctat tattatatct aataattaac aaatattaac aaatcatttt gaaaaattat     300
attaaaaaaa aaacttgaaa agtcaaagat taaccatcaa tttgccaaat caaattagtg     360
agaaagtagg tattatatac ctaacactca ttttacatat gtctagacgt ttatatgtat     420
agcgttgttg tgtgtaataa gttcacttgt agtatcttgt acatacataa tatatatata     480
taggtgtgtt tgtgaacaat tatattatca cacatacaca actcattatt atcataataa     540
taataatacc atgg                                                       554
```

<210> SEQ ID NO 2
<211> LENGTH: 550
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
aaaaataaaa ttaataaatt tttaattatt aatatcattt tattttttaa taaataaata      60
tcatttttat attattataa tatgtataaa gttttaattg tatacaagaa gtcttatagt     120
aagagtatac accttacatc ataataacta ctcgatctga atcaatggt caagaaaagt      180
tccctaccgg taggaaactt tgctagatc ctaccatagt cttcccttat atttattatg     240
tagaatctat tattatatct aataattaac aaatattaac aaatcatttt gaaaaattat     300
attaaaaaaa aaacttgaaa agtcaaagat taaccatcaa tttgccaaat caaattagtg     360
agaaagtagg tattatatac ctaacactca ttttacatat gtctagacgt ttatatgtat     420
agcgttgttg tgtgtaataa gttcacttgt agtatcttgt acatacataa tatatatata     480
taggtgtgtt tgtgaacaat tatattatca cacatacaca actcattatt atcataataa     540
taataataat                                                            550
```

<210> SEQ ID NO 3
<211> LENGTH: 558

<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3

```
aaaaataaaa ttaataaatt tttaattatt aatatcattt tatttttaa taaataaata      60 tcatttttat attattataa tatgtataaa gttttaattg tatacaagaa gtcttatagt    120
aagagtatac accttacatc ataataacta ctcgatctga aatcaatggt caagaaaagt    180
tccctaccgg taggaaactt ttgctagatc ctaccatagt cttcccttat atttattatg    240
tagaatctat tattatatct aataattaac aaatattaac aaatcatttt gaaaaattat    300
attaaaaaaa aaacttgaaa agtcaaagat taaccatcaa tttgccaaat caaattagtg    360
agaaagtagg tattatatac ctaacactca ttttacatat gtctagacgt ttatatgtat    420
agcgttgttg tgtgtaataa gttcacttgt agtatcttgt acatacataa tatatatata    480
tataggtgtg tttgtgaaca attatattat cacacataca caactcatta ttattagcat    540
aataataata ataataat                                                  558
```

<210> SEQ ID NO 4
<211> LENGTH: 1158
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4

```
atgaatcatc ttcgtgctga gggtccggcc tccgttctcg ccattggcac cgccaatccg      60
gagaacattt tattacaaga tgagtttcct gactactatt ttcgcgtcac caaaagtgaa    120
cacatgactc aactcaaaga aaagtttcga aaaatatgtg acaaaagtat gataaggaaa    180
cgtaactgtt tcttaaatga agaacaccta aagcaaaacc caagattggt ggagcacgag    240
atgcaaactc tggatgcacg tcaagacatg ttggtagttg aggttccaaa acttgggaag    300
gatgcttgtg caaaggccat caaagaatgg ggtcaaccca gtctaaaat cactcatta    360 atcttcacta gcgcatcaac cactgacatg cccggtgcag actaccattg cgctaagctt    420
ctcggactga gtccctcagt gaagcgtgtg atgatgtatc aactaggctg ttatggtggt    480
ggaaccgttc tacgcattgc caaggacata gcagagaata caaaggcgc acgagttctc    540 gccgtgtgtt gtgacataat ggcttgcttg tttcgtgggc cttcagagtc tgacctcgaa    600
ttactagtgg gacaagctat ctttggtgat ggggctgctg cggtgattgt tggagctgaa    660
cccgatgagt cagttgggga aaggccgata tttgagttgg tgtcaactgg gcaaacaatc    720
ttaccaaact cggaaggaac tattggggga catataaggg aagcaggact gatatttgat    780
ttacataagg atgtgcctat gttgatctct aataatattg agaaatgttt gattgaggca    840
tttactccta ttgggattag tgattggaac tccatatttt ggattacaca cccaggtggg    900
aaagctattt tggacaaagt ggaggagaag ttgcatctaa agagtgataa gtttgtggat    960
tcacgtcatg tgctgagtga gcatgggaat atgtctagct caactgtctt gtttgttatg   1020
gatgagttga ggaagaggtc gttggaggaa gggaagtcta ccactggaga tggatttgag   1080
tggggtgttc tttttgggtt tggaccaggt ttgactgtcg aaagagtggt cgtgcgtagt   1140
gttcccatca aatattaa                                                 1158
```

<210> SEQ ID NO 5
<211> LENGTH: 996
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 5

```
aattttttgac aattttttt aatataacta acttgaagat aattcctaat acgaataaat      60
acagaaaata taaacagttt tgttataaca cttttagatc agattataat taaattttat     120
attttttgata aaaaaatcaa ttgagggtcc tatttgtacc attttagaaa atatagtgtc    180
cattttattt atttagtaaa acagagagtc taatgcgtaa cttttacaaa aatacatggt    240
ccaaaatagt atttacccctt taattttatt agcaactgtc ccaaaaaaaa tatgttttga    300
tgactgacgt acgggaatgt aaagttttgt aatagtgtat tgattcaaag acaacataaa    360
gacatcaatc tgaaatcgat ttcaatgtcc caaaaacaca ttaatgagcc ttaattgcat    420
ccgataatca ttttccattg gttttattac ttctcatata tatagacatc acatatatga    480
taggatttct tgagaataat gttaacattg agatttttat tacaactgat atattgatta    540
tgcttagatg gcttgaattt gagcgacata tatagaaaga gtatagaatg atatatatgc    600
acatccaaaa tatgtaccaa aatattaggt gacaatttag ataaatggaa gagaaaatta    660
tagaaaaatg agggtttata tttttgtggt tatttaattt tagacatagt gtgatccaat    720
aattttagga tgtataattg ttaggcacat ggattacttg ttttttttatt aagtataacc    780
ttacaaagta gatggtagta attaatgtag aaggttccaa taatgtatttt ataataattg    840
ttaggcatgc aaagcctaat taattaataa atgagggtgg ccaatggcca ctatatatat    900
caaggcatcg actgtatgta gcataatgtg atttatataa ttatcaaaaa aaaaaaataa    960
aaataagaag aagaagaaag ttgagaaaga ccatgg                               996
```

<210> SEQ ID NO 6
<211> LENGTH: 992
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 6

```
aattttttgac aattttttt aatataacta acttgaagat aattcctaat acgaataaat      60
acagaaaata taaacagttt tgttataaca cttttagatc agattataat taaattttat     120
attttttgata aaaaaatcaa ttgagggtcc tatttgtacc attttagaaa atatagtgtc    180
cattttattt atttagtaaa acagagagtc taatgcgtaa cttttacaaa aatacatggt    240
ccaaaatagt atttacccctt taattttatt agcaactgtc ccaaaaaaaa tatgttttga    300
tgactgacgt acgggaatgt aaagttttgt aatagtgtat tgattcaaag acaacataaa    360
gacatcaatc tgaaatcgat ttcaatgtcc caaaaacaca ttaatgagcc ttaattgcat    420
ccgataatca ttttccattg gttttattac ttctcatata tatagacatc acatatatga    480
taggatttct tgagaataat gttaacattg agatttttat tacaactgat atattgatta    540
tgcttagatg gcttgaattt gagcgacata tatagaaaga gtatagaatg atatatatgc    600
acatccaaaa tatgtaccaa aatattaggt gacaatttag ataaatggaa gagaaaatta    660
tagaaaaatg agggtttata tttttgtggt tatttaattt tagacatagt gtgatccaat    720
```

```
aattttagga tgtataattg ttaggcacat ggattacttg tttttttatt aagtataacc      780
ttacaaagta gatggtagta attaatgtag aaggttccaa taatgtattt atataaattg      840
ttaggcatgc aaagcctaat taattaataa atgagggtgg ccaatggcca ctatatatat      900
caaggcatcg actgtatgta gcataatgtg atttatataa ttatcaaaaa aaaaaaataa      960
aaataagaag aagaagaaag ttgagaaaga ga                                   992
```

<210> SEQ ID NO 7
<211> LENGTH: 485
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 7

```
aaaaaagaag aagaagaaga aagttgagaa agagaatggc agtgaagcat ttgattgtat       60
tgaagttcaa agatgaaatc acagaagccc aaaaggaaga attttcaag acgtatgtga      120 atcttgtgaa tatcatccca gccatgaaag atgtatactg gggtaaagat gtgactcaaa      180
agaataagga agagggtac actcacatag ttgaggtaac atttgagagt gtggagacta      240
ttcaggacta cattattcat cctgcccatg ttggatttgg agatgtctat cgttctttct      300
gggaaaaact tctcattttt gactacacac cacgaaagta gactatatat agtagccgac      360
caagctgcct tcatcttcat cttctcaaat aatatatcta atatctaatt atataataat      420
aactacttaa taaaagactg tgtttataac attaaataat aataataata aagtcttttg      480
tagct                                                                  485
```

<210> SEQ ID NO 8
<211> LENGTH: 1361
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8

```
tcaaaccaga ttttttataa taatttacac accaattaac taagaaattc taactagagt       60
tagtgttgaa ttagaaggag tatcaaggta acctatctcc tttgtctctt taaattttta      120
aaagaaaagc tattgttgta attagtttgg attttatggg ttaggttttg tagagtttgt      180
ttgagcttaa aattgttgtt ggtttgattt aaggttgaat tctgtgttgg tttgtaagat      240
tttagctgat gtagttcgtg ttggaggagt tcgagttttt gaactcaaag tccactcaac      300
aatatggtga aattagtttt aggtggtttt agatgctttt gaagtgtatg ttttgtttag      360
attaccctct ttttggtaag tttgatagcc tttggtcaag gaatgactta attttgaagg      420
tctgaaagtt gagtagtttt gaactctttt ctgcccaaaa tggtttcgaa tgagttgtac      480
ttgtcatatg tgatttgagt ggtaaggttc ggaagggtag tcctagacag tgttttcaat      540
gattaggttt ggggttggtg aatctagagt taagagccta gagttttggt tgcttggatt      600
ggtgtgacct ggttgttagt atccttatca agggatcccg aataggtgat gagtgaggtt      660
tggatggtat attctggatc aaaatttta gatggggtcc aaactgatag tttcaaaaat      720
gtgtgtgtgt gtctggttaa ggatttattt tgggaaggct ctagttggga ggtcctggat      780
tggaagttct agatgtgagg ctccgggtag gagggtcctg taggaagatt ctagatggta      840
```

| tttggtggtc gagatgaggg atttccgaac atgttttaat agttacaata attcataaat | 900 |
| tttcaacact aaatcaaaat attaattttg atatgattgt ataaatttaa tctcatcgta | 960 |
| gtgtagagct ctacatgcat gcatggtttg tatagccata attaattaat taggcaagaa | 1020 |
| agatagatgt gcctaccatg catgacttct aaaacatgga tgactttaaa ttttgaaacc | 1080 |
| aagcaaaaat tgttttacta taaatcttgt taattttttca ttattgatat cactatgtta | 1140 |
| ttctaaccct ttcgtagcca taattagtta attaggcaag aaagatagat gtgcctacca | 1200 |
| tgcatgactt ctaaaacatg gatgacttta aattttgaaa ccaagcaaaa attattttac | 1260 |
| tataaatctt gttatttttt cattattgat atcactatgt tattctaacc ctttctttcc | 1320 |
| ctcattttttt cttaatattc aatcaataat aatctccatg g | 1361 |

<210> SEQ ID NO 9
<211> LENGTH: 1357
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 9

| tcaaaccaga tttttttataa taatttacac accaattaac taagaaattc taactagagt | 60 |
| tagtgttgaa ttagaaggag tatcaaggta acctatctcc tttgtctctt taaattttta | 120 |
| aaagaaaagc tattgttgta attagtttgg attttatggg ttaggttttg tagagtttgt | 180 |
| ttgagcttaa aattgttgtt ggtttgattt aaggttgaat tctgtgttgg tttgtaagat | 240 |
| tttagctgat gtagttcgtg ttggaggagt tcgagttttt gaactcaaag tccactcaac | 300 |
| aatatggtga aattagtttt aggtggtttt agatgctttt gaagtgtatg ttttgtttag | 360 |
| attaccctct ttttggtaag tttgatagcc tttggtcaag gaatgactta attttgaagg | 420 |
| tctgaaagtt gagtagtttt gaactctttt ctgcccaaaa tggtttcgaa tgagttgtac | 480 |
| ttgtcatatg tgatttgagt ggtaaggttc ggaagggtag tcctagacag tgttttcaat | 540 |
| gattaggttt ggggttggtg aatctagagt taagagccta gagttttggt tgcttggatt | 600 |
| ggtgtgacct ggttgttagt atccttatca agggatcccg aataggtgat gagtgaggtt | 660 |
| tggatggtat attctggatc aaaattttta gatgggtcc aaactgatag tttcaaaaat | 720 |
| gtgtgtgtgt gtctggttaa ggatttattt tgggaaggct ctagtggga ggtcctggat | 780 |
| tggaagttct agatgtgagg ctccgggtag gagggtcctg taggaagatt ctagatggta | 840 |
| tttggtggtc gagatgaggg atttccgaac atgttttaat agttacaata attcataaat | 900 |
| tttcaacact aaatcaaaat attaattttg atatgattgt ataaatttaa tctcatcgta | 960 |
| gtgtagagct ctacatgcat gcatggtttg tatagccata attaattaat taggcaagaa | 1020 |
| agatagatgt gcctaccatg catgacttct aaaacatgga tgactttaaa ttttgaaacc | 1080 |
| aagcaaaaat tgttttacta taaatcttgt taattttttca ttattgatat cactatgtta | 1140 |
| ttctaaccct ttcgtagcca taattagtta attaggcaag aaagatagat gtgcctacca | 1200 |
| tgcatgactt ctaaaacatg gatgacttta aattttgaaa ccaagcaaaa attattttac | 1260 |
| tataaatctt gttatttttt cattattgat atcactatgt tattctaacc ctttctttcc | 1320 |
| ctcattttttt cttaatattc aatcaataat aatctcc | 1357 |

<210> SEQ ID NO 10
<211> LENGTH: 1188
<212> TYPE: DNA

<213> ORGANISM: Artificial Sequence
<220> FEATURE:
<223> OTHER INFORMATION: Description of Artificial Sequence: Synthetic
      polynucleotide

<400> SEQUENCE: 10

| | | | | | |
|---|---|---|---|---|---|
| atgggactct | catcagtttg | tacctttca | tttcaaacta | attaccatac | tttattaaat | 60 |
| cctcacaata | ataatcccaa | aacctcatta | ttatgttatc | gacacccaa | aacaccaatt | 120 |
| aaatactctt | acaataattt | tccctctaaa | cattgctcca | ccaagagttt | tcatctacaa | 180 |
| aacaaatgct | cagaatcatt | atcaatcgca | aaaaattcca | ttagggcagc | tactacaaat | 240 |
| caaactgagc | ctccagaatc | tgataatcat | tcagtagcaa | ctaaaattt | aaactttggg | 300 |
| aaggcatgtt | ggaaacttca | agaccatat | acaatcatag | catttacttc | atgcgcttgt | 360 |
| ggattgtttg | ggaaagagtt | gttgcataac | acaaatttaa | taagttggtc | tctgatgttc | 420 |
| aaggcattct | ttttttggt | ggctatatta | tgcattgctt | cttacaac | taccatcaat | 480 |
| cagatttacg | atcttcacat | tgacagaata | acaagcctg | atctaccact | agcttcaggg | 540 |
| gaaatatcag | taaacacagc | ttggattatg | agcataattg | tggcactgtt | tggattgata | 600 |
| ataactataa | aaatgaaggg | tggaccactc | tatatatttg | gctactgttt | tggtattttt | 660 |
| ggtgggattg | tctattctgt | tccaccattt | agatggaagc | aaaatcctc | cactgcattt | 720 |
| cttctcaatt | tcctggccca | tattattaca | aattcacat | tttattatgc | cagcagagca | 780 |
| gctcttggcc | taccatttga | gttgaggcct | tctttactt | tcctgctagc | atttatgaaa | 840 |
| tcaatgggtt | cagctttggc | tttaatcaaa | gatgcttcag | acgttgaagg | cgacactaaa | 900 |
| tttggcatat | caaccttggc | aagtaaatat | ggttccagaa | acttgacatt | attttgttct | 960 |
| ggaattgttc | tcctatccta | tgtggctgct | atacttgctg | ggattatctg | gcccaggct | 1020 |
| ttcaacagta | acgtaatgtt | actttctcat | gcaatcttag | cattggtt | aatcctccag | 1080 |
| actcgagatt | ttgcgttaac | aaattacgac | ccggaagcag | gcagaagatt | ttacgagttc | 1140 |
| atgtggaagc | tttattatgc | tgaatattta | gtatatgttt | tcatataa | | 1188 |

<210> SEQ ID NO 11
<211> LENGTH: 805
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 11

| | | | | | |
|---|---|---|---|---|---|
| ataatgttat | ttattattta | atacaatatg | acatttatac | agcgtaccaa | acgagcccat | 60 |
| aatgtattgc | aattgtattg | ttgtacgaat | taaataata | aaatactaat | taagttaata | 120 |
| ttgtaagata | gataatatgg | caaacaaata | aataattttc | agttgagaat | atgtacaaaa | 180 |
| ttaaagttga | ttttacaaga | aacaagtagt | actaattaaa | atggtagatt | tacatatagt | 240 |
| gttcgttaaa | tttgaaaaaa | gaaaacgact | aattcattgg | aaaattgatt | gtggaagaaa | 300 |
| tcaaaatttg | gtggctgaac | cgccctagtt | acttaacaca | attcataaaa | caaccctaca | 360 |
| ctacttaccc | tacactatat | acgtatattt | ttttttata | ttccatttgt | taataaaata | 420 |
| aatatgcatt | gttattatgt | gtaccaagat | gctaatacgg | tgacgtttta | tataagttta | 480 |
| taatttttta | ttaaagtaaa | acaattgtcc | ctaatatta | aattaaagaa | ataagtagg | 540 |
| ttttagcatt | tctcatgata | aataagtagg | agtagtaagt | atattaattt | atatgcatat | 600 |
| gttaaaaggc | aacacagtga | taggttgtgt | agtacgtacc | caaaccaaat | tccagcctaa | 660 |

```
tccattatta atgagcaagt ccttgataaa ataaggtgca tgttgttaga tcaaataacc    720
cgtcccgaaa tccaatatat atatatatat aatattcaaa ctctctcttt ctatcttcgt    780
acaatttaat agaagtaacc atggg                                          805
```

<210> SEQ ID NO 12
<211> LENGTH: 800
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12

```
ataatgttat ttattattta atacaatatg acatttatac agcgtaccaa acgagcccat     60
aatgtattgc aattgtattg ttgtacgaat taaaataata aaatactaat taagttaata    120
ttgtaagata gataatatgg caaacaaata aataattttc agttgagaat atgtacaaaa    180
ttaaagttga ttttacaaga aacaagtagt actaattaaa atggtagatt tacatatagt    240
gttcgttaaa tttgaaaaaa gaaaacgact aattcattgg aaaattgatt gtggaagaaa    300
tcaaaatttg gtggctgaac cgccctagtt acttaacaca attcataaaa caaccctaca    360
ctacttaccc tacactatat acgtatattt tttttttata ttccatttgt taataaaata    420
aatatgcatt gttattatgt gtaccaagat gctaatacgg tgacgtttta tataagttta    480 taattttta ttaaagtaaa acaattgtcc ctcaatatta aattaaagaa aataagtagg     540
ttttagcatt tctcatgata aataagtagg agtagtaagt atattaattt atatgcatat    600
gttaaaaggc aacacagtga taggttgtgt agtacgtacc caaaccaaat tccagcctaa    660
tccattatta atgagcaagt ccttgataaa ataaggtgca tgttgttaga tcaaataacc    720
cgtcccgaaa tccaatatat atatatatat aatattcaaa ctctctcttt ctatcttcgt    780
acaatttaat agaagtaata                                                800
```

<210> SEQ ID NO 13
<211> LENGTH: 1000
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 13

```
taaaaattag attatatttt tatcagaatt ttttatttat atttttcatc gagttacgtt     60
gatttaacgt atgttgacgg tgcttataat tgtctattat ttttaagtta tatacacgca    120
ctacttacgt aaatttagtt ggcagatttt ctgtctctat gggctatatt gttggacatc    180
agctatctca ttaattaata ataccatact ttttcttaaa agttaaataa aacaaaatta    240
tacacgcact gattcgaatg gtgtagccca cgcacttgct aagtctgtta ctagttctgt    300
aggagttaat gtgtggactg atgcttgtcc tagatttat cagctatctc attaattaat     360
aataccatac ttttcttaa aagttaaata aacaaaatt atacacgcac tacgataagg      420
attatataaa tgattaacta aaaatatct atttaacatg ccataccgcg aaaggttttg     480
cgccattcga tggtgtccgg gatctcgacg ctctccctta tgcgactcct gcattaggaa    540
gcagcccagt agtaggttga ggccgttgag caccgccgcc gcaaggaatg gtgcatgcaa    600
ggagatggcg cccaacagtc cccggccac gggcctgcc accataccca cgccgaaaca     660
```

```
agcgctcatg agcccgaagt ggcgagcccg atcttcccca tcggtgatgt cggcgatata    720
ggcgccagca accgcacctg tggcgccggt gatgccggcc acgatgcgtc cggcgtagag    780
gatcgagatc tcgatcccgc gaattaata  cgactcacta gggggaatt  gtgagcggat    840 aacaattccc ctctagaaat aattttgttt aactttaaga aggagatata ccatgaaaca    900
ccaccaccac caccaccacc acggtggtct ggttccgcgt ggttcccatg atcaaacaag    960
tttgtacaaa aaagcaggct ccgaattcgc ccttatggag                         1000
```

<210> SEQ ID NO 14
<211> LENGTH: 869
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
gtgacaaact gaagaattct gtttatttta ttttatacat tagtgatgtt ttttacttt     60 ttagagttat ttttatgcct atgtaatttg catattgtag tggagtttat gcagttattt    120
ttttgttgtt atttagttgt ttaactaaga gaaataaata tatatatttt ttatttgtgc    180
gttgttttta ttttattttt taagttgacg taagtgttga tgctcaatta attttatat    240 taacataaaa ttgttattgt gttgcttatt cgttgctatt gagttatttc aatattgtac    300
tttttgaagt ttttgtctta taaatttatt tttatttgca taacatatga taaactttaa    360
tggatttata tgttacggtt aagttgtttt ctagttgctt ttgtgttgtt gtttagttgt    420
tttgcgctga gaaaagaagc cctatacgtt aaaattcact ttgtccgaat tcgccacgtg    480
gcaactactg ctacgttctg acgctacaga ttgtgagcgt caggcaagtc tgaatgcttt    540
gtcccgcact cacgtgtgag tctcactcgc ccacatagcc atatgtgtgc cacacatctc    600
cttgcgcatc taggggagtt tttctactgt attttttgtaa ataagaaact ttgaaaatag    660
tatatttgaa attaataaat aatataaatg tttattttta cttatagtag tataaatatt    720
tatttaagat aattttaact taaaatagaa aaaatctcaa aaaaaaataa aataaaataa    780
actataccct taattttat atttatgaaa atttcccgta taaaagggaa gattttttt      840 tttaaaatta gtaggtaagt aataggatg                                     869
```

<210> SEQ ID NO 15
<211> LENGTH: 2351
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 15

```
tcttggagtg tatatataga tatatatata catttctcca tttttggcca cccaaattac     60
ctaaattgaa ttcgtcgtgt tcgtctttct ccgccataaa taacaattga tttccttcgt    120
tctttcaagt ttttgtcaac tgagtactga gatccagtct gagtcgacac ttgtagaggt    180
tcgaaaatgg cgcagaagaa gtttattttt gaggttgaaa aggctaagga agctaaggat    240
ggaaggcctt ccatgggacc tgtttatcga agtatgtacg ccaaggatgg ctttcctcct    300
ccgattgatg gattggattg ttgttgggat gtgtttaggc tttctgtgga gagaaatcct    360
ggaaacaaaa tgctcggtcg ccgggaggtt gtggatggga aggctggaaa gtatgtttgg    420
caaacttata aggaggttta tgattgtgtg ataaaacttg gaaatgccat gcgcagttgt    480
```

```
ggtttcggag aaggagacaa atgtggtatc tatggtgcca attgctctga atggattatg    540
agcatgcagg cttgcaatgc tcatggactc tattgtgttc cgttgtatga caccttaggt    600
gctaatgcaa ttgagtttgt cataaaacat gccgaggtta caattgcttt tgcagaagag    660
aaaaagcttc ctgagctgtt gaaaacactt cctaacacca cagactattt aaaaacactt    720
gtgagctttg ggaaggtcac accggaacaa agggaatctg ttgaaaagtt tggattgaag    780
atctattcct gggaagagtt cttgcaattg ggtgattgta aagatttcga tcttccagtg    840
aaaaagaaaa ctgatatatg cactataatg tatactagtg gaactactgg tgacccaaag    900
ggagtactga tatccaatga gagcatcatt tctcttttgg ctggggtgag gcgattgctt    960
gagagtgtaa atgaaaagtt gaccgagaaa gatgtatttc tttcatatct tccccttgca   1020
catatcttcg atcgggtgat tgaggagtta tttattttgc atggtgcctc aatcgggttc   1080
tggcgtggcg atgtcaaatt attacttgaa gacattgggg agctaaaacc aactattttc   1140
tgtgccgttc cccgtgtgct ggatagagtc tatgctggtt tgacgcagaa gatttctgct   1200
gggggattct aaagaagac  tctcttcaat ttcgcatact cacgcaagta ataacatg     1260 cgaaaggggc ttaaacacgg ggacgcagct ccattatgtg acaaaattgt atttagtaag   1320
gtgaagcaag gtttgggagg taatgtgcgg cttattctgt ctggagctgc gcctctagct   1380
cctcatgttg aagcttactt acgagttgtg acatgtgctc atgtttgcca aggatatggg   1440
ctaactgaaa cttgtgcggg gacatttgtc tcgataccaa atgaactacc aatgctcggt   1500
acagttggtc ctccagtacc caatgttgat gtatgtctgg aatcagttcc ggaaatggga   1560
tatgatgccc ttgcagaagt accgcgtgga gaagtatgtg tgaagggaag caccttattc   1620
tctgggtact acaaacgtga agacttaacc aaggaggtca tgattgatgg gtggttccat   1680
acaggtgatg ttggtgagtg gcaagcagat ggaagcttga aaatcattga ccgtaagaaa   1740 aatatttttca aactttctca aggagaatat gtggcagttg agaacttaga gaacatttat   1800
ggtcttgttt ctgacattga ctcaatatgg gtttacggga cagcttcga gtccttcctc   1860 gttgctgtga ttaacccgaa ccagcaagca cttgaacgtt gggccggaga gaataatata   1920
tctggtgact tcaagtccat ttgtgaaaat ccaagagcaa aggaatacat tttgggagag   1980
ctcaataaga ttggcaaaga gaaaagttg aaaggtttg  agttcataag agctgttcac   2040
cttgacccag aggcatttga catagaacgt gaccttatta ctccaacata taagaaaaag   2100
agaccccagt tgctcaaata ctaccagagt gttattgata acatgtacaa ggaaggaaac   2160
aagcccagga cctgaaagat ataatagaca tttagagctt cactttctaa tatttcttca   2220
cacacttccc attttcatct ctctcttact tattacacta taaataatta acaaggttta   2280
ctgtgttgta aatgacattt taatattttc atagtctcaa tgtttcaatt cttagaggac   2340
gttttgattg g                                                        2351
```

`<210> SEQ ID NO 16`
`<211> LENGTH: 420`
`<212> TYPE: DNA`
`<213> ORGANISM: Artificial Sequence`
`<220> FEATURE:`
`<223> OTHER INFORMATION: Description of Artificial Sequence: Synthetic`
`      polynucleotide`

`<400> SEQUENCE: 16`

```
gttaataaac atacttgtga gtagatctaa gatcctggta aataattcc  caacatattt     60 caatcgtaaa ttcatgagtg attcttatca cttcttaaaa aaaagatata aagatccata    120
```

```
gataaatatt tgctagtcct ttctttccat agtcaacttc aatatggcat cttaacttct    180
ttccatcaac aaatgatgct caactactta atgtacaatt tatatttatt tttagtaagg    240
gatacaccta acaatgatgc ctaattttgg tgaattttt tttaccacat gtgacttaat    300
gatatcaaat ttggaaatat ttagttaatt tatttgcccc tgctccatta tataaagcta    360
taaataggat agttcttaat tcatagtaat tcaaaaatta ttagaactaa agaaccatgg    420
```

<210> SEQ ID NO 17
<211> LENGTH: 416
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 17

```
gttaataaac atacttgtga gtagatctaa gatcctggta aaataattcc caacatattt     60
caatcgtaaa ttcatgagtg attcttatca cttcttaaaa aaaagatata aagatccata    120
gataaatatt tgctagtcct ttctttccat agtcaacttc aatatggcat cttaacttct    180
ttccatcaac aaatgatgct caactactta atgtacaatt tatatttatt tttagtaagg    240
gatacaccta acaatgatgc ctaattttgg tgaattttt tttaccacat gtgacttaat    300
gatatcaaat ttggaaatat ttagttaatt tatttgcccc tgctccatta tataaagcta    360
taaataggat agttcttaat tcatagtaat tcaaaaatta ttagaactaa agaaaa       416
```

<210> SEQ ID NO 18
<211> LENGTH: 535
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
agacgttata gctttattgt ctaaattctc tggggtagtt ttgtcccatg ttgctcgctt     60
actttagaag ttcaaagttt gacaaaacat gctattcggt tatacaatga gctatcctag    120
ttcaaggaga ttcctgtgct atttgtggat gtctacattg taaattcatg agtgattctt    180
ataactttat taaaaaaaag acaaatagat ccatagataa atatttgcaa gtgctttctt    240
gtcatagcaa ttttttttta cataggtaat ttaaaaaatt catcttaact ttttttcatc    300
aataaatgat gctcaattat tcaatgcacc atgtacattt attttttaata agggctgcac    360 ctaacaaagg tgcctaattt tggtaaaaaa gaaattacgg catgtgaata tttaatgagc    420
atcaaattac aaaatattta gctaattttct ttacccccac tccaatctat aaagctataa    480
ataggataat tttccattca tagtaatttc caacattacg actaaagaac catgg         535
```

<210> SEQ ID NO 19
<211> LENGTH: 531
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 19

```
agacgttata gctttattgt ctaaattctc tggggtagtt ttgtcccatg ttgctcgctt     60
actttagaag ttcaaagttt gacaaaacat gctattcggt tatacaatga gctatcctag    120
```

```
ttcaaggaga ttcctgtgct atttgtggat gtctacattg taaattcatg agtgattctt    180
ataactttat taaaaaaaag acaaatagat ccatagataa atatttgcaa gtgctttctt    240
gtcatagcaa ttttttttta cataggtaat ttaaaaaatt catcttaact ttttttcatc    300
aataaatgat gctcaattat tcaatgcacc atgtacattt atttttaata agggctgcac    360
ctaacaaagg tgcctaattt tggtaaaaaa gaaattacgg catgtgaata tttaatgagc    420
atcaaattac aaaatattta gctaatttct ttaccccccac tccaatctat aaagctataa    480
ataggataat tttccattca tagtaatttc caacattacg actaaagaaa a             531
```

<210> SEQ ID NO 20
<211> LENGTH: 1635
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 20

```
atgaagtgct caacattctc cttttggttt gtttgcaaga taatattttt cttttctca     60 ttcaatatcc aaacttccat tgctaatcct cgagaaaact tccttaaatg cttctcgcaa    120
tatattccca ataatgcaac aaatctaaaa ctcgtataca ctcaaaacaa cccattgtat    180
atgtctgtcc taaattcgac aatacacaat cttagattca cctctgacac aaccccaaaa    240
ccacttgtta tcgtcactcc ttcacatgtc tctcatatcc aaggcactat tctatgctcc    300
aagaaagttg gcttgcagat tcgaactcga agtggtggtc atgattctga gggcatgtcc    360
tacatatctc aagtcccatt tgttatagta gacttgagaa acatgcgttc aatcaaaata    420
gatgttcata gccaaactgc atgggttgaa gccggagcta cccttggaga agtttattat    480
tgggttaatg agaaaaatga gaatcttagt ttggcggctg ggtattgccc tactgtttgc    540
gcaggtggac actttggtgg aggaggctat ggaccattga tgagaaacta tggcctcgcg    600
gctgataata tcattgatgc acacttagtc aacgttcatg gaaaagtgct agatcgaaaa    660
tctatggggg aagatctctt tgggctttta cgtggtggtg gagcagaaag cttcggaatc    720
attgtagcat ggaaaattag actggttgct gtcccaaagt ctactatgtt tagtgttaaa    780
aagatcatgg agatacatga gcttgtcaag ttagttaaca atggcaaaa tattgcttac    840 aagtatgaca agatttatt actcatgact cacttcataa ctaggaacat tacagataat    900
caagggaaga ataagacagc aatacacact tacttctctt cagttttcct tggtggagtg    960
gatagtctag tcgacttgat gaacaagagt tttcctgagt tgggtattaa aaaacggat   1020 tgcagacaat tgagctggat tgatactatc atcttctata gtggtgttgt aaattacgac   1080
actgataatt ttaacaagga atttttgctt gatagatccg ctgggcagaa cggtgctttc   1140
aagattaagt tagactacgt taagaaacca attccagaat ctgtatttgt ccaaattttg   1200
gaaaaattat atgaagaaga tataggagct gggatgtatg cgttgtaccc ttacggtggt   1260
ataatggatg agatttcaga atcagcaatt ccattccctc atcgagctgg aatcttgtat   1320
gagttatggt acatatgtag ttgggagaag caagaagata acgaaaagca tctaaactgg   1380
attagaaata tttataactt catgactcct tatgtgtcca aaatccaag attggcatat   1440 ctcaattata gagccttga tataggaata atgatccca agaatccaaa taattacaca   1500
caagcacgta tttggggtga aagtattttt ggtaaaaatt ttgacaggct agtaaaagtg   1560
```

```
aaaaccctgg ttgatcccaa taactttttt agaaacgaac aaagcatccc acctcttcca   1620
cggcatcgtc attaa                                                    1635

<210> SEQ ID NO 21
<211> LENGTH: 800
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
cttatcactc attcgggagc aacttaaaaa aattacaatt attatgaaag acggcacaaa     60
aagcgaatta attacctaat cgtaaataaa agaaatttta cataaatata ttatataatt    120
ttatattatt cataaaaaat ataaaatagt attagactga attgagattt gattcgtaac    180
taaaaattaa tttctttaat gtaaaatttt aaaaacaaat tattaaaacc gcgtgaagcg    240
cggatctatt ccctagttga ataataaagt agatagtaga ggaggttaga atttataatt    300
tttcatttaa atatttgaat ttactttact gttctttgtt attcttcatt taattttgct    360
atttgttatt ttacttttca aaattataa ttttaattac caaataaaaa gtaaaataga    420
tattggtact tgatattcac tctttatggg aaccataata aactataaaa gtcattatgt    480
gtacttgcta ccataggcac ctatatccca caaactagct accatagcca atttcttgtt    540
ttttgtttcc aatatccaat ttttattgat gccaaactat tcaatgtaca atgtacattt    600
attttcaata agggcttcac ctaacaaagg tgcctaattt tagttgattt attttttatc    660
acatgtgact atttaatgac tatcaaatta taaaatattt aagtcaattt atttgcccca    720
actccaatat ataatattat aaataggata gttctcaatt cctaataatt caaaaaatca    780
ttaggactga agaaccatgg                                                800

<210> SEQ ID NO 22
<211> LENGTH: 796
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
cttatcactc attcgggagc aacttaaaaa aattacaatt attatgaaag acggcacaaa     60
aagcgaatta attacctaat cgtaaataaa agaaatttta cataaatata ttatataatt    120
ttatattatt cataaaaaat ataaaatagt attagactga attgagattt gattcgtaac    180
taaaaattaa tttctttaat gtaaaatttt aaaaacaaat tattaaaacc gcgtgaagcg    240
cggatctatt ccctagttga ataataaagt agatagtaga ggaggttaga atttataatt    300
tttcatttaa atatttgaat ttactttact gttctttgtt attcttcatt taattttgct    360
atttgttatt ttacttttca aaattataa ttttaattac caaataaaaa gtaaaataga    420
tattggtact tgatattcac tctttatggg aaccataata aactataaaa gtcattatgt    480
gtacttgcta ccataggcac ctatatccca caaactagct accatagcca atttcttgtt    540
ttttgtttcc aatatccaat ttttattgat gccaaactat tcaatgtaca atgtacattt    600
attttcaata agggcttcac ctaacaaagg tgcctaattt tagttgattt attttttatc    660
acatgtgact atttaatgac tatcaaatta taaaatattt aagtcaattt atttgcccca    720
```
actccaatat ataatattat aaataggata gttctcaatt cctaataatt caaaaaatca    780
ttaggactga agaaaa    796

<210> SEQ ID NO 23
<211> LENGTH: 796
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
ttatttaaat ttctcagaga gatatagaga atttacaata ggtcaagttg tatattttt    60 aatccgaata attaatgctt ttgaatatcc atcatcaata ttgaataata aagtagatag    120
cagaggagat tagaactcat aattttcat ttatatttt gaatttagtt tactgttctt    180
tattattctt catttaattt tgctatatgt tattttactt ttcaaaaatt ctaattttga    240
ttaccaaata aaaataaaa tatatattgg tacttcatat ttagttttta tgggaatgat    300
aatgaatgat attgtaataa actataaaag taattttgta tacttgcata gttcttaatt    360
tttacccaaa aaaatatata ttaatgaaaa aaaaaggtgg aaagtgccat aggcacctat    420
atcccacaaa ctagctataa gatattgaaa gacaaataga tccatagata aatatttgcg    480
tgtcctttct tttcatatct aatttttgt tttttattt ttttccaata gtcaattttg    540
gcagcttaac ttctttccat aaataatgat gccaaactat tcaatgtaaa atttagattt    600
attttcatta agggcttcac ctaacaaatg tgcctaattt ttgtggattt ttttaccata    660
tgtcgctatt taatgactac caaattatag aattatttaa gtcaatttct cagtccccgc    720
tccaatatat aaagttatag aaaggacaat tcttaattca tagtaattca aaaatcatta    780
agactaaaaa ccatgg    796

<210> SEQ ID NO 24
<211> LENGTH: 792
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
ttatttaaat ttctcagaga gatatagaga atttacaata ggtcaagttg tatattttt    60 aatccgaata attaatgctt ttgaatatcc atcatcaata ttgaataata aagtagatag    120
cagaggagat tagaactcat aattttcat ttatatttt gaatttagtt tactgttctt    180
tattattctt catttaattt tgctatatgt tattttactt ttcaaaaatt ctaattttga    240
ttaccaaata aaaataaaa tatatattgg tacttcatat ttagttttta tgggaatgat    300
aatgaatgat attgtaataa actataaaag taattttgta tacttgcata gttcttaatt    360
tttacccaaa aaaatatata ttaatgaaaa aaaaaggtgg aaagtgccat aggcacctat    420
atcccacaaa ctagctataa gatattgaaa gacaaataga tccatagata aatatttgcg    480
tgtcctttct tttcatatct aatttttgt tttttattt ttttccaata gtcaattttg    540
gcagcttaac ttctttccat aaataatgat gccaaactat tcaatgtaaa atttagattt    600
attttcatta agggcttcac ctaacaaatg tgcctaattt ttgtggattt ttttaccata    660
tgtcgctatt taatgactac caaattatag aattatttaa gtcaatttct cagtccccgc    720

```
tccaatatat aaagttatag aaaggacaat tcttaattca tagtaattca aaaatcatta      780
agactaaaaa aa                                                          792

<210> SEQ ID NO 25
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
ttttcaattg atttaatttc ttatattgat ataaagaatt tgcaatacat tgagtttctt       60
aacccgaata ttaaacggtt ttgaatatct tcatcattga ttgaataata aagtggatag      120
tagagggaat tagaatccat aattttttat ttatatattt gaagttagtt tattattctt      180
tgctatcctt catttaattt tgctatttgt tattttagtt tcaaaaattt attttttcatt    240 acaaaataaa aataagata ggatattggt acttgataag tcttctttgt ggaaacgata       300
atcggtatta ttaggtatat ttgcatattt caatattatt gcaaaaaata aatatattaa     360
taaataaagt ggaaggtgcc ataggtacct atatccacaa actagcatat tgaaagaaaa      420
tggatccaag gataaatatt tgcaagtctt ttttttttg catagccaat ttcttttttt      480
attattattt taatagaata tttcaaaagg gcatctaaca tttattttta ataaggactg      540
cacctaacaa aggtgcctaa tttttgtgaa cttttttta ccacatgtga ctatttaatg      600
agtactaaat tatgaaatat ttagttaatt tctttgcccc cgctccaata tataatgcta    660
taaatagcat aattttctat tcatagtaat tcaaaaatca ttaggactaa agaaccatgg      720

<210> SEQ ID NO 26
<211> LENGTH: 716
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 26
ttttcaattg atttaatttc ttatattgat ataaagaatt tgcaatacat tgagtttctt       60
aacccgaata ttaaacggtt ttgaatatct tcatcattga ttgaataata aagtggatag      120
tagagggaat tagaatccat aattttttat ttatatattt gaagttagtt tattattctt      180
tgctatcctt catttaattt tgctatttgt tattttagtt tcaaaaattt attttttcatt    240 acaaaataaa aataagata ggatattggt acttgataag tcttctttgt ggaaacgata       300
atcggtatta ttaggtatat ttgcatattt caatattatt gcaaaaaata aatatattaa     360
taaataaagt ggaaggtgcc ataggtacct atatccacaa actagcatat tgaaagaaaa      420
tggatccaag gataaatatt tgcaagtctt ttttttttg catagccaat ttcttttttt      480
attattattt taatagaata tttcaaaagg gcatctaaca tttattttta ataaggactg      540
cacctaacaa aggtgcctaa tttttgtgaa cttttttta ccacatgtga ctatttaatg      600
agtactaaat tatgaaatat ttagttaatt tctttgcccc cgctccaata tataatgcta    660
taaatagcat aattttctat tcatagtaat tcaaaaatca ttaggactaa agaaag         716

<210> SEQ ID NO 27
<211> LENGTH: 1635
<212> TYPE: DNA
```

<213> ORGANISM: Artificial Sequence
<220> FEATURE:
<223> OTHER INFORMATION: Description of Artificial Sequence: Synthetic polynucleotide

<400> SEQUENCE: 27

```
atgaattgct cagcattttc cttttggttt gtttgcaaaa taatattttt ctttctctca      60
ttcaatatcc aaatttcaat agctaatcct caagaaaact tccttaaatg cttctcggaa     120
tatattccta acaatccagc aaatccaaaa ttcatataca ctcaacacga ccaattgtat     180
atgtctgtcc tgaattcgac aatacaaaat cttagattca cctctgatac aaccccaaaa     240
ccactcgtta ttgtcactcc ttcaaatgtc tcccatatcc aggccagtat tctctgctcc     300
aagaaagttg gtttgcagat tcgaactcga agcggtggcc atgatgctga gggtatgtcc     360
tacatatctc aagtcccatt tgttgtagta gacttgagaa acatgcattc gatcaaaata     420
gatgttcata gccaaactgc gtgggttgaa gccggagcta cccttggaga gtttattat      480
tggatcaatg agaagaatga gaattttagt tttcctggtg ggtattgccc tactgttggc     540
gtaggtggac actttagtgg aggaggctat ggagcattga tgcgaaatta tggccttgcg     600
gctgataata tcattgatgc acacttagtc aatgttgatg aaaagttct agatcgaaaa      660
tccatgggag aagatctatt tgggctata cgtggtggag gaggagaaaa ctttggaatc      720
attgcagcat ggaaaatcaa actggttgtt gtcccatcaa agtctactat attcagtgtt     780
aaaaagaaca tggagataca tgggcttgtc aagttattta caaatggca aaatattgct      840
tacaagtatg acaaagattt agtactcatg actcacttca taacaaagaa tattacagat     900
aatcatggga agaataagac tacagtacat ggttacttct cttcaatttt tcatggtgga     960
gtggatagtc tagtcgactt gatgaacaag agctttcctg agttgggtat taaaaaaact    1020
gattgcaaag aatttagctg gattgataca accatcttct acagtggtgt tgtaaatttt    1080
aacactgcta attttaaaaa ggaaattttg cttgatagat cagctgggaa gaagacggct    1140
ttctcaatta agttagacta tgttaagaaa ccaattccag aaactgcaat ggtcaaaatt    1200
ttggaaaaat tatatgaaga agatgtagga gctgggatgt atgtgttgta cccttacggt    1260
ggtataatgg aggagatttc agaatcagca attccattcc ctcatcgagc tggaataatg    1320
tatgaacttt ggtacactgc ttcctgggag aagcaagaag ataatgaaaa gcatataaac    1380
tgggttcgaa gtgtttataa ttttacgact cctatgtgt cccaaaatcc aagattggcg     1440
tatctcaatt atagggacct tgatttagga aaaactaatc ctgagagtcc taataattac    1500
acacaagcac gtatttgggg tgaaaagtat tttggtaaaa attttaacag gttagttaag    1560
gtgaaaacca agctgatccc caataatttt tttagaaacg aacaaagtat cccacctctt    1620
ccaccgcatc atcat                                                    1635
```

<210> SEQ ID NO 28
<211> LENGTH: 804
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 28

```
gataatttt cttccaaatt taatagtatc tttatataa gttcagtcat gttttctta       60
tgtaagttag gctattaatt attttgatgt atttattata ttgtatgtcg tttactgcat     120
tctgccaaca ttggttttg tcgatttatg atatataata tgatatgctg ttaagttaga     180
```

```
ggtaagattc aatttattta agattattta atttgcgctt ttattatata catcttctag    240
ttgtaattaa tggggtagaa ttaagactgt gttttgaatt aatatcggta ttagaatagg    300
atttgcatga ctatatttct accttaccaa gttttttatc tgataacacc ctttcactta    360
ttattttctt attttttaatt tatttatatt tttaccatat tctatttata ctaatcttaa   420
gtggtacatt acctccctgt ggatacgaca tataatctgt ttactatcgt gaccgaagta    480
taactaattg ggcgacatca cacctatatc ccacaaacta gctactatag tcaatttctt    540
gttttttttc caatagccaa ttttaaatga tgccaaacta ttcaatgtat aatgtacatt    600
tattttaaat aagggcttca cctaacaaat gtgcctaatt ttagttaatt tattttttta    660
tcgcatctta ctatttaaag gaactatcaa attataaaat atttatgtca attcatttgc    720
cccaactcca atatataata ttataaatag gatagttctc tattcataat aattcaaaat    780
atcattagga ctgaagaacc atgg                                           804

<210> SEQ ID NO 29
<211> LENGTH: 800
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 29
gataattttt cttccaaatt taatagtatc ttttatataa gttcagtcat gttttttctta   60 tgtaagttag gctattaatt attttgatgt atttattata ttgtatgtcg tttactgcat    120
tctgccaaca ttggttttg tcgatttatg atatataata tgatatgctg ttaagttaga    180
ggtaagattc aatttattta agattattta atttgcgctt ttattatata catcttctag    240
ttgtaattaa tggggtagaa ttaagactgt gttttgaatt aatatcggta ttagaatagg    300
atttgcatga ctatatttct accttaccaa gttttttatc tgataacacc ctttcactta    360
ttattttctt attttttaatt tatttatatt tttaccatat tctatttata ctaatcttaa   420
gtggtacatt acctccctgt ggatacgaca tataatctgt ttactatcgt gaccgaagta    480
taactaattg ggcgacatca cacctatatc ccacaaacta gctactatag tcaatttctt    540
gttttttttc caatagccaa ttttaaatga tgccaaacta ttcaatgtat aatgtacatt    600
tattttaaat aagggcttca cctaacaaat gtgcctaatt ttagttaatt tattttttta    660
tcgcatctta ctatttaaag gaactatcaa attataaaat atttatgtca attcatttgc    720
cccaactcca atatataata ttataaatag gatagttctc tattcataat aattcaaaat    780
atcattagga ctgaagaaaa                                                800

<210> SEQ ID NO 30
<211> LENGTH: 1635
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 30
atgaattgct caacattctc cttttggttt gtttgcaaaa taatattttt ctttctctca    60
ttcaatatcc aaatttcaat agctaatcct caagaaaact tccttaaatg cttctcggaa    120
tatattccta acaatccagc aaatccaaaa ttcatataca ctcaacacga ccaattgtat    180
```

```
atgtctgtcc tgaattcgac aatacaaaat cttagattca cctctgatac aaccccaaaa    240
ccactcgtta ttgtcactcc ttcaaatgtc tcccatatcc aggccagtat tctctgctcc    300
aagaaagttg gtttgcagat tcgaactcga agcggtggcc atgatgctga gggtttgtcc    360
tacatatctc aagtcccatt tgctatagta gacttgagaa acatgcatac ggtcaaagta    420
gatattcata gccaaactgc gtgggttgaa gccggagcta cccttggaga agtttattat    480
tggatcaatg agatgaatga gaattttagt tttcctggtg ggtattgccc tactgttggc    540
gtaggtggac actttagtgg aggaggctat ggagcattga tgcgaaatta tggccttgcg    600
gctgataata tcattgatgc acacttagtc aatgttgatg aaaagttct agatcgaaaa     660 tccatgggag aagatctatt tgggctata cgtggtggag gaggagaaaa ctttggaatc      720
attgcagcat gtaaaatcaa acttgttgtt gtcccatcaa aggctactat attcagtgtt    780
aaaaagaaca tggagataca tgggcttgtc aagttattta acaaatggca aaatattgct    840
tacaagtatg acaaagattt aatgctcacg actcacttca gaactaggaa tattacagat    900
aatcatggga agaataagac tacagtacat ggttacttct cttccatttt tcttggtgga    960
gtggatagtc tagttgactt gatgaacaag agctttcctg agttgggtat taaaaaaact   1020
gattgcaaag aattgagctg gattgataca accatcttct acagtggtgt tgtaaattac   1080
aacactgcta attttaaaaa ggaaattttg cttgatagat cagctgggaa gaagacggct   1140
ttctcaatta agttagacta tgttaagaaa ctaatacctg aaactgcaat ggtcaaaatt   1200
ttggaaaaat tatatgaaga agaggtagga gttgggatgt atgtgttgta cccttacggt   1260
ggtataatgg atgagatttc agaatcagca attccattcc ctcatcgagc tggaataatg   1320
tatgaacttt ggtacactgc tacctgggag aagcaagaag ataacgaaaa gcatataaac   1380
tgggttcgaa gtgtttataa tttcacaact cctatgtgt cccaaaatcc aagattggcg    1440
tatctcaatt atagggacct tgatttagga aaaactaatc ctgagagtcc taataattac   1500
acacaagcac gtatttgggg tgaaaagtat tttggtaaaa attttaacag gttagttaag   1560
gtgaaaacca aagctgatcc caataatttt tttagaaacg aacaaagtat cccacctctt   1620
ccaccgcgtc atcat                                                    1635
```

<210> SEQ ID NO 31
<211> LENGTH: 171
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31

```
atgatgccaa actattcaat gtacaatgta catttatttt taataagggc ttcacctaac     60
aaaggtgcct aattttgtg aacttttttt taccacatgt gactatttaa tgactatcaa    120
attataaaat atttaagtca atttctttgc ccccactcca atatataatg t            171
```

<210> SEQ ID NO 32
<211> LENGTH: 232
<212> TYPE: DNA
<213> ORGANISM: Artificial Sequence
<220> FEATURE:
<223> OTHER INFORMATION: Description of Artificial Sequence: Synthetic
      polynucleotide

```
<400> SEQUENCE: 32
atgatgccaa actattcaat gtacaatgta catttatttt taataagggc ttcacctaac        60
aaaggtgcct aattttgtg aacttttttt taccacatgt gactatttaa tgactatcaa       120
attataaaat atttaagtca atttctttgc ccccactcca atatataatg ttataaatag       180
gataattctc aattcatagt aattcaaaaa tcattaggac taaagaaaaa tg              232

<210> SEQ ID NO 33
<211> LENGTH: 709
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 33
atgatgccaa actattcaat gtacaatgta catttatttt taataagggc ttcacctaac        60
aaaggtgcct aattttgtg aacttttttt taccacatgt gactatttaa tgactatcaa       120
attataaaat atttaagtca atttctttgc ccccactcca tgatgccaaa ctattcaatg       180
tacaatgtac atttatttt aataagggct tcacctaaca aaggtgccta attttgtga        240 actttttttt accacatgtg actatttaat gactatcaaa ttataaaata tttaagtcaa       300
tttctttgcc cccactccat gatgccaaac tattcaatgt acaatgtaca tttatttta        360 ataagggctt cacctaacaa aggtgcctaa ttttgtgaa ctttttttta ccacatgtga       420
ctatttaatg actatcaaat tataaaatat ttaagtcaat ttctttgccc ccactccatg       480
atgccaaact attcaatgta caatgtacat ttatttttaa taagggcttc acctaacaaa       540
ggtgcctaat ttgtgaac ttttttttac cacatgtgac tatttaatga ctatcaaatt       600
ataaaatatt taagtcaatt tctttgcccc cactccaata tataatgtta taaataggat       660
aattctcaat tcatagtaat tcaaaaatca ttaggactaa agaaaaatg                  709
```